(12) United States Patent
Kasid et al.

(10) Patent No.: US 7,351,811 B2
(45) Date of Patent: Apr. 1, 2008

(54) GENE SCC-112 AND DIAGNOSTIC AND THERAPEUTIC USES THEREOF

(75) Inventors: Usha Kasid, Rockville, MD (US); Deepak Kumar, Arlington, VA (US); Imran Ahmad, Wadsworth, IL (US)

(73) Assignee: Georgetown University, Washington, DC (US)

( * ) Notice: Subject to any disclaimer, the term of this patent is extended or adjusted under 35 U.S.C. 154(b) by 435 days.

(21) Appl. No.: 10/679,580

(22) Filed: Oct. 6, 2003

(65) Prior Publication Data

US 2004/0248218 A1 Dec. 9, 2004

Related U.S. Application Data

(63) Continuation of application No. PCT/US02/10850, filed on Apr. 8, 2002.

(60) Provisional application No. 60/281,780, filed on Apr. 6, 2001.

(51) Int. Cl.
C07H 21/04 (2006.01)

(52) U.S. Cl. .................. 536/23.1; 536/23.2; 435/7.23; 435/69.1; 435/320.1

(58) Field of Classification Search ............... 536/23.1, 536/23.2; 435/7.23, 69.1, 320.1
See application file for complete search history.

(56) References Cited

U.S. PATENT DOCUMENTS

| | | | |
|---|---|---|---|
| 4,399,216 A | 8/1983 | Axel et al. |
| 4,551,433 A | 11/1985 | DeBoer |
| 4,560,655 A | 12/1985 | Baker |
| 4,657,866 A | 4/1987 | Kumar |
| 4,745,051 A | 5/1988 | Smith et al. |
| 4,767,704 A | 8/1988 | Cleveland et al. |
| 4,777,127 A | 10/1988 | Suni et al. |
| 4,816,567 A | 3/1989 | Cabilly et al. |
| 4,837,148 A | 6/1989 | Cregg |
| 4,889,806 A | 12/1989 | Olson et al. |
| 4,927,762 A | 5/1990 | Darfler |
| 4,929,555 A | 5/1990 | Cregg et al. |
| 4,959,314 A | 9/1990 | Mark et al. |
| 5,013,830 A | 5/1991 | Ohtsuka et al. |
| 5,091,309 A | 2/1992 | Schlesinger et al. |
| 5,149,655 A | 9/1992 | McCabe et al. |
| 5,149,797 A | 9/1992 | Pederson et al. |
| 5,185,440 A | 2/1993 | Davis et al. |
| 5,206,152 A | 4/1993 | Sukhatme |
| 5,217,879 A | 6/1993 | Huang et al. |
| 5,219,740 A | 6/1993 | Miller et al. |
| 5,403,711 A | 4/1995 | Walder et al. |
| 5,422,120 A | 6/1995 | Kim |
| 5,491,133 A | 2/1996 | Walder et al. |
| 5,514,758 A | 5/1996 | Muller et al. |
| 5,530,101 A | 6/1996 | Queen et al. |
| 5,536,821 A | 7/1996 | Agrawal et al. |
| 5,541,306 A | 7/1996 | Agrawal et al. |
| 5,550,111 A | 8/1996 | Suhadolnik et al. |
| 5,563,253 A | 10/1996 | Agrawal et al. |
| 5,565,350 A | 10/1996 | Kmiec |
| 5,565,552 A | 10/1996 | Magda et al. |
| 5,567,810 A | 10/1996 | Weis et al. |
| 5,571,799 A | 11/1996 | Tkachuk et al. |
| 5,574,142 A | 11/1996 | Meyer, Jr. et al. |
| 5,580,859 A | 12/1996 | Felgner et al. |
| 5,585,089 A | 12/1996 | Queen et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,597,696 A | 1/1997 | Linn et al. |
| 5,610,018 A | 3/1997 | Di Fiore et al. |
| 5,625,050 A | 4/1997 | Beaton et al. |
| 5,641,670 A | 6/1997 | Treco et al. |
| 5,652,355 A | 7/1997 | Metelev et al. |
| 5,700,922 A | 12/1997 | Cook |
| 5,776,745 A | 7/1998 | Ketner et al. |
| 5,801,154 A | 9/1998 | Baracchini et al. |
| 5,919,773 A | 7/1999 | Monia et al. |
| 5,939,598 A | 8/1999 | Kucherlapati et al. |
| 5,958,773 A | 9/1999 | Monia et al. |
| 6,333,314 B1 | 12/2001 | Kasid et al. |

FOREIGN PATENT DOCUMENTS

| | | |
|---|---|---|
| EP | 36776 A2 | 9/1981 |
| EP | 0 127 839 A2 | 12/1984 |
| EP | 0 155 476 A1 | 9/1985 |
| EP | 0 244 234 A2 | 11/1987 |
| EP | 0 345 242 A2 | 12/1989 |
| EP | 0 415 731 A2 | 3/1991 |
| EP | 0 524 968 B1 | 2/1993 |
| EP | 1074617 A2 | 2/2001 |
| GB | 2 200 651 A | 8/1988 |
| WO | WO 87/00195 A1 | 1/1987 |
| WO | WO 90/03430 A1 | 4/1990 |
| WO | WO 90/07936 A1 | 7/1990 |
| WO | WO 90/11092 A1 | 10/1990 |

(Continued)

OTHER PUBLICATIONS

Lazar E. et al. Molecular and Cellular Biology 8(3): 1247-1252, 1998.*

(Continued)

*Primary Examiner*—David J. Blanchard
*Assistant Examiner*—Parithosh K. Tungaturthi
(74) *Attorney, Agent, or Firm*—DLA Piper US LLP

(57) ABSTRACT

A gene that is a modulator of tumor growth and metastasis in certain cancer types is provided. SCC-112 (about 150 kDa) and/or a mutant form of SCC-112 (about 65 kDa) is a tumor suppressor molecule. This gene and corresponding polypeptide have diagnostic and therapeutic application for detecting and treating cancers that involve expression of SCC-112 such as breast and kidney cancers.

9 Claims, 24 Drawing Sheets

FOREIGN PATENT DOCUMENTS

Figure 1A:
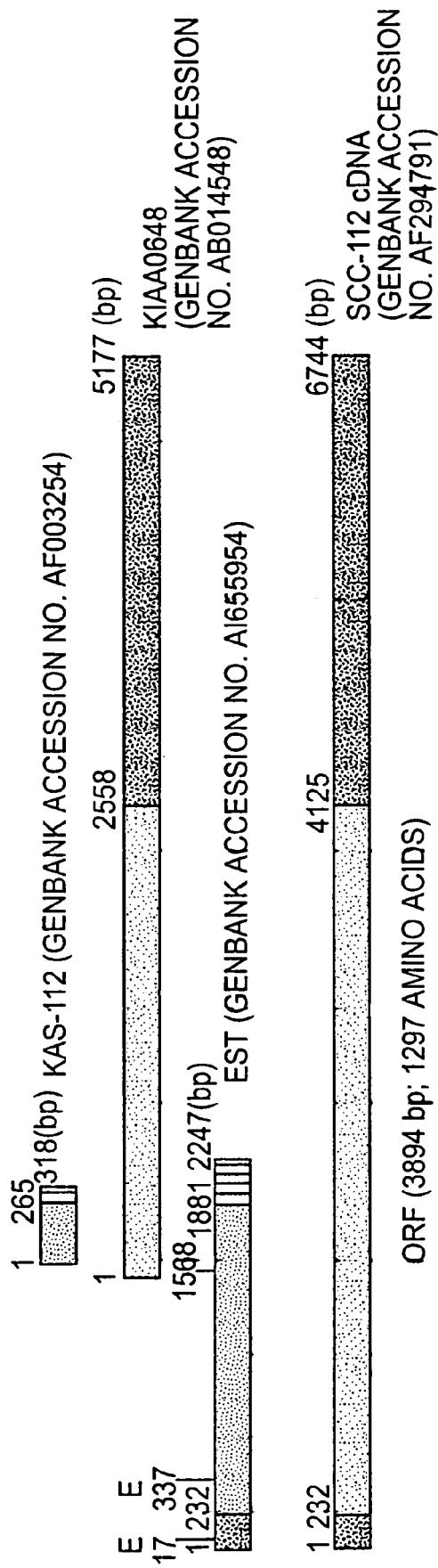

| | | |
|---|---|---|
| WO | WO 91/00357 A1 | 1/1991 |
| WO | WO 91/02805 A2 | 3/1991 |
| WO | WO 91/10741 A1 | 7/1991 |
| WO | WO 91/14445 A1 | 10/1991 |
| WO | WO 92/05266 A2 | 4/1992 |
| WO | WO 92/10578 A1 | 6/1992 |
| WO | WO 92/11033 A1 | 7/1992 |
| WO | WO 93/03769 A1 | 3/1993 |
| WO | WO 93/04170 A1 | 3/1993 |
| WO | WO 93/06248 A1 | 4/1993 |
| WO | WO 93/09239 A1 | 5/1993 |
| WO | WO 93/10218 A1 | 5/1993 |
| WO | WO 93/11230 A1 | 6/1993 |
| WO | WO 93/19191 A1 | 9/1993 |
| WO | WO 93/25234 A1 | 12/1993 |
| WO | WO 93/25698 A1 | 12/1993 |
| WO | WO 94/02602 A1 | 2/1994 |
| WO | WO 94/03622 A1 | 2/1994 |
| WO | WO 94/12649 A2 | 6/1994 |
| WO | WO 94/15645 A1 | 7/1994 |
| WO | WO 94/21792 A2 | 9/1994 |
| WO | WO 94/23697 A1 | 10/1994 |
| WO | WO 94/28938 A1 | 12/1994 |
| WO | WO 95/00655 A1 | 1/1995 |
| WO | WO 95/07994 A2 | 3/1995 |
| WO | WO 95/11984 A2 | 5/1995 |
| WO | WO 95/13796 A1 | 5/1995 |
| WO | WO 95/27044 A1 | 10/1995 |
| WO | WO 95/27069 A1 | 10/1995 |
| WO | WO 95/30763 A2 | 11/1995 |
| WO | WO 96/30498 A1 | 10/1996 |
| WO | WO 96/33735 A1 | 10/1996 |
| WO | WO 96/34096 A1 | 10/1996 |
| WO | WO 98/24893 A2 | 6/1998 |
| WO | WO 00/00157 A2 | 1/2000 |
| WO | WO 02/059337 A1 | 8/2002 |
| WO | WO 02/081639 A2 | 10/2002 |
| WO | WO 02/081640 A2 | 10/2002 |
| WO | WO 02/081641 A2 | 10/2002 |
| WO | WO 02/081642 A2 | 10/2002 |

OTHER PUBLICATIONS

Burgess W.H. et al. Journal of Cell Biology 111: 2129-2138, 1990.*
Ibragimova G.T. et al. Biophysical Journal 77: 2191-2198, 1999.*
Acland et al., Nature. 1990, vol. 343:662-665.*
U.S. Appl. No. 60/264,062, filed Jan. 26, 2001, Kumar et al.
U.S. Appl. No. 60/281,780, filed Apr. 6, 2001, Kasid et al.
U.S. Appl. No. 60/382,031, filed May 22, 2002, Gokhale et al.
U.S. Appl. No. 60/371,126, filed Apr. 10, 2002, Kasid et al.
U.S. Appl. No. 60/281,779, filed Apr. 6, 2001, Kasid et al.
U.S. Appl. No. 60/281,785, filed Apr. 6, 2001, Kasid et al.
U.S. Appl. No. 60/371,116, filed Apr. 10, 2002, Kasid et al.
U.S. Appl. No. 60/281,796, filed Apr. 6, 2001, Kasid et al.
U.S. Appl. No. 10/056,210, filed Jan. 28, 2002, Kasid et al.
U.S. Appl. No. 10/411,931, filed Dec. 4, 2003, Kasid et al.
U.S. Appl. No. 10/411,930, filed Jan. 8, 2004, Kasid et al.
U.S. Appl. No. 10/443,273, filed Dec. 11, 2003, Gokhale et al.
U.S. Appl. No. 10/627,571, filed Apr. 29, 2004, Kasid et al.
U.S. Appl. No. 10/679,561, filed Jun. 3, 2004, Kasid et al.
U.S. Appl. No. 10/679,865, filed Jun. 17, 2004, Kasid et al.
U.S. Appl. No. 10/680,313, filed Aug. 19, 2004, Kasid et al.
Agrawal, Biochimica et Biophysica Acta, 1489(1), 53-68 (1999).
Altschul et al., Nucleic Acids Research, 25(17), 3389-3402 (1997).
Alvarez et al., The Journal of Biological Chemistry, 266(23), 15277-15285 (1991).
Ashkenazi et al., Science, 281(5381), 1305-1308 (1998).
Barba et al., Journal of Neurosurgery, 79(5), 729-734 (1993).
Baccarini et al., The Journal of Biological Chemistry, 266(17), 10941-10945 (1991).
Bain et al., Gene Therapy, 1(S68), (1994).
Ballance et al., Biochemical and Biophysical Research Communications, 112(1), 284-289 (1983).
Barnes et al., Analytical Biochemistry, 102(2), 255 (1980).
Basic and Clinical Immunology, 217-262 (Sites and Terr eds., Appleton & Lange, Norwalk, CT 1991).
Beach et al., Nature, 300(5894), 706-709 (1981).
Belyavsky et al., Nucleic Acids Research 17(8), 2919-2932 (1989).
Berkner, BioTechniques, 6(7), 616-629 (1988).
Berns et al., Annals of The New York Academy of Sciences, 772, 95-104 (1995).
Bertin et al., Proceedings of the National Academy of Sciences of the United States of America, 94(4), 1172-1176 (1997).
Blundell et al., Nature, 326(6111), 347-352 (1987).
Boldin et al., Cell, 85(6), 803-815 (1996).
Boshart et al., Cell, 41(2), 521 (1985).
Bowie et al., Science, 247(4948), 1306-1310 (1990).
Branch et al., Trends in Biochemical Sciences, 23(266), 45-50 (1998).
Bruder et al., Genes & Development, 6(4), 545-556 (1992).
Bruhn et al. Proceedings of the National Academy of Sciences of the United States of America, 89, 2307-2311 (1992).
Buruham et al., American Journal of Hospital Pharmacy 51(2), 210-218 (1994).
Caillaud et al., European Journal of Neuroscience, 5(10), 1287-1291 (1993).
Caplen et al., Proceedings of the National Academy of Sciences of the United States of America, 98(17) 9742-47 (2001).
Carbonell et al., Gene, 73(2), 409-418 (1988).
Carroll et al., The Journal of Biological Chemistry, 266(23) 14964-14969 (1991).
Carprino et al., The Journal of Organic Chemistry, 37, 3404-3409 (1972).
Chang et al., Nature, 275(5681), 617-624 (1978).
Chin, "On the preparation and utilization of isolated and purified oligonucleotides", Katherine R. Everett Law Library of the University of North Carolina, Mar. 2002 (on a CD).
Chinnaiyan et al., The Journal of Biological Chemistry, 271(9) 4961-4965 (1996).
Chiou et al., Virology, 244(1), 108-118 (1998).
Chothia et al., Journal of Molecular Biology, 196(4) 901-917 (1987).
Chung et al., Proceedings of the National Academy of Sciences of the United States of America, 88(11), 4981- (1991).
Cleland et al., Critical Reviews in Therapeutic Drug Carrier Systems, 10(4), 307-377 (1993).
Connelly, Human Gene Therapy, 6(2), 185-193 (1995).
Corpet et al., Nucleic Acids Research., 16(22), 10881-10890 (1988).
Cozens et al., Journal of Molecular Biology, 206(2), 261-280 (1989).
Cregg et al., Molecular and Cellular Biology, 5(12), 3376-3385 (1985).
Crooke, Biochimica et Biophysica Acta, 1489(1) 31-44 (1999).
Cunningham et al., Science, 244(108), 1081-1085 (1989).
Curiel et al., Human Gene Therapy, 3(2), 147-154 (1992).
Darzynkiewicz et al., Cytometry, 13(8), 795-808 (1992).
Das et al., Journal of Bacteriology, 158(3), 1165-1167 (1984).
Davidow et al., Current Genetics, 10(1), 39-48 (1985).
Davis, The New Biologist, 2(5), 410-419 (1990).
Davis et al., Enzyme Engineering, 4, 169-73 (1978).
Dayhoff et al., Atlas of Protein Sequence and Structure, 5(Supplement 3), 345-352 (1978).
De Bohr et al., Proceedings of the National Academy of Sciences of the United States of America, 80(1), 21-25 (1983).
De Louvencourt et al., Journal of Bacteriology, 154(2), 737-742 (1983).
Dent et al., Science, 257(5075), 1404-1407 (1992).
Devary et al., Cell, 71, 1081-1091 (1992).
De Vos et al., Science, 255(5042), 306-312 (1992).
Dijkema et al., The EMBO Journal, 4(3), 761 (1985).
Dinchuk et al., The Journal of Biological Chemistry, 275(50), 39543-39554 (2000).
Downing et al., Cell, 85(4), 597-605 (1996).

Earl et al., *Proceedings of the National Academy of Sciences of the United States of America*, 83(11), 3659-3663 (1986).
Elbashir et al., *Nature*, 411(6836), 494-98 (2001).
Fabian et al., *Molecular and Cellular Biology*, 13(11), 7170 (1993).
Federoff et al., *Proceedings of the National Academy of Sciences of the United States of America*, 89(5), 1636-40 (1992).
Felger et al., *Human Gene Therapy*, 7(15), 1791-1793 (1996).
Fiermonte et al, *The Journal of Biological Chemistry*, 276(11), 8225-8230 (2001).
Finco et al., *The Journal of Biological Chemistry*, 268(24), 17676-17679 (1993).
Fink et al., *Annual Review of Neuroscience*, 19, 265-87 (1992).
Flotte et al., *Proceedings of the National Academy of Sciences of the United States of America*, 90(22), 10613-10617 (1993).
Friden et al., *Science*, 259, 373-377 (1993).
Friesen et al., *The Molecular Biology of Baculoviruses*, 31-49 (1986).
Gaillardin et al., *Current Genetics*, 10, 49-58 (1985).
Galfre et al., *Methods in Enzymology; Immunochemical Techniques*, 73, 3-46 (1981).
Gardner et al., *The Journal of Biological Chemistry*, 268(24) 1789617901(1993).
Gille et al., *Nature*, 258(6385), 414-417 (1992).
Gleeson et al., *The Journal of General Microbiology*, 132(12), 3459-3465 (1986).
Goeddel et al., *Nature*, 281(5732), 544 (1979).
Goeddel et al., *Nucleic Acids Research*, 8(18), 4057-4074 (1980).
Gokhale et al., *Gene Therapy*, 4(12), 1289-1299 (1997).
Gokhale et al., *Antisense & Nucleic Acid Drug Development*, 9(2), 191-201 (1999).
Goltsev et al., *The Journal of Biological Chemistry*, 272(32), 19641-19644 (1997).
Gonzalez et al., *Current Opinion in Biotechnology*, 9(6), 624-631 (1998).
Gorman et al., *Proceedings of the National Academy of Sciences of the United States of America*, 79(22), 6777-6781 (1982).
Goruppi et al., *FEBS Letters*, 415(1), 59-63 (1997).
Green et al., *Science*, 281(5381), 1309-1312 (1998).
Griffith et al., *The Journal of Immunology*, 161(6), 2833-2840 (1998).
Guzman et al., *Circulation Research*, 73(6), 1202-1207 (1993).
Guzman et al., *Circulation*, 88(6), 2838-2848 (1993).
Ham et al., *Methods in Enzymology*, 58, 44-93 (1979).
Han et al., *American Journal of Respiratory Cell and Molecular Biology*, 11(3), 270-278 (1994).
Heidecker et al., *Molecular and Cellular Biology*, 10(6), 2503-2512 (1990).
Heidecker et al., *Advances in Cancer Research*, 58, 53-73 (1992).
Heo et al., *Cancer Research*, 49(18), 5167-5175 (1989).
Higgins et al., *Computer Applications in the Biosciences*, 8(2), 189-191 (1992).
Hinnen et al., *Proceedings of the National Academy of Sciences*, 75(4), 1929-1933 (1978).
Horrevoets et al., *Blood*, 93(10), 3418-3431 (1999).
Houldworth et al., *Proceedings of the National Academy of Sciences of the United States of America*, 85(1), 377-381 (1988).
Howe et al., *Cell*, 71(2), 335-342 (1992).
Hu et al., *Virology*, 227(2), 295-304 (1997).
Hu et al., *The Journal of Biological Chemistry*, 272(15), 9621-9624 (1997).
Hu et al., *The Journal of Biological Chemistry*, 272(28), 17255-17257 (1997).
Inbal et al., *Nature*, 390(6656), 180-184 (1997).
Irmier et al., *Nature*, 388(6638), 190-195 (1997).
Ito et al., *Journal of Bacteriology*, 153(1), 163-168 (1983).
Jaffe et al., *Nature Genetics*, 1(5), 372-378 (1992).
Jolly, *Cancer Gene Therapy*, 1(1), 51-64 (1994).
Jones et al., *Nature*, 321(6069), 522-525 (1986).
Kaplitt, *Nature Genetics*, 8(2), 148-154 (1994).
Kasid et al., *Science*, 238(4818), 1039-1041 (1987).
Kasid et al., *Science*, 243(4896), 1354-1356 (1989).
Kasid et al., *Advances in Cancer Research*, 61, 195-233 (1993).
Kasid et al., *Nature*, 382(6594), 813-816 (1996).
Kasid et al., *Molecular and Cellular Biochemistry*, 173(1&2), 193-197 (1997).
Kasid et al., *Apoptosis Genes*, Kluwer Academic Publishers, MA (eds. Potten, Booth, & Wilson), 85-118 (1998).
Kass-Bisler et al., *Proceedings of the National Academy of Sciences of the United States of America*, 90(24), 11498-11502 (1993).
Kataoka et al., *The Journal of Immunology*, 161(8), 3936-3942 (1998).
Kelly et al., *The EMBO Journal*, 4(2), 475-479 (1985).
Kelson et al., *Biochimica Et Biophysica Acta*, 1335(1-2), 99-110 (1997).
Kettleborough et al., *Protein Engineering.*, 4(7), 773-83 (1991).
Kimura, *Human Gene Therapy*, 5(7), 845-852 (1994).
Kissil et al., *The EMBO Journal*, 18(2), 353-362 (1999).
Kizaka-Kondoh et al., *Molecular and Cellular Biology*, 12(11), 5078-5086 (1992).
Koide et al., *Proceedings of the National Academy of Sciences of the United States of America*, 90(18), 8683 (1993).
Kolarov et al., *The Journal of Biological Chemistry*, 265(21), 12711-12716 (1990).
Kolch et al., *Nature*, 349(6308), 426-428 (1991).
Kolls et al., *Proceedings of the National Academy of Sciences of the United States of America*, 91(1), 9215-219 (1994).
Korioth et al., *Gene*, 150(2), 395-399 (1994).
Krug et al., *Methods in Enzymology; Guide to Molecular Cloning Techniques*, 152, 316-325 (1987).
Kumar et al., *The Journal of Biological Chemistry*, 275(4) 2973-2978 (2000).
Kunze et al., *Journal of Basic Microbiology*, 25(2), 141-144 (1985).
Kurtz et al., *Molecular and Cellular Biology*, 6(1), 142 (1986).
Kyriakis et al., *Nature*, 358(6385), 417-421 (1992).
Lawson et al., *The Journal of Biological Chemistry*, 263(29), 14812-14818 (1988).
Lebacq-Verheyden et al., *Molecular and Cellualr Biology*, 8(8), 3129 (1988).
Lee et al., *The Journal of Biological Chemistry*, 266(16), 10351-10357 (1991).
Lennon et al., *Genomics*, 33(1), 151-152 (1996).
Levero et al., *Gene*, 101(2), 195-202 (1991).
Li et al., *Human Gene Therapy*, 4(4), 403-409 (1993).
Li et al., *Proceedings of the National Academy of Sciences*, 90(20), 9247-9251 (1993).
Liang et al., *Science*, 257(5072), 967-971 (1992).
Lim et al., *Gene*, 255, 35-42 (2000).
Luciakova et al., *Biochemical Journal*, 352(2), 519-523 (2000).
Luckow et al., *Bio/Technology*, 6(1), 47-55 (1988).
Macdonald et al., *Molecular and Cellular Biology*, 13(11), 6615-6620 (1993).
Maeda et al., *Nature*, 315(6020), 592-594 (1985).
Marshall et al., *Cell*, 80(2), 179-185 (1995).
Martens et al., *Analytical Biochemistry*, 273(1), 20-31 (1999).
Martin et al., *DNA*, 7(2), 99-106 (1988).
Marzo et al., *The Journal of Experimental Medicine*, 187(8), 1261-1271 (1998).
Mendelson et al., *Virology*, 166, 154-165 (1988).
Merrifield et al., *Journal of the American Chemical Society*, 85, 2149-2154 (1963).
Miller et al., *Genetic Engineering*, 8, 277-279 (1986) (Setlow et al. ed.).
Miller, *Annual Review of Microbiology*, 42, 1777-199 (1988).
Milner et al., *Nature Biotechnology*, 15, 537-541 (1997).
Milstein et al., *Nature*, 256(5517), 495-497 (1975).
Miyajima et al., *Gene*, 58(2&3), 273-281 (1987).
Monia et al., *Nature Medicine*, 2(6), 668-675 (1996).
Morimoto et al., *The Journal of Immunology*, 147(8), 2609-2616 (1991).
Morrison et al., *The Journal of Biological Chemistry*, 268(23), 17309-17316 (1993).
Morrison et al., *Proceedings of the National Academy of Sciences of the United States of America*, 81(21), 6851-6855 (1984).
Morrison et al., *Advances in Immunology*, 44, 65-92 (1988).
Muzio et al., *Cell*, 85(6), 817-827 (1996).
Nakai et al., *Genomics*, 14, 897-911 (1992).

Nakamura et al., *The Journal of Biological Chemistry*, 274(32), 22476-22483 (1999).
Neckelmann et al., *Proceedings of the National Academy of Sciences of the United States of America*, 84(21), 7580-7584 (1987).
Nicoletti et al., *Journal of Immunological Methods*, 139(2), 271-279 (1991).
Oda et al., *Biochemical and Biophysical Research Communications*, 193(3), 897-904 (1993).
Ohmichi et al., *The Journal of Biological Chemistry*, 267(21), 14604-14610 (1992).
Ostade et al., *Nature*, 361(6409), 266-269 (1993).
Padlan et al., *Molecular Immunology*, 28(4/5), 489-498 (1991).
Padlan et al., *Molecular Immunology*, 31(3), 169-217 (1994).
Patel et al., *Molecular Carcinogenesis*, 18(1), 1-6 (1997).
Patel et al., *Oral Oncology*, 33(3), 197-203 (1997).
Patel et al., *Molecular Medicine*, 3(10), 674-685 (1997).
Patel et al., *ACTA Oncological*, 37(5), 475-478 (1998).
Pfeifer et al., *Proceedings of the National Academy of Sciences of the United States of America*, 86(24), 10075-10079 (1989).
Pfeifer et al., *Biochemical and Biophysical Research Communications*, 252(1), 481-486 (1998).
Philip, *Molecular and Cellular Biology*, 14(4), 2411-2418 (1994).
Pinckard et al., *Clinical and Experimental Immunology*, 2, 331-340 (1967).
Prasad et al., *Molecular and Cellular Biology*, 12(11), 5260-5267 (1992).
Pulverer et al., *Nature*, 353(6345), 670 (1991).
Qureshi et al., *The Journal of Biological Chemistry*, 266(31), 20594-20597 (1991).
Ram et al., *Cancer Research*, 53(1), 83-88 (1993).
Rapp et al, *The Oncogene Handbook*, (Elsevier Science Publishers, New York), 213-253 (1988).
Rapp, *Oncogene*, 6(4), 495-500 (1991).
Rebay et al., *Cell*, 67, 687-699 (1991).
Rees et al., *The EMBO Journal*, 7(7), 2053-2061 (1988).
Riedel et al., *European Journal of Immunology*, 12, 3146-3150 (1993).
Robbins et al., *Diabetes*, 36(7), 838-845 (1987).
Rogers et al., *Genomics*, 39(2), 127-135 (1997).
Roggenkamp et al., *Molecular & General Genetics*, 202(2), 302-308 (1986).
Rosenfeld et al., *Science*, 252(5004), 431-434 (1991).
Sacchi et al., *Archives of Otolaryngology-Head & Neck Surgery*, 117(3), 321-326 (1991).
Samuels et al., *Molecular and Cellular Biology*, 13(10), 6241-6252 (1993).
Samulski et al., *Journal of Virology*, 63(9), 3822-3828 (1989).
Sarubbi et al., *Analytical Biochemistry*, 237(1), 70-75 (1996).
Sata et al., *The Journal of Biological Chemistry*, 273(50), 33103-33106 (1998).
Schaap et al., *The Journal of Biological Chemistry*, 268(27), 20232-20236 (1993).
Schneider et al., *Tetrahedron Letters*, 31(3), 335-338 (1990).
Seth et al., *The Journal of Biological Chemistry*, 266(35), 23521 (1991).
Siebenlist et al., *Cell*, 20(1), 269 (1980).
Siegel et al., *The Journal of Immunology*, 151(8), 4116-4127 (1993).
Smith et al., *Proceedings of the National Academy of Sciences of the United States of America*, 82(24), 8404-8408 (1985).
Smith et al., *Journal of Molecular Biology*, 224(4), 899-904 (1992).
Smith et al., *Advances in Applied Mathematics*, 2(4), 482-489 (1981).
Soldatenkov et al., *The Cancer Journal from Scientific American*, 3(1), 13-20 (1997).
Sozeri et al., *Oncogene*, 7(11), 2259 (1992).
Srinivasula et al., *The Journal of Biological Chemistry*, 272(30), 18542-18545 (1997).
Stanton et al., *Molecular and Cellular Biology*, 9(2), 639-647 (1989).
Stein, *Biochimica et Biophysica Acta*, 1489(1), 45-52 (1999).
Stenflo, *Blood*, 78(7). 1637-1651 (1991).
Stokoe et al., *The EMBO Journal*, 11(11), 3985-3994 (1992).
Sturgill et al., *Nature*, 334(6184), 715-718 (1988).
Sun et al., *Hepatology*, 27(1), 228-239 (1998).
Sunnerhagen et al., *The Journal of Biological Chemistry*, 268(31), 2339-2344 (1993).
Suy et al., *Oncogene*, 15(1), 53-61 (1997).
Suy et al., *The Journal of Biological Chemistry*, 273(28), 1787117878 (1998).
Takamiya et al., *Journal of Neuroscience Research*, 33(3), 493-503 (1992).
Tewari et al., *The Journal of Biological Chemistry*, 270(39), 22705-22708 (1995).
Thome et al., *Nature*, 386(6624), 517-521 (1997).
Tilburn et al., *Gene*, 26(2&3), 205-221 (1983).
Tornkvist et al., *The Journal of Biological Chemistry*, 269(19), 13919-13921 (1994).
Traverse et al., *Oncogene*, 8(11), 3175-3181 (1993).
Troppmair et al., *Mechanisms in B-Cell Neoplasia 1992*, 453-460 (1992).
Turner et al., *Proceedings of the National Academy of Sciences of the United States of America*, 90(12), 5544-5548 (1993).
Uhlmann et al., *Chemical Reviews*, 90(4), 543-584 (1990).
Van Den Berg et al., *Bio/Technology*, 8(2), 135139 (1990).
Verhoeyer et al., *Science*, 239(4847), 1534-1536 (1988).
Vile et al., *Cancer Research.*, 53(5), 962-967 (1993).
Vile et al., *Cancer Research*, 53(17), 3860-3864 (1993).
Vincent et al., *Nature Genetics*, 5, 130-134 (1993).
Vlak et al., *Journal of General Virology*, 69(4) 765-776 (1988).
Wang et al., *Cell*, 87(4), 629-638 (1996).
Warne et al., *Nature*, 364(6435), 352-355 (1993).
Weiss et al., *Journal of the National Cancer Institute*, 23, 51-54 (1998).
Welling et al., *FEBS Letters*, 188(2), 215-218 (1985).
Winitz et al., *The Journal of Biological Chemistry*, 268(26), 19196-19199 (1993).
Woffendin, *Proceedings of the National Academy of Sciences of the United States of America*, 91(24), 11581-11585 (1994).
Wotten et al., *The Journal of Biological Chemistry*, 268(24), 17975-17982 (1993).
Wu, *The Journal of Biological Chemistry*, 264(29), 16985-16987 (1989).
Yeh et al., *The Journal of Experimental Medicine*, 188(10), 1795-1802 (1998).
Yelton et al., *Proceedings of the National Academy of Sciences of the United States of America*, 81(5), 1470-1474 (1984).
Zabner et al., *Cell*, 75(2), 207-216 (1993).
Zhang et al., *Nature*, 364(6435), 308-313 (1993).
GenBank, Accession No. AB014548, "*Homo sapiens* mRNA for KIAA0648 protein, partial cds, " ver. AB014548.1 GI:3327109 (1999).
GenBank, Accession No. AF003254, "*Homo sapiens* PCI-O6A; head and neck squamous cell carcinoma," ver. AF003254 GI: 21973638 (2002).
GenBank, Accession No. AF294791, "*Homo sapiens* SCC-112 (SCC-112) mRNA, complete cds.," ver. AF294791.1 GI: 21951801 (2002).
GenBank, Accession No. AI655954, ver. AI655954 GI: 4739933 (1999).
Sambrook et al., *Cold Spring Harbor Press*, 16.3-16.3 (1989).

* cited by examiner

FIG. 1B

```
       S  W  I  K  D  K  L  L  H  I  Y  Y  Q  N  S  I  D  D  K  L  L  V  E  K  I  F  A  Q  Y  L  V  P  H  N  L  E  T  E  E  R
404    atgaaatgcttatattacttactatatgcagtttggatcaaatgctcaacgaagtctgtaaaagctgtaaaagctctcaacgaagtctcaagacgtcgaagaacatgcagaactgctcgaactattgattgcac    1680
       M  K  C  L  Y  Y  L  Y  A  S  L  D  P  N  A  V  K  A  L  N  E  M  W  K  C  Q  N  M  L  R  S  H  V  R  E  L  L  D  L  H
444    aagcagcctacacatcaggagctaactgttctgttctgccatgtttggaaaactgatgacaagcatagcaacctgattgcttccaaccagaatttgaagcacacaagattttgtgaggaacacaagattttaaccaggttctc   1800
       K  Q  P  T  S  E  A  N  C  S  A  M  F  G  K  L  M  T  I  A  K  N  L  P  D  P  G  K  A  Q  D  F  V  K  K  F  N  Q  V  L
484    ggcgatgatgagaacttcgtctgagtggagttattaattagccacagcctgtctcttgcaacaagcagatatttgtgaggagaaatgacccggaacttgcaaatctaagcaacca    1920
       G  D  D  E  K  L  R  S  Q  L  E  L  L  I  S  P  T  C  S  K  Q  A  D  I  C  V  R  E  I  A  R  K  L  A  N  P  K  Q  P
524    acaaatccttttctagagatggtcaaattctgttgaaagaatcgcactgtcagaaggccataagtgcactagtgaaattgatgataagtcaatagagggacagca    2040
       T  N  P  F  L  E  M  V  R  K  F  L  L  E  R  I  A  P  V  H  I  D  S  E  A  I  S  A  L  V  K  L  M  N  K  S  I  E  G  T  A
564    gatgatgaagaggagggtgtaagtccagatacagctatccgttcaggactgtcattcaaatttttagaaatacaggtcacaaatacagaccttcccagatacgatcgacctaattcccatt    2160
       D  D  E  E  G  V  S  P  D  T  A  I  R  S  G  L  E  L  L  K  V  L  S  F  T  H  P  T  S  F  H  S  A  E  T  Y  E  S  L
604    ttacagtgcctaagaatgctgaggatgacaagtgctattcaaattttagaaatacaggtcacaaatacagaccttcccagatacgatcgacctaattcccatt    2280
       L  Q  C  L  R  M  E  D  D  K  V  A  E  A  A  I  Q  I  F  R  N  T  G  H  K  I  E  T  D  L  P  Q  I  R  S  T  L  I  P  I
644    ttacatcaaaagcaagagggtactccacaccaagcaaaacaggctgtgcactgtatacacggccatattcaacaataaagagtccattgcacagatttttgacgactcagtagg    2400
       L  H  Q  K  A  K  R  G  T  P  H  Q  A  K  Q  A  V  H  C  I  H  A  I  F  T  N  K  E  V  L  A  Q  I  F  E  P  L  S  R
684    agtctgaatgctgatgtgccagaacaactatactctcattggccacttctatgttaggaccagatcagttgcttcccatgaaatcagttagtagcaaatttatt    2520
       S  L  N  A  D  V  P  E  Q  L  I  T  P  L  V  S  L  G  H  I  S  M  L  A  P  D  Q  F  A  S  P  M  K  S  V  V  A  N  F  I
744    gtgaaagatctgctaatgaatgacaggtcaacaggtgaaaagaatggaaaactgtggtctccagatgaagaggtttccctgaagtactgagcaaggtacaggcaattaacttctggta    2640
       V  K  D  L  L  M  N  D  R  S  T  G  E  K  N  G  K  L  W  S  P  D  E  E  V  S  P  E  V  L  A  K  V  Q  A  I  K  L  L  V
764    agtggctgtttgggtatgaaaaacaaccagtctaaatctgccaattcaaccctcggttattatcagcgatgttggtagtgaggggtgacctgacagagaacagaaaaggatcagtaaatct    2760
       R  W  L  G  M  K  N  N  Q  S  K  S  A  N  S  T  L  R  L  L  S  A  M  L  V  S  E  G  D  L  T  E  Q  K  R  I  S  K  S
804    gatatgtctcgcttgcgattagctgctgtagtgccataatgaagctttgctcaggaacctgctcagctctgctgcactgcactgttcagttactgttaattaatgat    2880
       D  M  S  R  L  R  L  A  A  G  S  A  I  M  K E A Q P C  H  E  I  I  T  P  E  Q  F  Q  L  C  A  L  V  I  N  D
844
```

*FIG. 1B CONT.-1*

```
       ggtgttaccaagtaaggcagatattgctcagaagctgcataaggcactgtgaagttactgctcccattggatatggcgatctttgcttgtgccaaagatcctgtgaaggag    3000
       E  C  Y  Q  V  R  Q  I  F  A  Q  K  L  H  K  A  L  V  K  L  L  L  P  L  E  Y  M  A  I  F  A  L  C  A  K  D  P  V  K  E
       agaagcacacgccacgacaatgttactgaaaatatcagtattcgcagggaatacattaagcagatcctactgaagatttgcctgattcactgttgctgaatatgtagttca    3120
       R  R  S  H  A  R  Q  C  L  L  K  N  I  S  I  R  R  E  Y  I  K  Q  N  P  M  A  T  E  K  L  L  S  L  L  P  E  Y  V  V  P
       tacatgattcacctgctagccatgaccctatccagattttacaagatcacaagatgttgatcagctcgacttcgtgatatccagatgccatgcctatgttaatgacaagaatgaa    3240
       Y  M  I  H  L  A  H  D  P  D  F  T  R  S  Q  D  V  D  Q  L  R  D  I  K  E  C  L  W  F  M  L  E  V  L  M  T  K  N  E
       aacaatagccatgccttatgaagaagatgcgagagaacatcaagttaaccagatgcccagtcctcaagatgaatccagatgaatccaagacaaatgtatacagtatgtgatggctctc    3360
       N  N  S  H  A  F  M  K  K  M  A  E  N  I  K  L  T  R  D  A  Q  S  P  D  E  S  K  L  N  E  K  L  Y  T  V  C  D  V  A  L
       tgtgttataaatagtaaaagtgcttgtgcaatgcagattcaccaaggaccagttcctccccaatgaaatttttacacaaccgaaaaggacttctgtaacgatagagttatattca    3480
       C  V  I  N  S  K  S  A  L  C  N  A  D  S  P  K  D  P  V  L  P  M  K  F  F  T  Q  P  E  D  K  F  C  N  D  K  S  Y  I  S
       gaagagacaagatactctgttaacaggaaagccaaagctgaacctgaaccttcaccggaagttcaggagtgcagtaataagcttatcagcaacggacagagttgaagctgactgag    3600
       E  E  T  R  V  L  L  T  G  K  P  K  P  A  G  V  L  G  A  V  N  K  P  L  S  A  T  G  R  K  P  Y  V  R  S  T  G  T  E
       actggaagcaatattaatgtaaattcagagaatctgtaacctgaaagcagtaaagtaaggaatcagaggaattaattctgatcaggcaccatcagcagtgcaacatcagcggaccaa    3720
       T  G  S  N  I  N  V  N  S  E  L  N  P  S  T  G  N  R  S  R  E  Q  S  S  E  A  A  E  T  G  V  S  E  N  E  E  N  P  V  R
       attatttcagtcactgcagagaatatccaacaaacaagatgaatggagaaagtagtaggaaagtagaaaaaacggaaccggaccagtgtcgaccagtcaatgctacc    3840
       I  I  S  V  T  P  V  K  N  I  D  P  V  K  N  K  E  I  N  S  D  Q  A  T  Q  G  N  I  S  S  D  R  G  K  K  R  T  V  T  A
       gctggtgcagaatccaacaacaagatgatggaaagtagtagaaaagtgcattgcaaaggagtaaatgaaggagaaaatgaaggcaaaacaagagagagcaggcccaaacagcaaagctgctgcccagctgataagctacc    3960
       A  G  A  E  N  I  Q  Q  K  T  D  E  K  V  D  E  S  G  P  P  A  P  S  K  F  R  R  G  R  R  K  S  E  S  O  G  N  A  T
       aaaaatgatgataacttaaccattactaaaggacaattgactacaaagtaaaattgcttcgaaaaggaagaaaatgaaggcaaagcaacgaggaagccaggctcctcagctcctgcaaaaacttgattagcc    4080
       K  N  D  D  L  N  K  P  I  N  K  G  R  K  R  A  A  V  G  Q  E  S  P  G  G  L  E  A  G  N  A  K  A  P  K  L  Q  D  L  A
       aaaaggcagcagcagcagacaaagtcatttgactaagaatgcattgcaaaaggagaaaatgaagcaaacagaagaagcaggcctgcaacacaatctctgcaaaacttgattcaca    4200
       K  K  A  A  P  A  E  R  Q  I  D  L  Q  R  *      SEQ ID NO:2
       aatgtccctgacagcagagaaaatgaagctcagaaacacctttgcttgaaactctgaaacaaggaagaagactattactcctttcacatgaccagtcctgatgaaatgtacagcag    4320
       aactcttgagagagaggtctaaaagctaaagcaactctgtctccccctagactttcttacgaaagtcaataattgcttaacaacttgttccagttcctgttcctgcctatctgg    4440
```

*FIG. 1B CONT.-2*

```
agtttaatgcgtaatacaccattaattccacgctgcagttttatttaaagaagtaacagatgtctttacactgcactgaaaatcatccatttagagcaggaattcatccatg   4560
ttacacaggaaaaaatagaagtctactgaattaatttttaaagaaagagattcagattaaatattttcttgttttccttttgaaacttttatgtataatcttctgctgctac   4680
tttctgcaaaaatgagatgtacagatttcgttccctgcatgaaagtgatgtgtagcaattgatgtttctgatttatcagatgagaaattaaaattattgatt           4800
tgcaagtagtaaacagttcatatttgattccctcatttagtttaatatttgcaataaatgtacatattgtttgttgtttcataaagcatatcacttaaaatggttttactc   4920
ctgattatgttggaatatttggaattttaaaggagtaagactgtccagcattggttttgtcaccagatttttattaatgtaaaaatcaattttaaaaaatagttg        5040
gactttgcagctttaaggaaagttggagtgtttagattgctatcaatttcagcattgtgcctatttgaaataagtgtttgtttgtctgatgtgtcttggctcatttttatgt   5160
ttattttagaaaactgttgcatcaatatattatgtttcttgcattgttcagcataagtaatgtgcactttatgtgtacacataatcatatttaagttttgcataaaatgct   5280
tctagatgtcatgcagtctcttttatcatttttatcatatgtcttcttgtgaattttcatgtaaagagctaaagtcataaacgatcagtacgtcactcctccattatcatataaat   5400
agtgactaagcctcaggttttaatttgtgataacaaaatacgaaggcatgtaagacctgattctggaggaacatgaaatttgtcttcctcatgtccagattctatcctgcccca   5520
ctgtccactgtagggtcatccgcaaagcctagcagaatgtgctcactccatttcttacacgttcctgtagagtgaagtttgagagtaaatgtcacttacgttttcatagatgatcaagagttggctgtgtat   5640
gtagtgtacatggatgtaaaacaacagtgtatcaaagtggataattcaaagtggataattcaaagatgatactccttttacaggggcagaaaat                  5760
tgactgaaagatggtaattatttaaatagtgcattacacacatttagtgtatcagaagatgatcaatgataccaagtaatgatacctttacagggcagaaaat        5880
cccactcttccttattgcctcttcagaaccctttagaagttctcttcagatctgctccaacatgtgaaaagagtatctatgcataagtacagaagtccctcaagcaatcagtagg   6000
tgttctatttagagagagtttaagtttcatcagacagacaacttgattcctaagttcagtgtgtcaccaacaaaagtgcattgataggaccttgtctcttcctcccttt      6120
gattaattgccgatcacagttactacagattaccaagtgttacatcatattaaataaaatgcaagtgtctgcactaaggaagcaagagtaggttggaaagaccaagctgatgggaggga   6240
aaaggattgtcttcctgtatgatgtaagtggccaccccaattgtaacatgtcaagtgtctgcactaaggaagcaagagtaggttggaaagaccaagctgatgggaggga   6360
cttgttacgggaatttttagtttcctttcaaaggaaacattaaaatccttaggaattgtattcacatctccagagaactcagagaactacacacaaagtgcagactatatttgagaat   6480
taatgtaaccctttgtgctcagttgaagcttctgtatttgtctaaaacaacaagccagaatttgtatctccttgataaaagtgtataatgtaaagtagtttgcatatctt   6600
gtgctgcacatggctgaatgggcagatttttaaatttttaaaacctgaatttgtaattgtgtaaatgacaagtgtaaaatcctaccaagtgtaaaatgctaaaaatgcactgttttca   6720
aataaaccaagaatgcagcatt SEQ ID NO:1                                                                           6744
```

*FIG. 1B CONT.-3*

Figure 2:
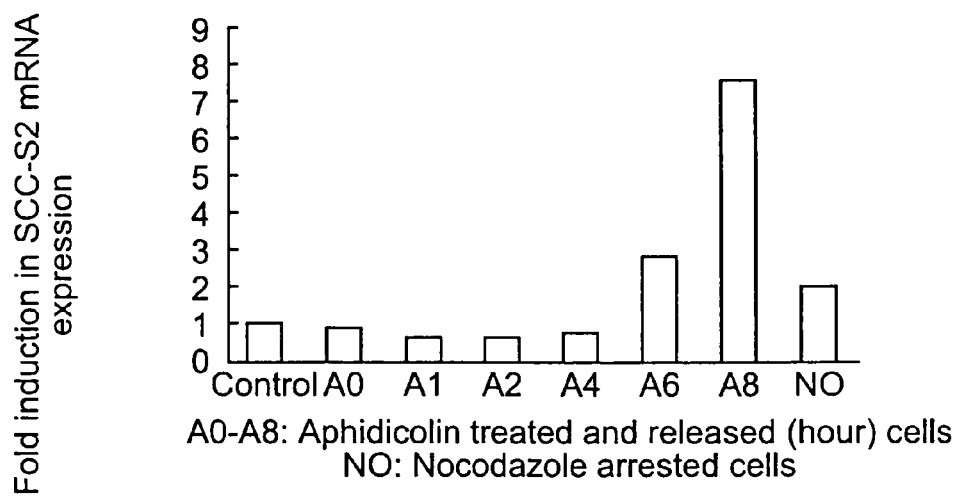
Figure 2:
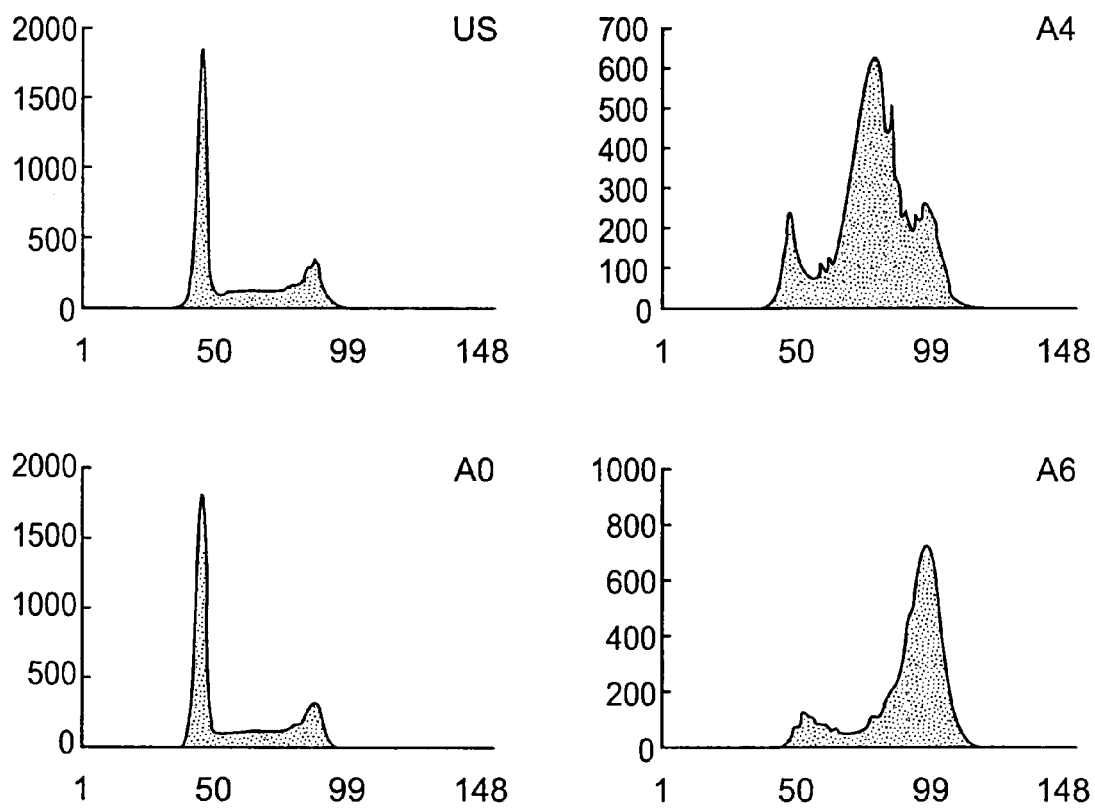
Figure 2:
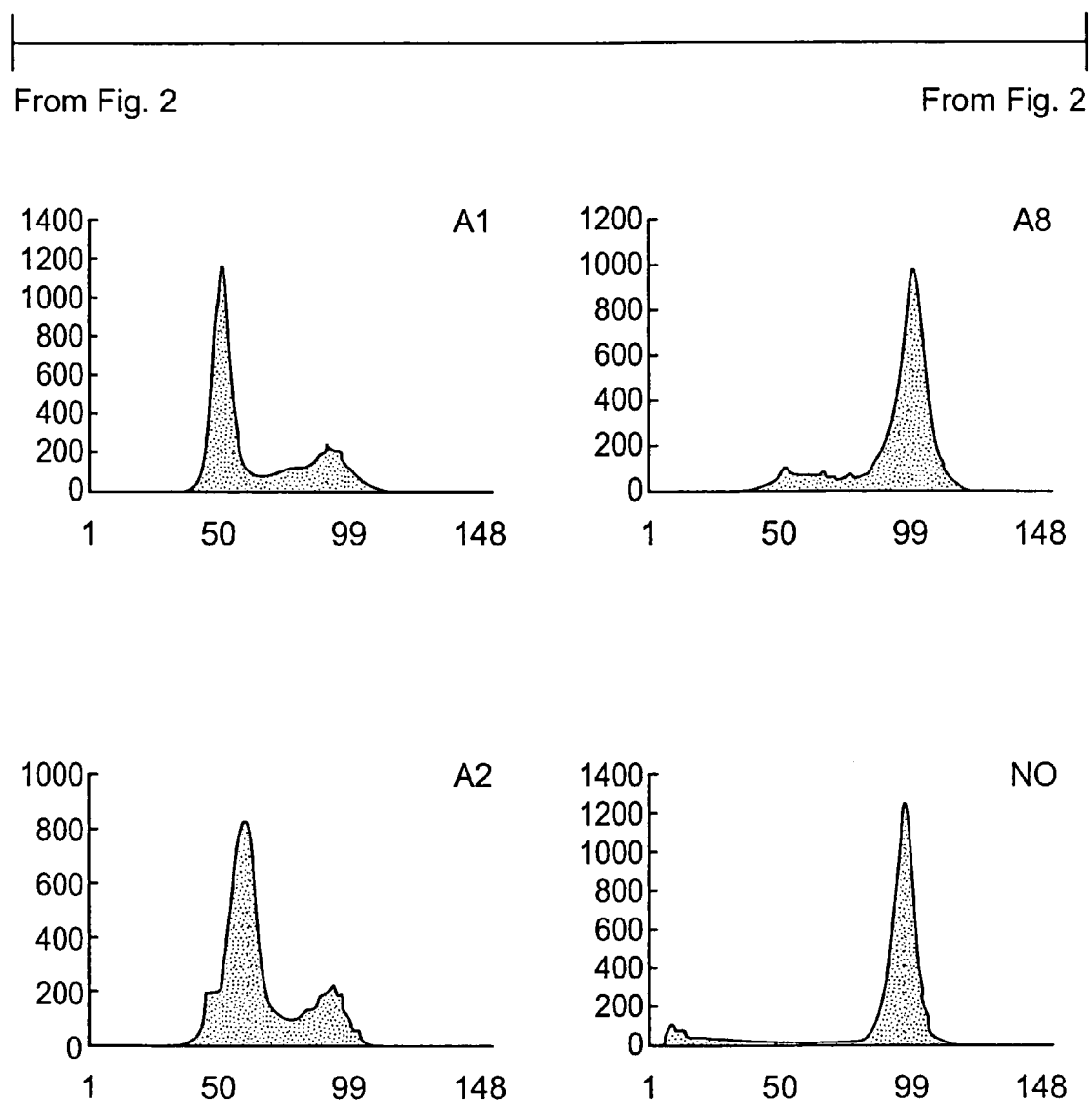

To Fig. 2 Cont.                                          To Fig. 2 Cont.

Figure 7C:
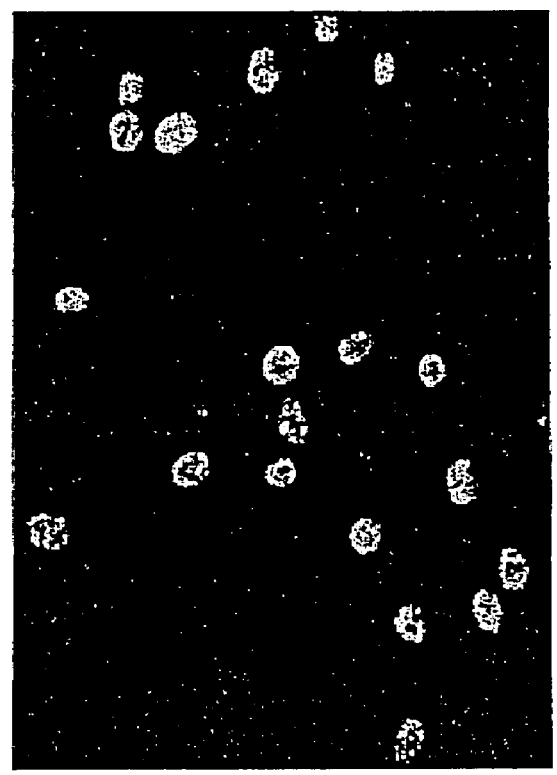

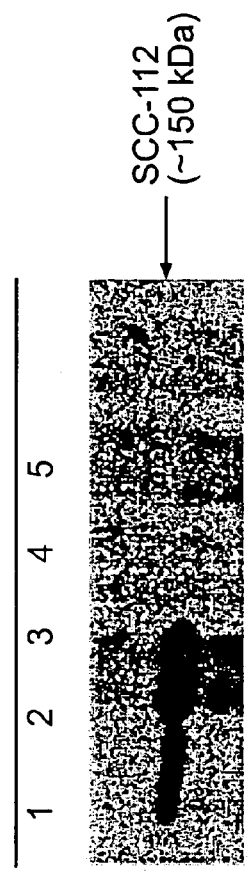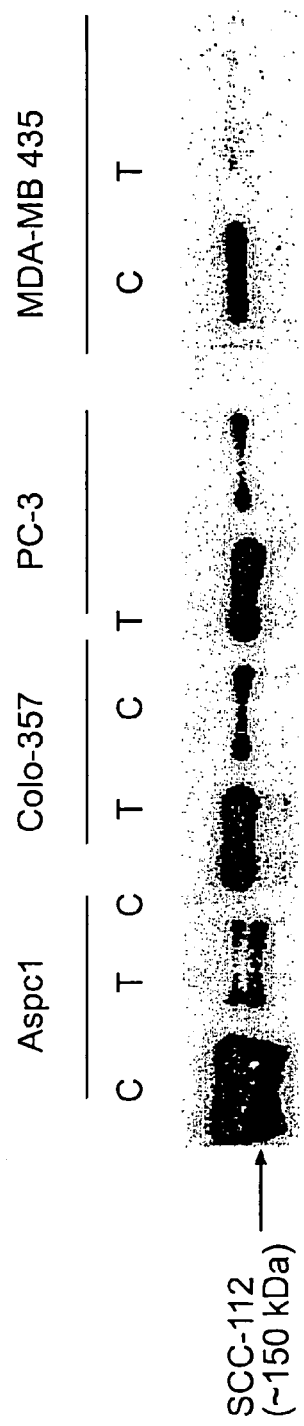
FIG. 7A
FIG. 7B

DAPI

ANTI-SCC-112 ANTIBODY

| TUMOR TYPE | NUMBER OF PATIENTS (n) | MEAN N/T* (LOGRATIO) | MEAN N/T* (RATIO) | STANDARD ERROR (LOGRATIO) | 95% CONFIDENCE INTERVAL (LOGRATIO) | 95% CONFIDENCE INTERVAL (RATIO) | P VALUE (TWO-SIDED) |
|---|---|---|---|---|---|---|---|
| KIDNEY | 20 | 0.20 | 1.22 | 0.03 | (0.13, 0.26) | (1.14, 1.30) | <0.0001 |
| BREAST | 50 | 0.20 | 1.22 | 0.05 | (0.10, 0.29) | (1.11, 1.34) | <0.0001 |
| RECTUM | 18 | 0.11 | 1.11 | 0.07 | (-0.04, 0.25) | (0.96, 1.25) | 0.13 |
| THYROID | 6 | 0.10 | 1.10 | 0.10 | (-0.15, 0.35) | (0.86, 1.42) | 0.35 |
| OVARY | 14 | 0.05 | 1.05 | 0.10 | (-0.16, 0.26) | (0.85, 1.30) | 0.63 |
| LUNG | 21 | -0.05 | 0.95 | 0.07 | (-0.19, 0.10) | (0.83, 1.10) | 0.50 |
| COLON | 35 | -0.06 | 0.94 | 0.05 | (-0.16, 0.04) | (0.86, 1.04) | 0.25 |
| STOMACH | 27 | -0.08 | 0.92 | 0.07 | (-0.22, 0.06) | (0.81, 1.06) | 0.25 |
| UTERUS | 42 | -0.10 | 0.90 | 0.04 | (-0.19, 0.01) | (0.82, 0.99) | 0.02 |

*FIG. 13*

GENE SCC-112 AND DIAGNOSTIC AND THERAPEUTIC USES THEREOF

CROSS REFERENCE TO RELATED APPLICATIONS

This application is a continuation of copending International Patent Application PCT/US02/10850, which was filed on Apr. 8, 2002, which designates the United States of America, which was published under the Patent Cooperation Treaty on Oct. 17, 2002 as Publication Number WO 02/081641, and which (as filed and as published) is incorporated by reference in its entirety herein. This application also claims benefit of priority to Provisional Application Ser. No. 60/281,780, filed Apr. 6, 2001, which is incorporated by reference in its entirety herein.

STATEMENT REGARDING FEDERALLY SPONSORED RESEARCH AND DEVELOPMENT

This invention was made with government support under grant numbers CA58984, CA68322, and CA74175 awarded by NIH. The Government has certain rights in the invention.

FIELD OF THE INVENTION

The present invention relates to a gene that encodes a polypeptide that modulates apoptosis. This polypeptide is a useful target for identifying compounds that modulate cancer progression by regulating apoptosis. Also, this polypeptide is useful as a diagnostic target for detecting cancers wherein this polypeptide is underexpressed, e.g., breast cancer, and kidney cancer as well as cancers where this polypeptide is overexpressed, e.g. uterine, stomach, colon or lung cancer.

BACKGROUND OF THE INVENTION

Alterations in the cellular genes which directly or indirectly control cell growth and differentiation are considered to be the main cause of cancer. The raf gene family includes three highly conserved genes termed A-, B- and c-raf (also called raf-1). Raf genes encode protein kinases that are thought to play important regulatory roles in signal transduction processes that regulate cell proliferation. Expression of the c-raf protein is believed to play a role in abnormal cell proliferation since it has been reported that 60% of all lung carcinoma cell lines express unusually high levels of c-raf mRNA and protein. Rapp et al., The Oncogene Handbook, E. P. Reddy, A. M Skalka and T. Curran, eds., Elsevier Science Publishers, New York, 1988, pp. 213-253.

Malignant tumors develop through a series of stepwise, progressive changes that lead to the loss of growth control characteristic of cancer cells, i.e., continuous unregulated proliferation, the ability to invade surrounding tissues, and the ability to metastasize to different organ sites. Carefully controlled in vitro studies have helped define the factors that characterize the growth of normal and neoplastic cells and have led to the identification of specific proteins that control cell growth and differentiation.

As discussed above, the raf genes are members of a gene family which encode related proteins termed A-, B- and c-raf. Raf genes code for highly conserved serine-threonine-specific protein kinases. These enzymes are differentially expressed; c-raf, the most thoroughly characterized, is expressed in all organs and in all cell lines that have been examined. A- and B-raf are expressed in urogenital and brain tissues, respectively. c-raf protein kinase activity and subcellular distribution are regulated by mitogens via phosphorylation. Various growth factors, including epidermal growth factor, acidic fibroblast growth factor, platelet-derived growth factor, insulin, granulocyte-macrophage colony-stimulating factor, interleukin-2, interleukin-3 and erythropoietin, have been shown to induce phosphorylation of c-raf. Thus, c-raf is believed to play a fundamental role in the normal cellular signal transduction pathway, coupling a multitude of growth factors to their net effect, cellular proliferation.

Certain abnormal proliferative conditions are believed to be associated with raf expression and are, therefore, believed to be responsive to inhibition of raf expression. Abnormally high levels of expression of the raf protein are also implicated in transformation and abnormal cell proliferation. These abnormal proliferative conditions are also believed to be responsive to inhibition of raf expression. Examples of abnormal proliferative conditions are hyperproliferative disorders such as cancers, tumors, hyperplasias, pulmonary fibrosis, angiogenesis, psoriasis, atherosclerosis and smooth muscle cell proliferation in the blood vessels, such as stenosis or restenosis following angioplasty. The cellular signaling pathway of which raf is a part has also been implicated in inflammatory disorders characterized by T-cell proliferation (T-cell activation and growth), such as tissue graft rejection, endotoxin shock, and glomerular nephritis, for example.

Oligonucleotides have been employed as therapeutic moieties in the treatment of disease states in animals and man. For example, workers in the field have now identified antisense, triplex and other oligonucleotide compositions which are capable of modulating expression of genes implicated in viral, fungal and metabolic diseases. Antisense oligonucleotide inhibition of gene expression has proven to be a useful tool in understanding the roles of raf genes. An antisense oligonucleotide complementary to the first six codons of human c-raf has been used to demonstrate that the mitogenic response of T cells to interleukin-2 (IL-2) requires c-raf. Cells treated with the oligonucleotide showed a near-total loss of c-raf protein and a substantial reduction in proliferative response to IL-2. Riedel et al., Eur. J. Immunol. 1993, 23, 3146-3150. Rapp et al. have disclosed expression vectors containing a raf gene in an antisense orientation downstream of a promoter, and methods of inhibiting raf expression by expressing an antisense Raf gene or a mutated Raf gene in a cell. WO application 93/04170. An antisense oligodeoxyribonucleotide complementary to codons 1-6 of murine c-Raf has been used to abolish insulin stimulation of DMA synthesis in the rat hepatoma cell line H4IIE. Tornkvist et al., J. Biol. Chem. 1994, 269, 13919-13921. WO Application 93/06248 discloses methods for identifying an individual at increased risk of developing cancer and for determining a prognosis and proper treatment of patients afflicted with cancer comprising amplifying a region of the c-raf gene and analyzing it for evidence of mutation. Denner et al. discloses antisense polynucleotides hybridizing to the gene for raf, and processes using them. WO 94/15645. Oligonucleotides hybridizing to human and rat raf sequences are disclosed. Iversen et al. discloses heterotypic antisense Oligonucleotides complementary to raf which are able to kill ras-activated cancer cells, and methods of killing raf-activated cancer cells. Numerous oligonucleotide sequences are disclosed, none of which are actually antisense oligonucleotide sequences.

U.S. Pat. No. 5,919,773, to Monia et al. discloses that elimination or reduction of raf gene expression can halt or reverse abnormal cell proliferation. The Monia et al. patent discloses Oligonucleotides targeted to nucleic acids encoding raf. This relationship between an oligonucleotide and its complementary nucleic acid target to which it hybridizes is commonly referred to as "antisense."

It is noted however, that raf-1 involvement marks only a component in a complex growth and cell survival/death pathway, the identification of other components of which may allow more selective, more specific and/or more efficacious targeting of such components. Identification of one or more genes associated with such components would highly beneficial.

OBJECTS AND SUMMARY OF THE INVENTION

Figure 1B:
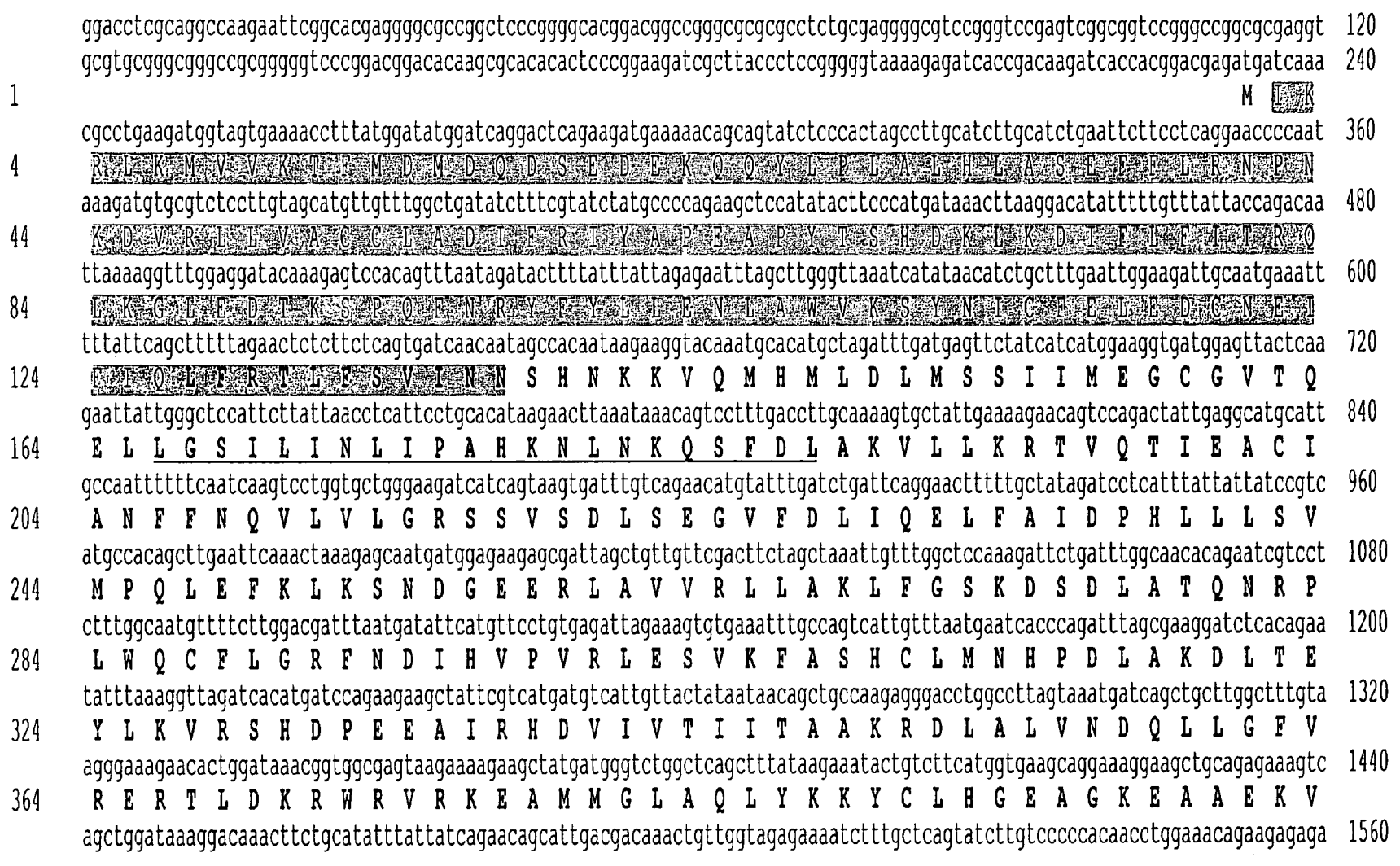

In one embodiment, the invention provides an isolated nucleic acid molecule comprising a polynucleotide selected from the group consisting of
  (a) a polynucleotide encoding amino acids from about 1 to about 1297 of the amino acid sequence contained in FIG. 1B (SEQ ID NO:2);
  (b) a polynucleotide encoding amino acids from about 2 to about 1297 of the amino acid sequence contained in FIG. 1B (SEQ ID NO:2);
  (c) the polynucleotide complement of the polynucleotide of (a) or (b); and
  (d) a polynucleotide at least 90% identical to the polynucleotide of (a), (b) or (c).

In another embodiment, the invention provides a method of increasing survival or proliferation of a cell, comprising inhibiting expression of SCC-112 in said mammalian cell. Preferably, the mammalian cell is transformed with a vector encoding an antisense oligonucleotide corresponding to the SCC-112 sequence in FIG. 1B (SEQ ID NO:1).

In yet another embodiment, the invention provides a method of treating disease cells characterized by SCC-112 overexpression by administration of an antisense oligonucleotide, ribozyme, a small molecule, or small interfering RNA that inhibits SCC-112 expression.

Figure 4:
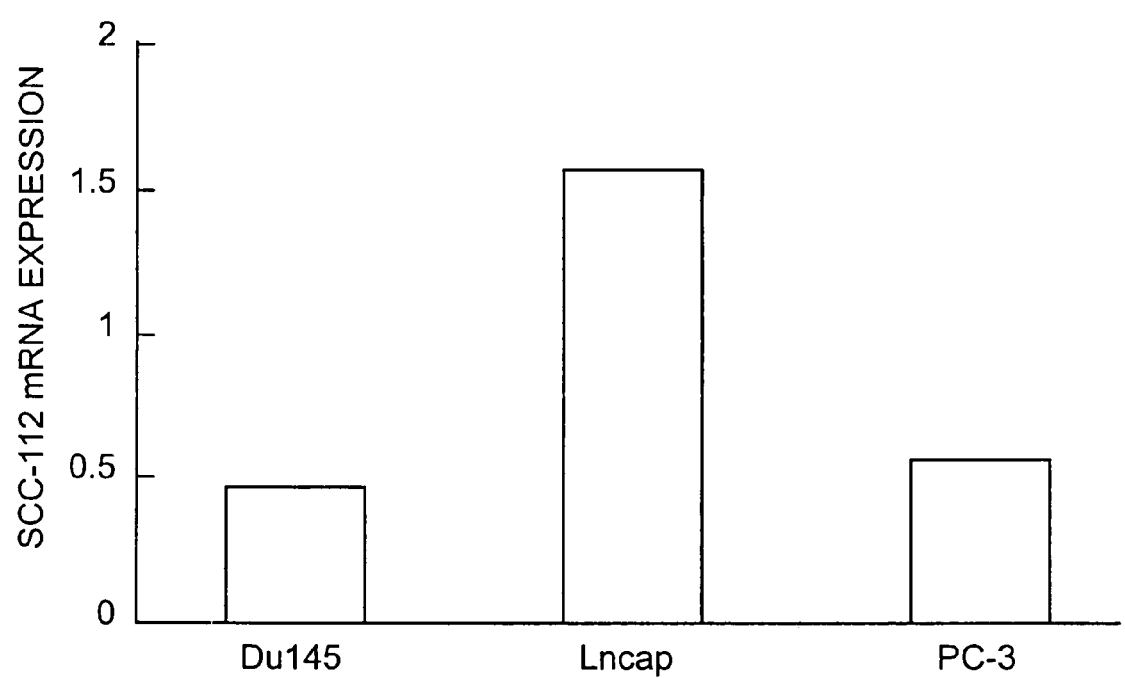
Figure 7C:
Figure 7D:
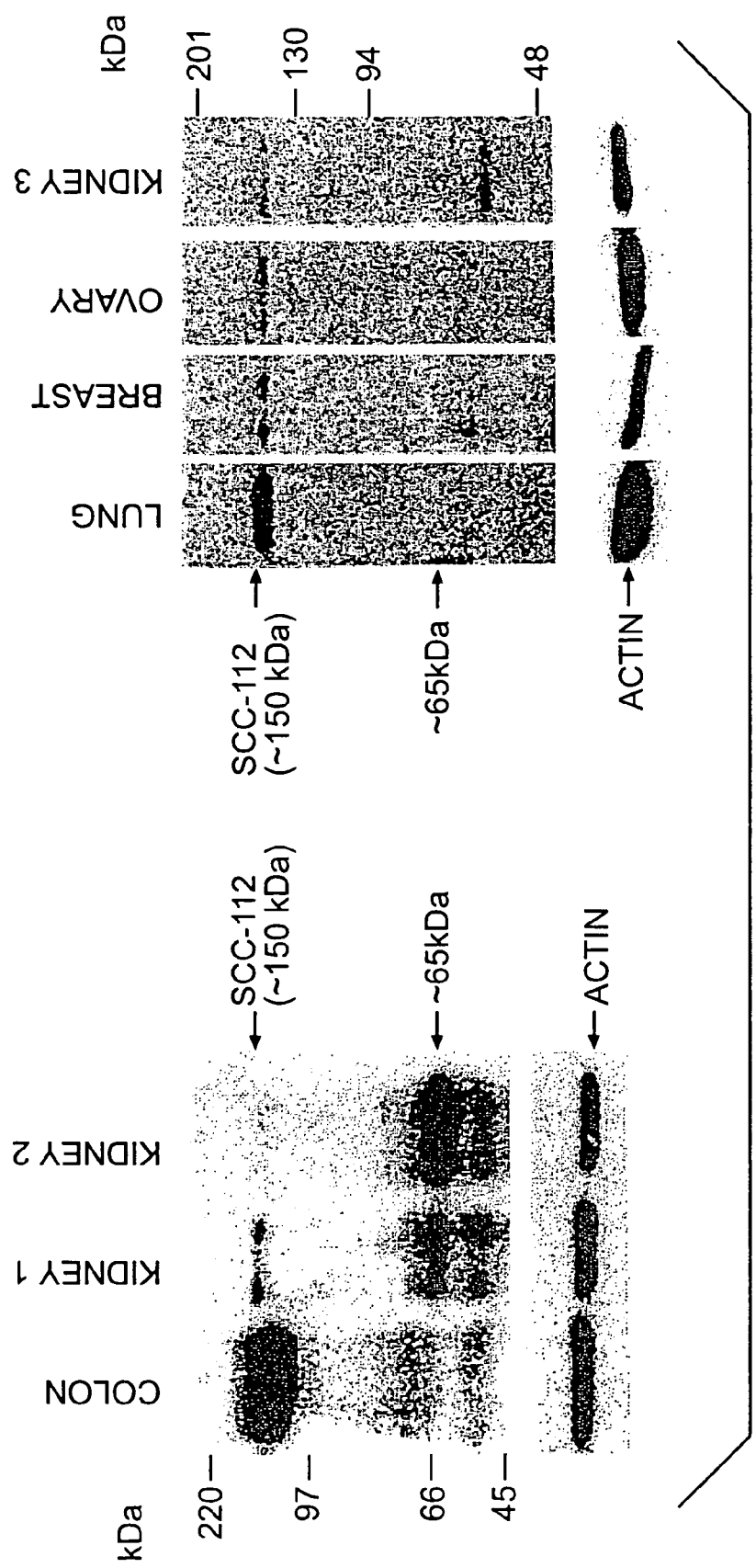
Figure 8A:
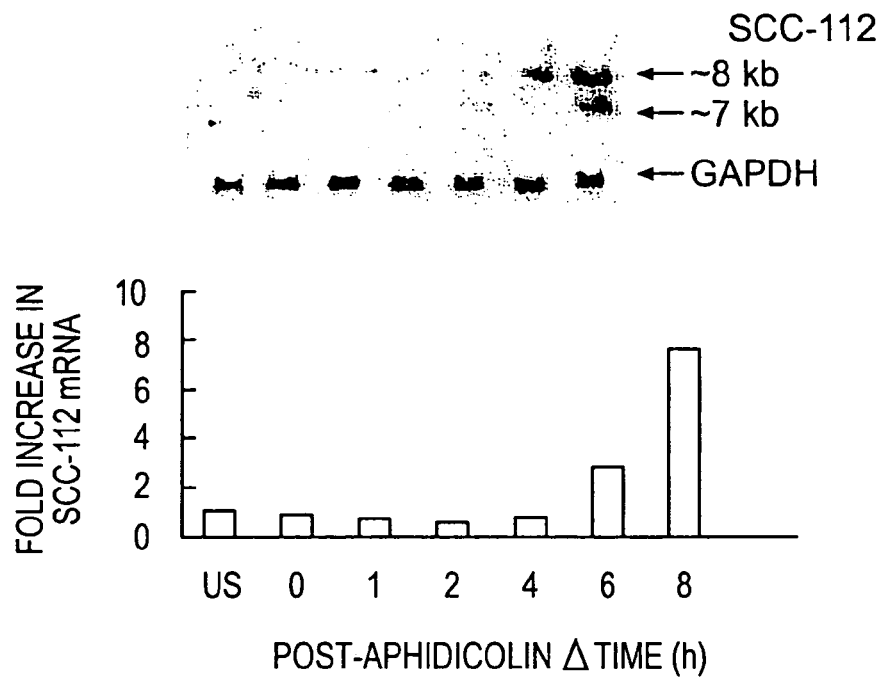
Figure 8B:
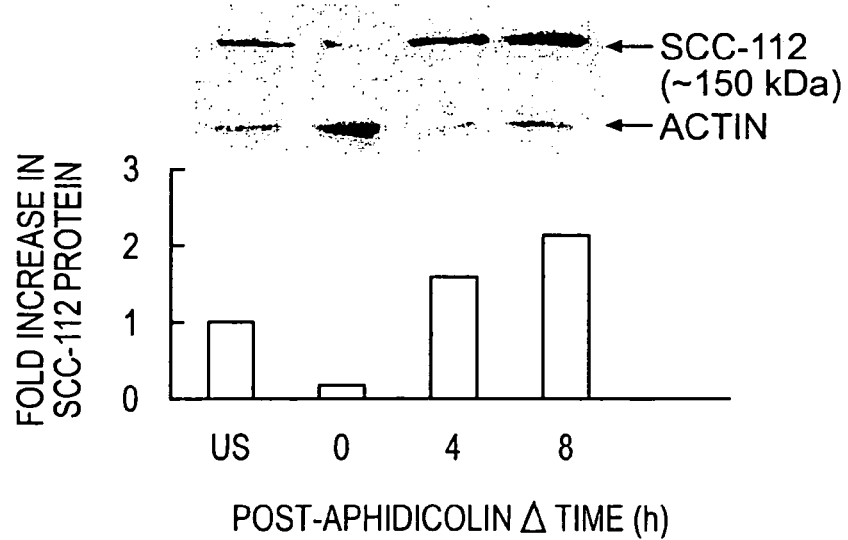
Figure 8C:
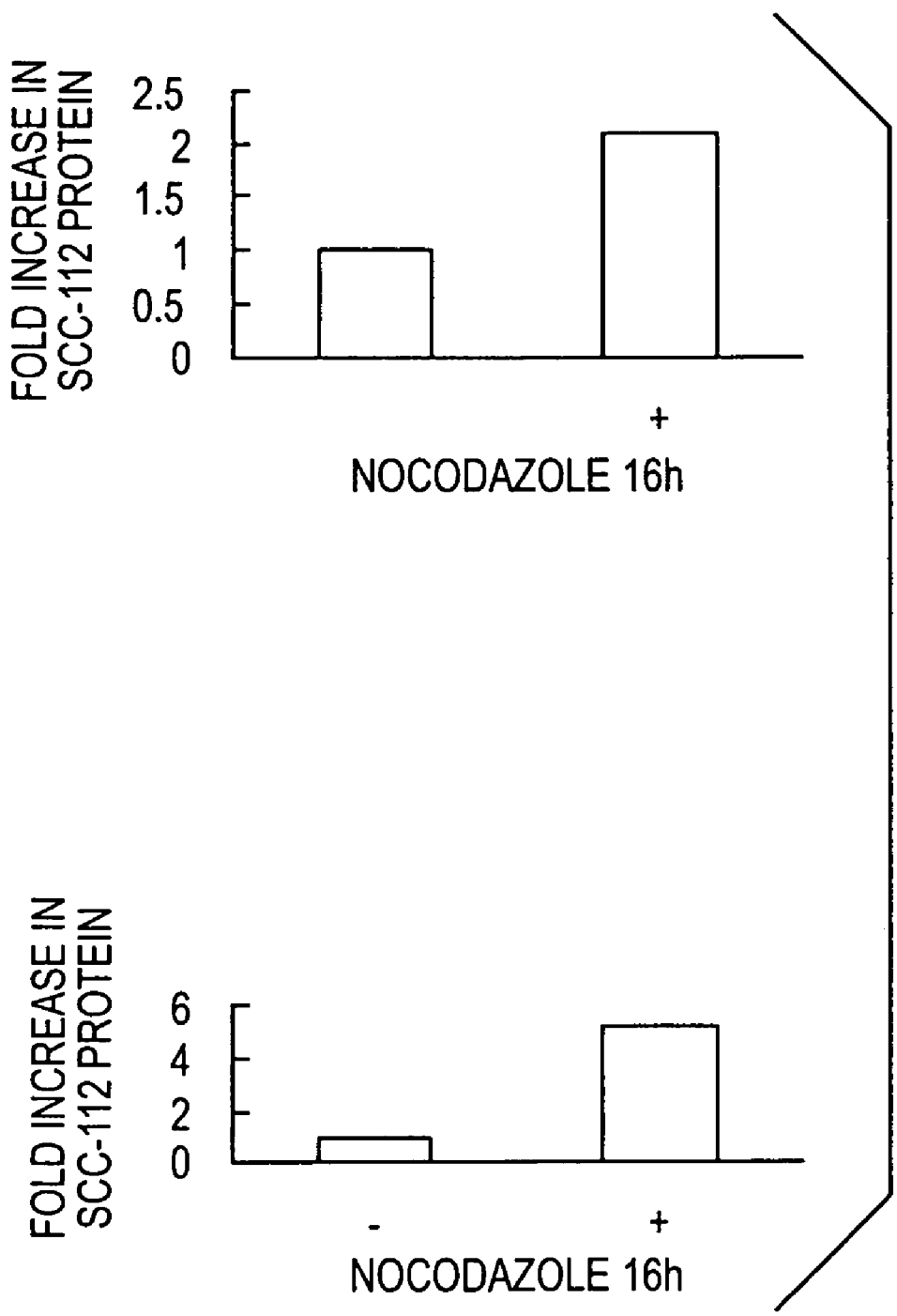
Figure 8D:
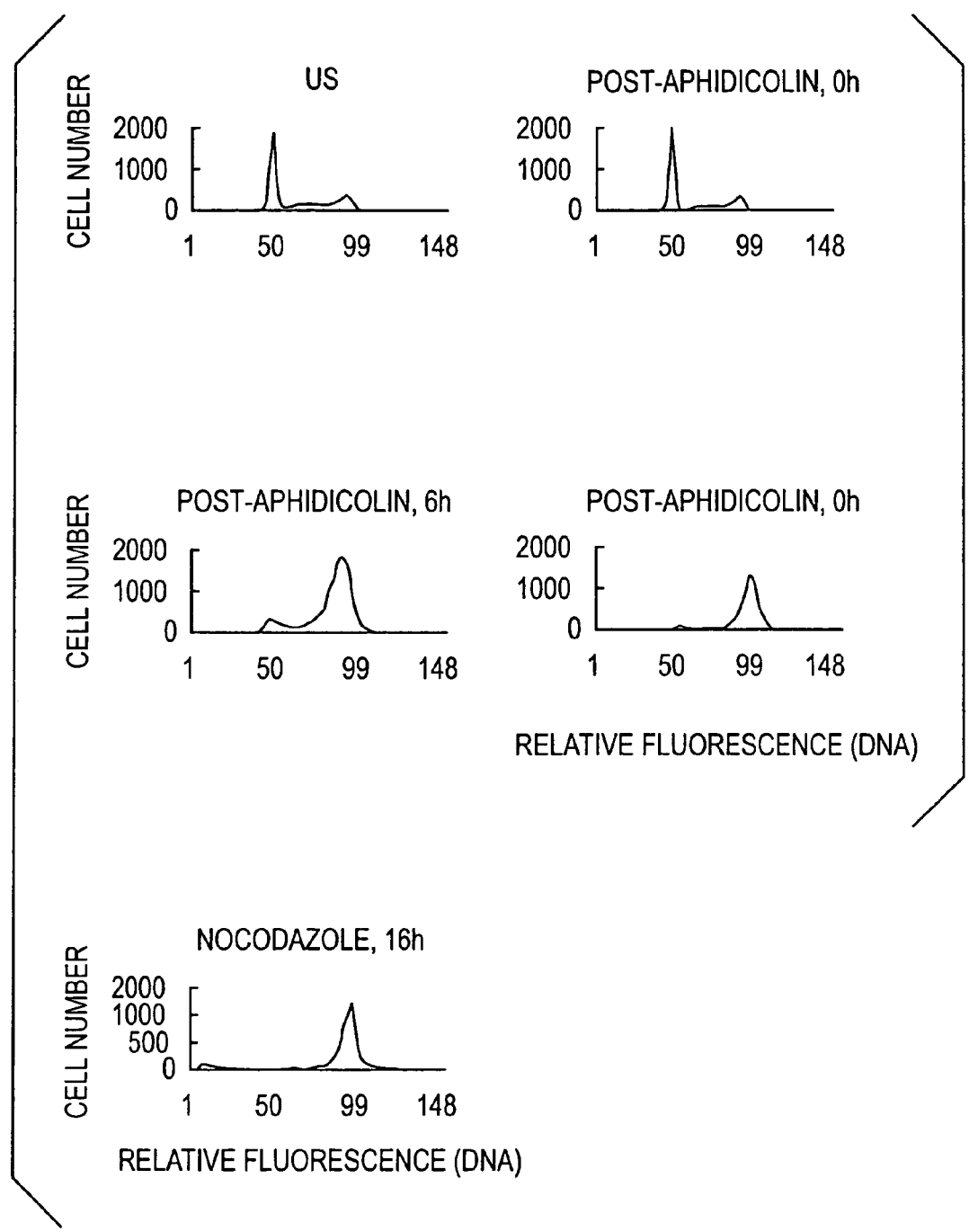

In yet another embodiment, the invention provides a method of treating disease cell characterized by SCC-112 overexpression comprising administering an antibody that specifically binds SCC-112 protein of about 150 kDa or its mutant form of about 65 kDa shown in FIGS. 4 and 7.

In a further embodiment, the invention provides a method of detecting cancer characterized by SCC-112 mRNA underexpression comprising detecting the levels of SCC-112 mRNA expression and correlating said level of expression to the presence or absence of cancer.

In still another embodiment, the invention provides a method of detecting cancer characterized by SCC-112 underexpression comprising detecting the levels of SCC-112 about 150 kDa and or mutant SCC-112 about 65 kDa expression and correlating said level of expression to the presence or absence of cancer.

In a further embodiment, the invention provides a method of inducing apoptosis in cancer cells of a patient comprising administering SCC-1.12 protein or SCC-112 peptide.

In yet another embodiment, the invention provides a method for treating a patient suffering from a degenerative disease or disorder selected from the group consisting of global and focal ischemic and hemorrhage stroke, head trauma, spinal cord injury, hypoxia-induced nerve cell damage, nerve cell damage caused by cardiac arrest or neonatal distress, epilepsy, anxiety, diabetes mellitus, multiple sclerosis, phantom limb pain, causalgia, neuralgias, herpes zoster, spinal cord lesions, hyper algesia, allodynia, Alzheimer's Disease, Huntington's disease, and Parkinson's disease, multiple sclerosis, or amyotrophic lateral sclerosis, wherein said treatment comprises administering to the patient a therapeutically effective amount of SCC-112 DNA, SCC-112 protein; an agent that enhances the expression of the SCC-112 gene or an agent that enhances the production of the SCC-112 protein.

DETAILED DESCRIPTION OF THE FIGURES

FIG. 1. SCC-112 is a novel protein: Structure-activity predictions. (A) Schematic map of SCC-112 cDNA. A 318 bp cDNA fragment, KAS-112 was isolated from human head and neck squamous carcinoma cells (GenBank accession no. AF003254). Blast search using KAS-1.12 cDNA sequence revealed two overlapping sequences, 5177 bp KIAA0648 clone (GenBank accession no. AB014548) and 2247 bp EST sequence (GenBank accession no. A1655954). The complete SCC-112 cDNA sequence deduced from these overlapping sequences is 6744 bp in length as shown above. The cDNA codes for a novel longest open reading frame (ORF) comprised of 1297 amino acids (GenBank accession no. AF294791). The shaded boxes represent the coding region of cDNA. The black boxes represent the 5'- and 3'-untranslated regions of cDNA. The hatched box shown in KAS-112 and the EST sequences was identified as the adjacent genomic DNA sequence.

(B) cDNA SEQ ID NO:1 and predicted amino acid sequences SEQ ID NO:2 of SCC-112. The deduced 6744 bp cDNA sequence of SCC-112 is shown. Nucleotide positions are indicated by numbers on the right. The longest ORF (1297 aa) is shown in single letter code. Amino acid positions are numbered on the left. The poly(A)+ signal sequence is shown in a small box at the 3' end. The proposed main structural features of the SCC-112 protein are: RhoGEF domain (2-137 aa, shaded); Leucine Zipper pattern (166-187 aa, underlined); N-adaptin domain (127-651 aa, boldfaced), SKP1 domain (249-350 aa, not shown here); three PEST sequence sites (597-617 aa, 1143-1663 aa and 1216-1227 aa, bolded and underlined) and two tyrosine kinase phosphorylation sites (858-865 aa and 1030-1036 aa, shaded and bolded). Six nuclear localization signature sequences (920-926 aa, 1225-1231 aa, 1227-1230 aa, 1228-1234 aa, 1232-1235 aa, and 1251-1257 aa) are shown as shaded and underlined. SCC-112 ORF reveals some similarities to chromosome associated proteins and cell cycle proteins in other organisms suggesting a possible role of SCC-112 in chromosome rearrangement during cell cycle. N-Adaptin domain is found in vesicle associated proteins such as p-adaptin, 3'-adaptin, (3-NAP and (3-COP involved in protein trafficking. 6-adaptin is a component of AP-2 adapter complex, which is involved in clathrin-mediated endocytosis in cells. SKP 1 domain has been found in several proteins of SKP1 family (kinetochore protein required for cell cycle progression at both DMA synthesis and mitosis phase and elongin C, subunit of RNA polymerase II transcription factor homologues). SKP1 family proteins have been shown to regulate cell cycle through ubiquitin proteolysis machinery by binding through F-box.

FIG. 2. Expression of SCC-112 mRNA in different cell cycle stages of MDA-MB 435 cells. The MDA-MB 435 cells were grown in DMEM containing 10% FBS. Logarithmically growing cells were arrested in G1/S phase by adding 4 ug/ml of aphidicolin for 24 h (A0). The cells were released from G1/S phase at 24H by washing and addition of fresh medium and harvested at indicated time intervals (A1-A8) for cell cycle analysis and RNA isolation. The cells were arrested at G2/M phase using Nocodazole (100 ng/ml). The total RNA isolated from cells at different cell-cycle stages was subjected to northern hybridization using SCC-112 as probe. For cell-cycle analysis the cells were trypsinized and washed with phosphate buffer saline (PBS). The cells were fixed with 70% ethanol, washed with PBS, and stained with propidium iodide after RNase treatment Flowcytometric analysis was performed on FACsort (Becton Dickinson).

Figure 3A:
Figure 3B:
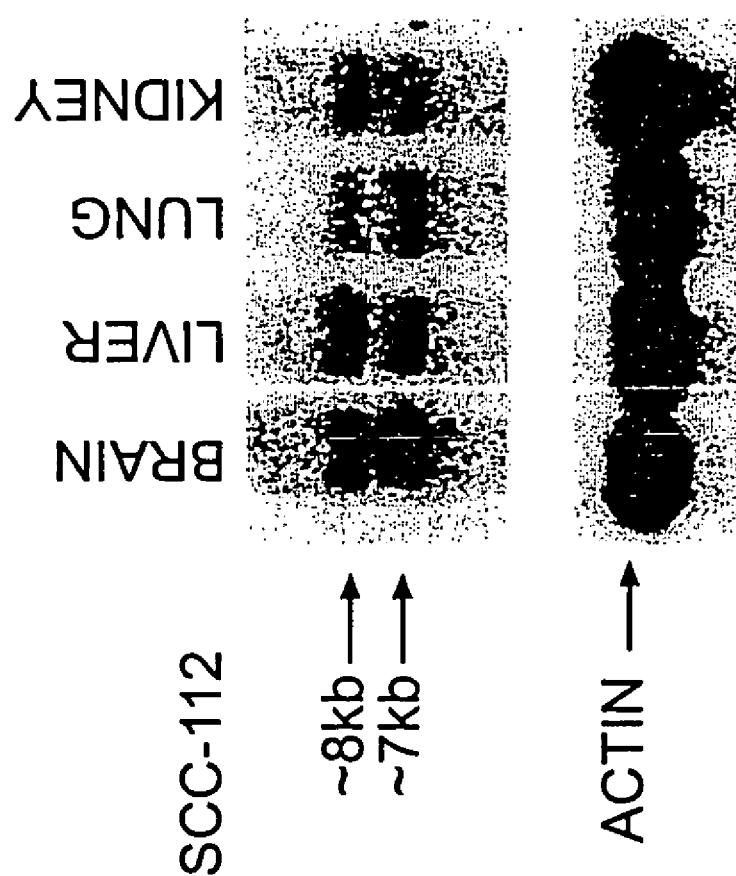
Figure 3C:
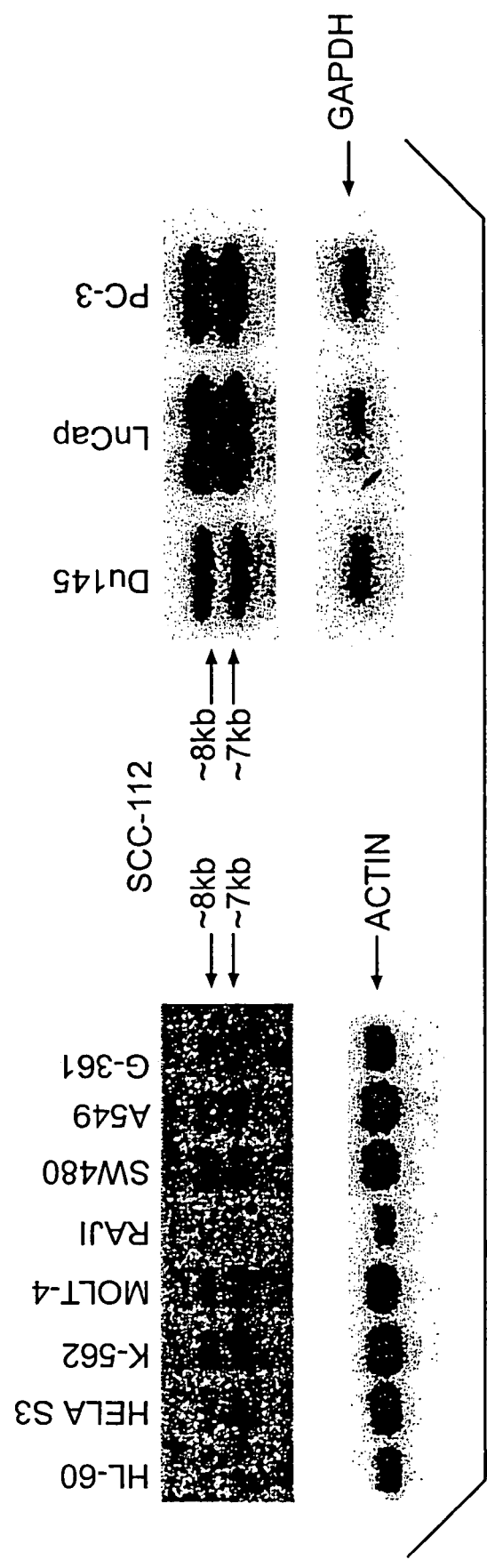

FIG. 3 Expression of SCC-S2 mRNA in human normal tissues and cancer cell lines. (A) and (B) Normal human adult (A) and fetal (B) tissue mRNA blots (CLONTECH) were probed with a radiolabeled SCC-112 cDNA fragment (1568-6744 bp). The blots were reprobed with β-actin cDNA. As shown above, two SCC-112 transcripts ~7.0 kb and ~8.0 kb were detected in most human adult and fetal tissues.

(C) Expression of SCC-112 transcript in human cancer cell lines. Left panel, a cancer cell line blot (CLONTECH) was probed with a radiolabeled SCC-112 cDNA fragment (1568-6744 bp), and then reprobed with β-actin cDNA. Right panel, blot was sequentially hybridized to a radiolabeled SCC-112 cDNA fragment (the EST sequence) and GAPDH cDNA probes. The two SCC-112 transcripts were also detected in most cancer cell lines. Among the prostate cancer cell lines tested, expression of SCC-112 mRNA was found to be elevated in androgen-dependent LnCap cells as compared to androgen-independent PC-3 and Du145 prostate cancer cells. HL60, promyelocytic leukemia; K-562, chronic myelogenous leukemia; MOLT-4, lymphoblastic leukemia; Raji, Burkitt's lymphoma; SW480, colorectal adenocarcinoma; A-549, lung carcinoma; G361, melanoma, Du145 and PC-3, androgen-unresponsive prostate cancer, and LnCap, androgen-responsive prostate cancer.

FIG. 4. Expression of SCC-112 in prostate cancer cells. Total RNA from Androgen independent (Du145 and PC-3) and androgen dependent (LNcap) prostate cancer cell lines were isolated. The RNA was subjected to Northern hybridization using SCC-112 as probe.

Figure 5:
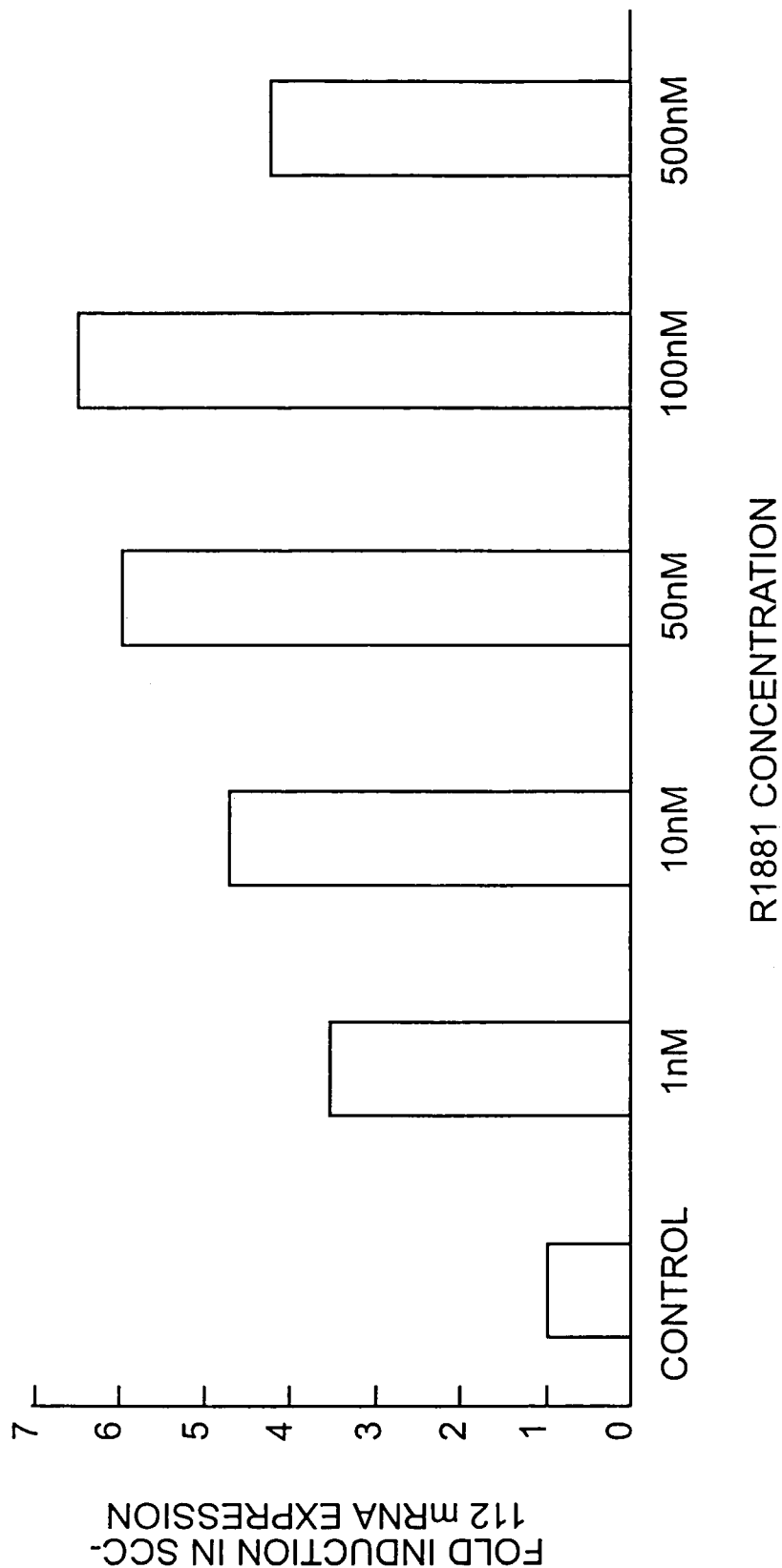

FIG. 5. Androgen induces the steady state levels of SCC-112 mRNA in prostate cancer cells. LNcap prostate cancer cells were grown in IMEM with 5% FBS. Logarithmically growing cells were switched to medium containing 5% charcoal stripped serum 4 hours before the experiment. Indicated concentrations of synthetic androgen, R1881 (NEN) were added for 48 h. Total RNA was isolated and subjected to Northern hybridization using SCC-112 as probe.

Figure 6A:
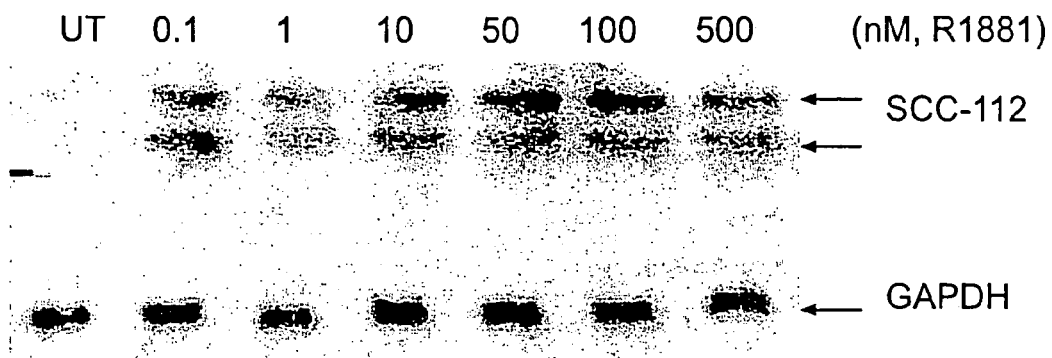
Figure 6B:
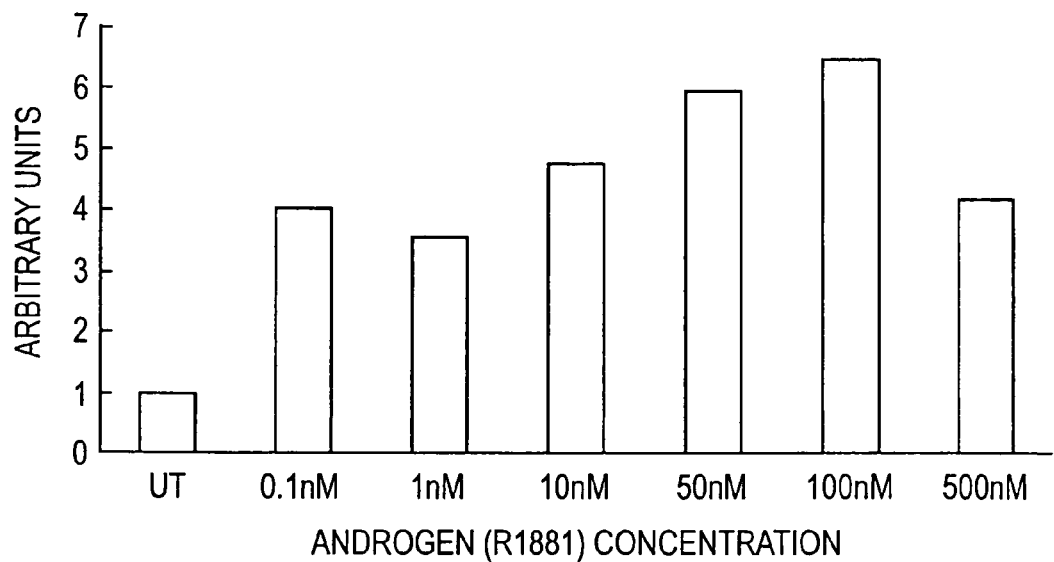

FIG. 6. Androgen induces SCC-112 mRNA expression in androgen-responsive LnCap prostate cancer cells. LnCAP cells were grown in IMEM medium containing 5% fetal bovine serum. Medium was replaced with 5% charcoal-stripped serum containing medium for 24 h, followed by addition of indicated concentration of synthetic androgen (R1881) for 48 h. Total RN A was isolated from various treatments and analyzed by northern blotting and hybridization using a radiolabeled SCC-112 cDNA fragment (1568 bp-6744 bp). As shown above, a 4-7-fold induction of steady state level of SCC-112 transcript (~8.0 kb) was noted in these cells.

FIG. 7. Expression and subcellular localization of human SCC-112 Protein. A rabbit polyclonal antibody against SCC-112 was custom generated at ZYMED Laboratories, Inc. (San Francisco, Calif.) using a synthetic peptide representing C-terminal 1278-1297 amino acids of SCC-112. (A) SCC-112 protein was detected as a single ~150 kDa band in whole cell lysates from A549 human lung cancer cells by western blotting using anti-SCC-112 antibody (lane, 1). SCC-112 protein was immunoprecipitated from A549 cell lysates using anti-SCC-112 antibody and the immunoprecipate was analyzed as above (lane 2). Controls includes the immunoprecipates from mock lysates (lane 3) or pre-immune serum (lanes 4 and 5). The ~150 kDa band size corresponds to the predicted protein size (~146 kDa) of SCC-112 ORF.

(B) Comparison of SCC-112 protein expression in cancer cell lines and corresponding tumor tissue xenografts grown in athymic mice. Logarithmically growing tumor cells were injected subcutaneously into athymic mice and tumors were allowed to grow for 34 weeks. The tumors were excised, and tissue homogenates were subjected to western blot analysis using anti-SCC-112 antibody, followed by reprobing the immunoblot with anti-actin antibody. The expression of SCC-112 protein was significantly decreased in the tumor tissue, T vs. tumor cell inoculates, C. These data suggest that the tumor microenvironment may regulate SCC-112 protein expression. Aspc1 and Colo-357, human pancreatic carcinomas; PC-3, human hormone-unresponsive prostate cancer; MDA-MB 435, human hormone-unresponsive breast cancer.

(C) Expression of SCC-112 protein in normal human tissues. Normal human tissue biopsies were obtained from Co-operative Human Tissue Network (CHTN) resource of the National Cancer Institute, National Institutes of Health. The tissues were homogenized in RIPA lysis buffer (NaCl, 150 mM, pH 7.5; Sodium Deoxycholate, 1% (w/v); Triton X-100, 1% v/v; SDS, 0.1% w/v;) containing 2 mM phenylmethylsulphonyl fluoride (PMSF), aprotinin (20 ug/ml) and leupeptin (20 ug/ml). After incubation on ice for 30 min, the tissue extracts were centrifuged at 12000×g for 15 min at 4° C. followed by SDS-PAGE and Western blot analysis using anti-SCC-112 antibody. As shown above, a ~150 kDa band representing SCC-112 protein was seen in normal human tissues representing colon, lung, ovary, breast and kidney. Interestingly, an additional ~65 kDa band was seen in most normal human kidney samples analyzed (95%, n=22). The appearance of a mutant form of SCC-112 (~65 kDa) in normal kidney tissues implies that this form of SCC-112 has a role in tumor suppression. Alternatively, this mutant SCC-112 protein may complement a possible role of SCC-112 (~150 kDa) in the tumor suppression in normal tissues.

(C) MDA-MB 435 human breast cancer cells were immunostained with anti-SCC-112 antibody, and SCC-112 protein expression was detected using Texas red conjugated goat anti-rabbit IgG secondary antibody. Nuclei were visualized by DAPI staining. As shown in this panel, SCC-112 protein is localized to nucleus of the cell.

FIG. 8. Modulation of the expression of SCC-112 mRNA and protein during cell cycle. (A). The MDA-MB 435 cells were grown in DMEM medium containing 10% FBS. Logarithmically growing cells were arrested in G1/S phase by adding 4 ug/ml of aphidicolin for 24 h (0 h). The cells were released from G1/S phase arrest by washing and addition of fresh medium and harvested at indicated time intervals (1 h-8 h), and processed for cell cycle distribution analysis and RNA isolation. The total RNA isolated from cells at different cell-cycle stages was subjected to northern blot hybridization using a radiolabeled SCC-112 cDNA as probe (1568 bp-6744 bp), followed by reprobing with a radiolabeled GAPDH cDNA probe. Autoradiographs were scanned and data quantified using Image Quant software program (Molecular Dynamics). The steady state level of SCC-112 mRNA was found to be elevated in lateS/earlyG2 (~2.9 fold) (6 h) through G2 phase of cell cycle as compared to unsynchronized MDA-MB 435 cells (~7.6 fold) (8 h).

(B) Logarithmically growing MDA-MB 435 cells were arrested in G1/S phase by adding aphidicolin (4 ug/ml, 24 h) (0 h). The cells were released from G1/S phase arrest by washing and addition of fresh medium and harvested at 4 h and 8 h post-aphidicolin release (4 h and 8 h), and processed for cell-cycle analysis and preparation of whole cell lysates. SCC-112 protein was detected in whole cell lysates by western blot analysis using anti-SCC-112 antibody, followed by quantification using Image Quant software program (Molecular Dynamics). Actin antibody (Sigma) was used as for loading control and quantification analysis. SCC-112 protein level was elevated during S and G2 phases (~2 to 3 fold) (4 h and 8 h).

(C) Expression of SCC-112 mRNA and protein in G2/M phase. Logarithmically growing cells were arrested at G2/M phase using 100 ng/ml of nocodazole for 16 h (+). SCC-112 mRNA (upper) and protein levels (lower) were quantified as above. The SCC-112. mRNA level was ~2 fold higher during G2/M phase (+) as compared to untreated cells (−). SCC-112 protein level was elevated during G2/M phase (~5 fold) in nocodazole treated cells (+) as compared to untreated cells (−).

(D) Cell cycle analysis of MDA-MB 435 cells. For cell-cycle distribution profiles, the cells were trypsinized and washed with phosphate buffer saline (PBS). The cells were fixed with 70% ethanol, washed with PBS, and stained with propidium iodide after RNase treatment. Flow-cytometric analysis was performed at the Fluorescence Activated Cell Sorting Resource of the Lombardi Cancer Center using FACsort (Becton Dickinson). Induction of SCC-112 mRNA and protein during G2/M phase suggest a regulatory role for SCC-112 during cell division and proliferation.

Figure 9A:
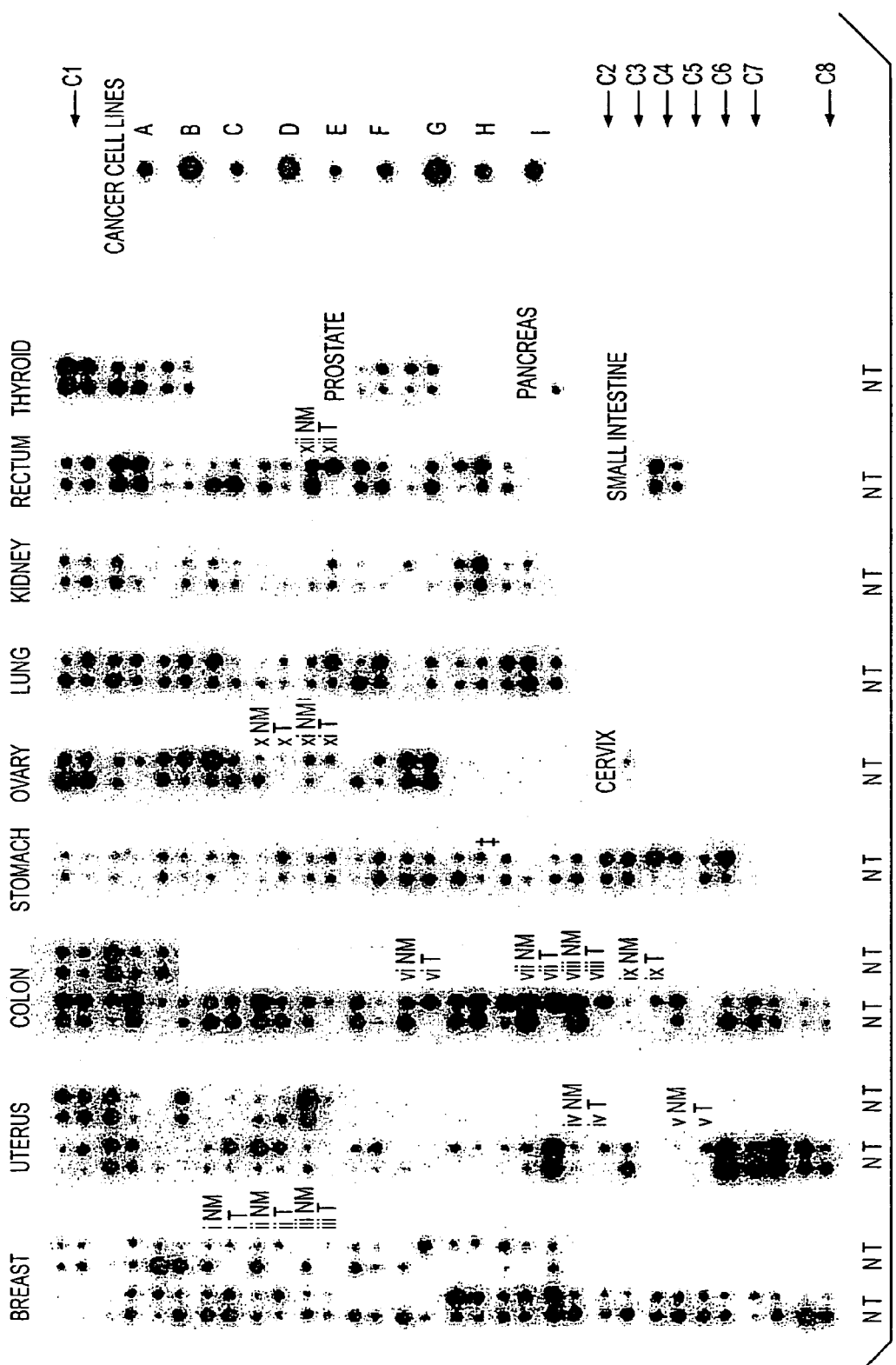
Figure 9B:
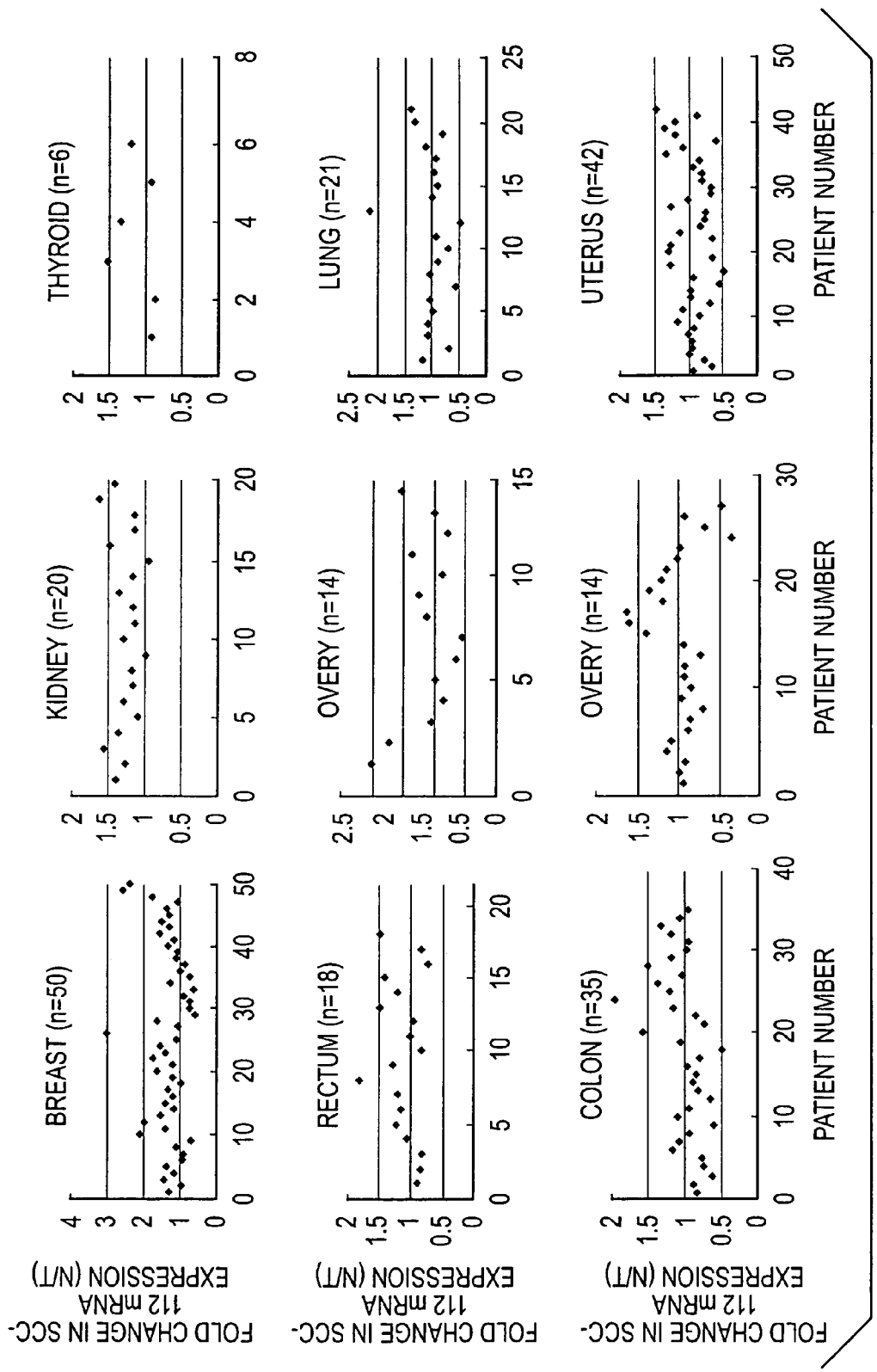

FIG. 9. SCC-112 mRNA expression analysis and identification of SCC-112 as a potential tumor suppressor in human breast and kidney cancers. (A) SCC-112 mRNA expression profiles in human tumor versus corresponding normal tissues. A cancer profiling array blot containing cDNAs from a total of 241 paired human normal and tumor cDNA samples from individual patients, spotted side by side on a nylon membrane, was hybridized with $^{32}$P labeled SCC-112 cDNA (1568 bp-6744 bp) as per manufacturer's instructions (CLONTECH Cancer Profiling Array User Manual PR11929). The membrane was reprobed with human ubiquitin cDNA as internal control. The autoradiographs were scanned and signals were quantified using IMAGEQUANT software (Molecular Dynamics, Sunnyvale, Calif.). The blot also shows SCC-112 mRNA expression in cDNA samples representing established human cancer cell lines (A, Hela; B, Burkitts's lymphoma Daudi; C, K562; D, HL-60; E, G361; F, A549; G, MOLT4; H, SW480; I, Burkitt's lymphoma, Raji). N, normal tissue; T, tumor tissue; i-xii, twelve groups containing cDNAs from three tissues, normal (N), tumor (T), and corresponding metastatic (M), from the same patient. C1-C8, control cDNA spots (C1 and C8, ubiquitin cDNA; C2, yeast total RNA; C3, yeast tRNA; C4, *E. coli* DNA; C5, poly A+; C6, human Cot-1 DNA; C7, human genomic DNA). (B) Quantification of the fold change in SCC-112 mRNA level in normal tissue (N) vs. corresponding tumor tissue (T) from the same patient. The SCC-112 mRNA signals observed in panel A in various normal (N) and tumor (T) tissues were normalized against the ubiquitin signal at the corresponding spots, and the SCC-112 mRNA expression level was plotted as fold change in expression in normal versus tumor tissue (NIT). The data shown in this figure suggest that a vast majority of normal tissues have higher level of SCC-112 mRNA as compared to the tumor tissue counterparts tested in patients with breast (76%, n=50) or kidney cancer (90%, n=20). In contrast, only 56% of the rectal cancer patients examined had higher level in their normal tissue vs. tumor tissue (n=18), and only 50% of the thyroid (n=6) or ovarian cancer patients examined (n=14) had higher SCC-112 mRNA level in normal tissue vs. matched tumor tissue. Interestingly, SCC-112 mRNA levels were higher in tumor tissues in patients with uterine (69%, n=42), stomach (67%, n=27), colon (57%, n=35), or lung cancer (57%, n=21). n, total number of patients examined. Together with the statistical significance analysis of this data shown in Table 1, we conclude that SCC-112 may be a tumor suppressor in human breast and kidney cancers.

Figure 10:
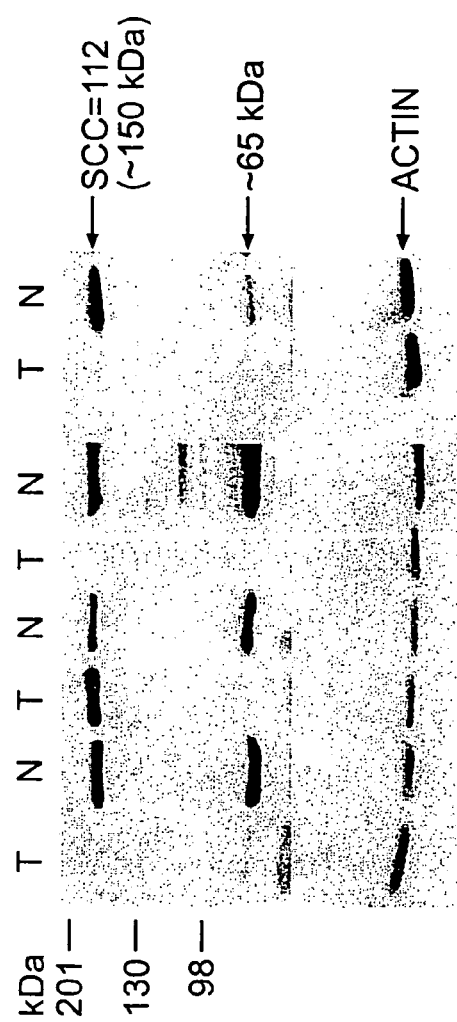
Figure 11:
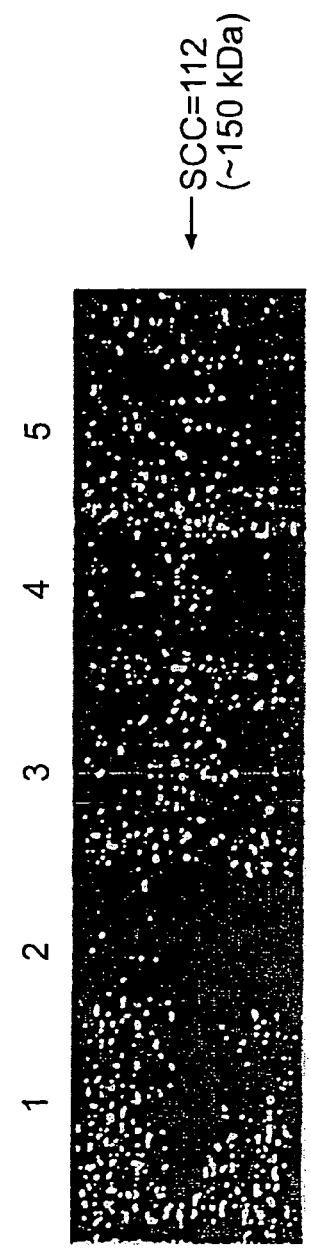

FIG. 10. Expression of SCC-112 protein in human Renal Cell Carcinomas and Normal Adjacent Renal Tissues. Human renal tumor and matched normal adjacent tissues were obtained from Co-operative Human Tissue Network (CHTN) resource of the National Cancer Institute, National Institutes of Health. The tissues were homogenized and whole cell lysates were analyzed by western blotting using anti-SCC-112 antibody, followed by reimmunoblotting with anti-actin antibody. Representative data are shown in this figure. N, Normal adjacent tissue, T, Renal Cell Carcinoma FIG. 11. SCC-112 protein expression in A549 tumor cells. The rabbit polyclonal antibody was raised against a synthetic peptide derived from 1278-1297 amino acids of SCC-112 (KLQDLAKKAAPAERQIDLQR) at Zymed laboratories San Francisco, Calif. SCC-112 protein was detected as a single band (about 150 kDa) in whole cell lysates prepared from human lung cancer cells (A549) by western blotting using SCC-112 antibody (lane, 1). SCC-112 protein was immunoprecipitated from A549 cell lysates with anti-SCC-112 antibody and the immunoprecipitates were immunoblotted as above (lane 2). Mock lysate, lanes 3; preimmune serum, lanes 4 and 5.

Figure 12:
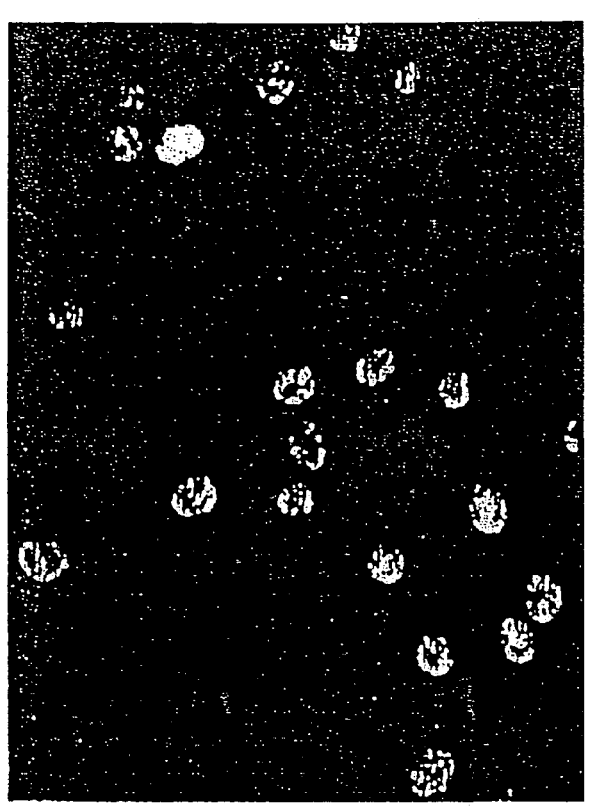
Figure 12:
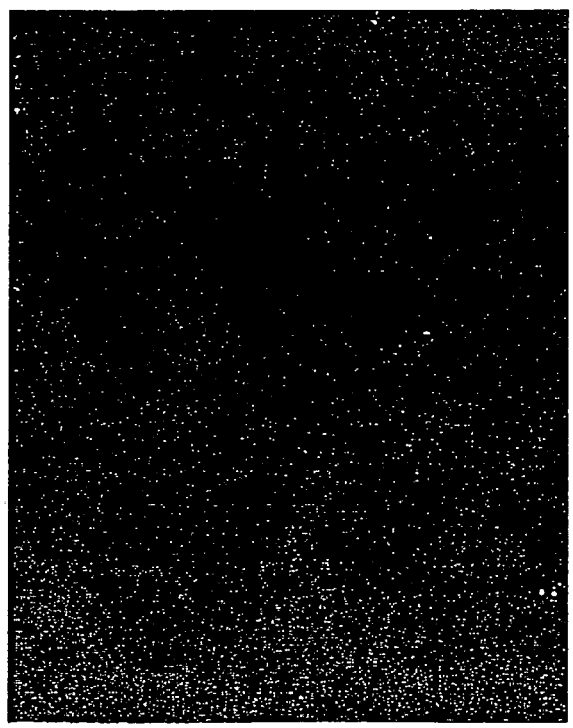

FIG. 12. Shows that SCC-112 protein is located in the nucleus. MDA-MB 435 breast cancer cells were immunostained with rabbit polyclonal anti-SCC-112 antibody and SCC-112 expression was detected using Texas red conjugated goat anti-rabbit secondary antibody. Nuclei were visualized by DAPI counter staining.

FIG. 13. Table 1 showing statistical analysis of the fold change in SCC-112 mRNA expression level in tumor tissue versus corresponding normal tissue from individual cancer patients.

DETAILED DESCRIPTION OF THE INVENTION

The molecular genetic factors that negate cell death and contribute to tumor growth and metastasis can be attractive targets for therapeutic intervention. In a search for such genes, the present inventors have identified a full length cDNA encoding a gene which is hereby named as SCC-112 that is a mediator of apoptosis.

The present invention is based at least in part on the identification of a new human gene which has been named by the inventors and as SCC-112. The amino acid sequence of SCC-112 (SEQ ID NO:2) is shown in FIG. 1. The invention is also based on the discovery that mRNA expression level of this gene varies during different phases of the cell cycle and is maximum during G phase of the cell cycle (FIG. 2). One particular aspect of the invention is based on the discovery that the steady state level of SCC-112 mRNA is relatively higher in androgen-responsive human LNCap prostate cancer cells as compared with hormone-refractory DU-145 and PC-3 prostate cancer cells (FIG. 4). This discovery was confirmed through the treatment of LNCap cells with synthetic androgen (R1881 induces SCC-112 mRNA expression in these cells) (FIG. 5).

As discussed above, Raf-1 Ser/Thr protein kinase is an important component of the signal transduction pathway leading to cell proliferation and cell survival; however, effectors of this complex cascade are not well-defined. The identification of gene SCC-112 as novel molecular target for cancer treatment and diagnosis, reasoned the modulation of the Raf-1 expression in cancer cells was investigated to identify differential gene expression of key regulatory molecules. Using the differential display of mRNA strategy, the inventors isolated a partial cDNA fragment (318 bp) of a novel gene, SCC-112 in head and neck squamous carcinoma cells (PCI-06A). Full length SCC-112 cDNA sequence was deduced by Genbank database search and "mRNA walking." SCC-112 cDNA is 6744 bp in length and contains an ORF of 1397 amino acids.

Two SCC-112 transcripts (~7.0 kb and 8.0 kb) were observed in normal tissues and cancer cell lines. Northern analysis indicated that the steady state level of SCC-112 mRNA peaked at G2 phase, with relatively higher levels during early G2 and M phase as compared to unsynchronized cells (early G2, 2.9 fold; G2, ~7.6 fold; M phase, ~2 fold). The SCC-112 mRNA level was elevated in a human androgen-responsive prostate cancer cell line, LNCap as compared to hormone-unresponsive prostate cancer cell lines, DU145 and PC3.

SCC-112 mRNA expression was also induced in LNCap cells treated with a synthetic androgen R1881 (DUPONT) as compared to untreated cells (1 nM to 100 nM, 48 h, ~4- to 7-fold). Deregulation of cell cycle and/or hormone-response can impact normal cellular processes.

Aberrant cell cycle is an important factor in cancer growth and proliferation. The discovery of the SCC-112 gene and its implication in cell cycle variations provides opportunities for manipulation of the level of SCC-112 in cancer cells to target cell cycle and provide novel therapeutic and diagnostic protocols based on the newly identified SCC-112 gene and role thereof in cell cycle.

One particularly preferred embodiment of the invention is based on the discovery that decreasing the amount of SCC-112 may slow down progression of cells through the cell cycle, cause tumor growth arrest, tumor regression, tumor cell death and/or potentiate radiation/drug-induced cytotoxicity.

As discussed in more detail below in conjunction with FIG. 10, the data presented herein shows changes in SCC-112 protein level in kidney tumor specimens compared to matched normal kidney tissues. Seven out of eleven kidney tumor samples examined had lower expression of the ~150 kDa band as compared to their matched normal tissue counterparts. Protein expression was detected by western blotting using a custom made anti-peptide SCC-112 antibody, and the blots were reprobed with anti-actin antibody. Patient specimens were provided by the Co-operative Human Tissue Network Resource of the NCI (NIH).

In the data shown in FIG. 10 renal tumor and matched normal adjacent tissues from a total of twenty patients were examined. A visual examination of the western blots indicated that two bands, ~150 kDa and ~65 kDa represent the SCC-112 protein. Based on these data, ~150 kDa SCC-112 protein seems to be necessary but not sufficient for tumor suppression, whereas ~65 kDa is necessary and may be sufficient for tumor suppression in normal kidney tissue. Alternatively, the ~150 kDa and ~65 kDa proteins may complement each other in the exhibition of the tumor suppressor phenotype, a hall mark of most normal tissues.

Another preferred embodiment is based on the discovery that SCC-112 expression may modify prostate cell response to hormones.

In yet another embodiment, the invention provides therapies for degenerative diseases such as Alzheimer's disease.

Nerve cell death (degeneration) can cause potentially devastating and irreversible effects for an individual and may occur e.g. as a result of stroke, heart attack or other brain or spinal chord ischemia or trauma. Additionally, neurodegenerative disorders-involve nerve cell death (degeneration) such as Alzheimer's disease, Parkinson's disease, Huntington's disease, Amyotrophic Lateral Sclerosis, Down's Syndrome and Korsakoff's disease.

Alzheimer's Disease (AD) is a progressive neurodegenerative characterized clinically by progressive loss of intellectual function. AD affects about 10% of the population who are beyond age 65. It attacks 19% of individuals 75 to 85 years old, and 45% over age 85. AD is the fourth leading cause of death in adults, behind heart disease, cancer, and stroke. AD accounts for about 75% of senile dementia. This central nervous system disorder is marked by a variety of symptoms such as degeneration of neurons, development of amyloid plaques, neurofibrillary tangles, declination of acetylcholine and atrophy of cerebral cortex. Patients with AD suffer loss of short-term memory initially followed by a decline in cognitive function and finally a loss of the ability to care for themselves. The cost of caring for patients, including diagnosis, nursing, at-home care, and lost wages is estimated at between $80 billion and $90 billion per year.

The drastic impairment of function associated with AD is caused by the presence of neuritic plaques in the neocortex and the loss of presynaptic markers of cholinergic neurons. Neuritic plaques are composed of degenerating axons and nerve terminals, often surrounding an amyloid core and usually containing reactive glial elements. Another characteristic pathologic feature of Alzheimer's Disease is the neurofibrillary tangle, which is an intraneuronal mass which corresponds to an accumulation of abnormally phosphorylated tau protein polymerized into fibrillar structures termed paired helical filaments. In addition, the neurofibrillary tangle also contains highly phosphorylated neurofilament proteins.

It is therefore an aspect of the invention to provides a method for treating a patient suffering from a degenerative disease or disorder selected from the group consisting of global and focal ischemic and hemorrhagic stroke, head trauma, spinal cord injury, hypoxia-induced nerve cell damage, nerve cell damage caused by cardiac arrest or neonatal distress, epilepsy, anxiety, diabetes mellitus, multiple sclerosis, phantom limb pain, causalgia, neuralgias, herpes zoster, spinal cord lesions, hyper algesia, allodynia, Alzheimer's Disease, Huntington's disease, and Parkinson's disease multiple sclerosis, or amyotrophic lateral sclerosis, wherein said treatment comprises administering to the patient a therapeutically effective amount of SCC-112 DNA, SCC-112 protein; an agent that enhances the expression of the SCC-112 gene or the production of the SCC-112 protein.

The invention is broadly directed to a novel gene referred to as SCC-112. Reference to SCC-112 herein is intended to be construed to include SCC-112 proteins of any origin which are substantially homologous to and which are biologically equivalent to the SCC-112 characterized and described herein. Such substantially homologous SCC-112 may be native to any tissue or species and, similarly, biological activity can be characterized in any of a number of biological assay systems.

The term "biologically equivalent" is intended to mean that the compositions of the present invention are capable of demonstrating some or all of the same biological properties in a similar fashion, not necessarily to the same degree as the SCC-112 isolated as described herein or recombinantly produced human SCC-112 of the invention.

By "substantially homologous" it is meant that the degree of homology of human SCC-112 from any species is greater than that between SCC-112 and any previously reported apoptopic modulating gene.

Sequence identity or percent identity is intended to mean the percentage of same residues between two sequences, wherein the two sequences are aligned using the Clustal method (Higgins et al., Cabios 8:189-191, 1992) of multiple sequence alignment in the Lasergene biocomputing software (DNASTAR, INC, Madison, Wis.). In this method, multiple alignments are carried out in a progressive manner, in which larger and larger alignment groups are assembled using similarity scores calculated from a series of pairwise alignments. Optimal sequence alignments are obtained by finding the maximum alignment score, which is the average of all scores between the separate residues in the alignment, determined from a residue weight table representing the probability of a given amino acid change occurring in two related proteins over a given evolutionary interval. Penalties for opening and lengthening gaps in the alignment contribute to the score. The default parameters used with this program are as follows: gap penalty for multiple alignment=IO; gap length penalty for multiple alignment=10; k-tuple value in pairwise alignment=1; gap penalty in pairwise alignment=3; window value in pairwise alignment=5; diagonals saved in pairwise alignment=5. The residue weight table used for the alignment program is PAM250 (Dayhoff et al., in Atlas of Protein Sequence and Structure, Dayhoff, Ed., NDRF, Washington, Vol. 5, suppl. 3, p. 345, 1978).

Percent conservation is calculated from the above alignment by adding the percentage of identical residues to the percentage of positions at which the two residues represent a conservative substitution (defined as having a log odds value of greater than or equal to 0.3 in the PAM250 residue weight table). Conservation is referenced to human SCC-112 when determining percent conservation with non-human SCC-112, and referenced to SCC-112 when determining percent conservation with non-SCC-112 proteins. Conservative amino acid changes satisfying this requirement are: R-K; E-D, Y-F, L-M; V-I, Q-H.

Polypeptide Fragments

The invention provides polypeptide fragments of the disclosed proteins. Polypeptide fragments of the invention can comprise at least 8, 10, 12, 15, 18, 19, 20, 25, 50, 75, 100, or 108 contiguous amino acids of the amino acid sequence contained in FIG. 1B (SEQ ID NO:2). Also included are all intermediate length fragments in this range, such as 51, 52, 53, etc.; 70, 71, 72, etc.; and 100, 101, 102, etc., which are exemplary only and not limiting.

Biologically Active Variants

Variants of the SCC-112 polypeptide disclosed herein can also occur. Variants can be naturally or non-naturally occurring. Naturally occurring variants are found in humans or other species and comprise amino acid sequences which are substantially identical to the amino acid sequence shown in FIG. 1B (SEQ ID NO:2). Species homologs of the protein can be obtained using subgenomic polynucleotides of the invention, as described below, to make suitable probes or primers to screening cDNA expression libraries from other species, such as mice, monkeys, yeast, or bacteria, identifying cDNAs which encode homologs of the protein, and expressing the cDNAs as is known in the art.

Non-naturally occurring variants which retain substantially the same biological activities as naturally occurring protein variants are also included here. Preferably, naturally or non-naturally occurring variants have amino acid sequences which are at least 85%, 90%, or 95% identical to the amino acid sequence encoded by a nucleic acid sequence comprising the sequence shown in FIG. 1B (SEQ ID NO:2). More preferably, the molecules are at least 96%, 97%, 98% or 99% identical. Percent identity is determined using any method known in the art. A non-limiting example is the Smith-Waterman homology search algorithm using an affine gap search with a gap open penalty of 12 and a gap extension penalty of 1. The Smith-Waterman homology search algorithm is taught in Smith and Waterman, *Adv. Appl. Math.* (1981) 2:482-489.

Guidance in determining which amino acid residues can be substituted, inserted, or deleted without abolishing biological or immunological activity can be found using computer programs well known in the art, such as DNASTAR software. Preferably, amino acid changes in protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids.

A subset of mutants, called muteins, is a group of polypeptides in which neutral amino acids, such as serines, are substituted for cysteine residues which do not participate in disulfide bonds. These mutants may be stable over a broader temperature range than native secreted proteins. See Mark et al., U.S. Pat. No. 4,959,314.

It is reasonable to expect that an isolated replacement of a leucine with an isoleucine or valine, an aspartate with a glutamate, a threonine with a serine, or a similar replacement of an amino acid with a structurally related amino acid will not have a major effect on the biological properties of the resulting secreted protein or polypeptide variant. Properties and functions of SCC-112 or polypeptide variants are of the same type as a protein comprising the amino acid sequence encoded by a nucleic acid sequence comprising the nucleotide sequence shown in FIG. 1B (SEQ ID NO:1), although the properties and functions of variants can differ in degree.

SCC-112 protein variants include glycosylated forms, aggregative conjugates with other molecules, and covalent conjugates with unrelated chemical moieties. SCC-112 protein variants also include allelic variants, species variants, and muteins. Truncations or deletions of regions which do not affect the differential expression of the SCC-112 protein gene are also variants. Covalent variants can be prepared by linking functionalities to groups which are found in the amino acid chain or at the N- or C-terminal residue, as is known in the art.

It will be recognized in the art that some amino acid sequence of the SCC-112 protein of the invention can be varied without significant effect on the structure or function of the protein. If such differences in sequence are contemplated, it should be remembered that there are critical areas on the protein which determine activity. In general, it is possible to replace residues that form the tertiary structure, provided that residues performing a similar function are used. In other instances, the type of residue may be completely unimportant if the alteration occurs at a non-critical region of the protein. The replacement of amino acids can also change the selectivity of binding to cell surface receptors. Ostade et al., *Nature* 361:266-268 (1993) describes certain mutations resulting in selective binding of TNF-alpha to only one of the two known types of TNF receptors. Thus, the polypeptides of the present invention may include one or more amino acid substitutions, deletions or additions, either from natural mutations or human manipulation.

The invention further includes variations of the SCC-112 polypeptide which show comparable expression patterns or which include antigenic regions. Such mutants include deletions, insertions, inversions, repeats, and type substitutions. Guidance concerning which amino acid changes are likely to be phenotypically silent can be found in Bowie, J. U., et al., "Deciphering the Message in Protein Sequences: Tolerance to Amino Acid Substitutions," *Science* 247:1306-1310 (1990).

Of particular interest are substitutions of charged amino acids with another charged amino acid and with neutral or negatively charged amino acids. The latter results in proteins with reduced positive charge to improve the characteristics of the disclosed protein. The prevention of aggregation is highly desirable. Aggregation of proteins not only results in a loss of activity but can also be problematic when preparing pharmaceutical formulations, because they can be immunogenic. (Pinckard et al., *Clin. Exp. Irrimunol.* 2:331-340 (1967); Robbins et al., *Diabetes* 36:838-845 (1987); Cleland et al., *Crit. Rev. Therapeutic Drug Carrier Systems* 10:307-377 (1993)).

Amino acids in the polypeptides of the present invention that are essential for function can be identified by methods known in the art, such as site-directed mutagenesis or alanine-scanning mutagenesis (Cunningham and Wells, *Science* 244:1081-1085 (1989)). The latter procedure introduces single alanine mutations at every residue in the molecule. The resulting mutant molecules are then tested for biological activity such as binding to a natural or synthetic binding partner. Sites that are critical for ligand-receptor binding can also be determined by structural analysis such as crystallization, nuclear magnetic resonance or photoaffinity labeling (Smith et al., *J. Mol. Biol.* 224:899-904 (1992) and de Vos et al. *Science* 255:306-312 (1992)).

As indicated, changes are preferably of a minor nature, such as conservative amino acid substitutions that do not significantly affect the folding or activity of the protein. Of course, the number of amino acid substitutions a skilled artisan would make depends on many factors, including those described above. Generally speaking, the number of substitutions for any given polypeptide will not be more than 50, 40, 30, 25, 20, 15, 10, 5 or 3.

Fusion Proteins

Fusion proteins comprising proteins or polypeptide fragments of SCC-112 can also be constructed. Fusion proteins are useful for generating antibodies against amino acid sequences and for use in various assay systems. For example, fusion proteins can be used to identify proteins which interact with a protein of the invention or which interfere with its biological function. Physical methods, such as protein affinity chromatography, or library-based assays for protein-protein interactions, such as the yeast two-hybrid or phage display systems, can also be used for this purpose. Such methods are well known in the art and can also be used as drug screens. Fusion proteins comprising a signal sequence and/or a transmembrane domain of SCC-112 or a fragment thereof can be used to target other protein domains to cellular locations in which the domains are not normally found, such as bound to a cellular membrane or secreted extracellularly.

A fusion protein comprises two protein segments fused together by means of a peptide bond. Amino acid sequences for use in fusion proteins of the invention can utilize the amino acid sequence encoded by a nucleic acid sequence comprising the sequence shown in FIG. 1B (SEQ ID NO:2) or can be prepared from biologically active variants of FIG. 1B (SEQ ID NO:2), such as those described above. The first protein segment can consist of a full-length SCC-112.

Other first protein segments can consist of at least 8, 10, 12, 15, 18, 19, 20, 25, 50, 75, 100, 108 contiguous amino acids selected from SEQ ID NO:2. The contiguous amino acids listed herein are not limiting and also include all intermediate lengths such as 20, 21, 22, etc.; 70, 71, 72, etc.

The second protein segment can be a full-length protein or a polypeptide fragment. Proteins commonly used in fusion protein construction include β-galactosidase, β-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Additionally, epitope tags can be used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, and herpes simplex virus (HSV) BP 16 protein fusions.

These fusions can be made, for example, by covalently linking two protein segments or by standard procedures in the art of molecular biology. Recombinant DNA methods can be used to prepare fusion proteins, for example, by making a DNA construct which comprises a coding sequence comprising the sequence contained in FIG. 1B (SEQ ID NO:1) in proper reading frame with a nucleotide encoding the second protein segment and expressing the DNA construct in a host cell, as is known in the art. Many kits for constructing fusion proteins are available from companies that supply research labs with tools for experiments, including, for example, Promega Corporation (Madison, Wis.), Stratagene (La Jolla, Calif.), Clontech (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Proteins, fusion proteins, or polypeptides of the invention can be produced by recombinant DNA methods. For production of recombinant proteins, fusion proteins, or polypeptides, a coding sequence of the nucleotide sequence shown in FIG. 1B (SEQ ID NO:1) can be expressed in prokaryotic or eukaryotic host cells using expression systems known in the art. These expression systems include bacterial, yeast, insect, and mammalian cells.

The resulting expressed protein can then be purified from the culture medium or from extracts of the cultured cells using purification procedures known in the art. For example, for proteins fully secreted into the culture medium, cell-free medium can be diluted with sodium acetate and contacted with a cation exchange resin, followed by hydrophobic interaction chromatography. Using this method, the desired protein or polypeptide is typically greater than 95% pure. Further purification can be undertaken, using, for example, any of the techniques listed above.

It may be necessary to modify a protein produced in yeast or bacteria, for example by phosphorylation or glycosylation of the appropriate sites, in order to obtain a functional protein. Such covalent attachments can be made using known chemical or enzymatic methods.

SCC-112 protein or polypeptide of the invention can also be expressed in cultured host cells in a form which will facilitate purification. For example, a protein or polypeptide can be expressed as a fusion protein comprising, for example, maltose binding protein, glutathione-S-transferase, or thioredoxin, and purified using a commercially available kit. Kits for expression and purification of such fusion proteins are available from companies such as New England BioLabs, Pharmacia, and Invitrogen. Proteins, fusion proteins, or polypeptides can also be tagged with an epitope, such as a "Flag" epitope (Kodak), and purified using an antibody which specifically binds to that epitope.

The coding sequence disclosed herein can also be used to construct transgenic animals, such as cows, goats, pigs, or sheep. Female transgenic animals can then produce proteins, polypeptides, or fusion proteins of the invention in their milk. Methods for constructing such animals are known and widely used in the art.

Alternatively, synthetic chemical methods, such as solid phase peptide synthesis, can be used to synthesize a secreted protein or polypeptide. General means for the production of peptides, analogs or derivatives are outlined in Chemistry and Biochemistry of Amino Acids, Peptides, and Proteins—A Survey of Recent Developments, B. Weinstein, ed. (1983). Substitution of D-amino acids for the normal L-stereoisomer can be carried out to increase the half-life of the molecule.

Typically, homologous polynucleotide sequences can be confirmed by hybridization under stringent conditions, as is known in the art. For example, using the following wash conditions: 2×SSC (0.3 M NaCl, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each, homologous sequences can be identified which contain at most about 25-30% basepair mismatches. More preferably, homologous nucleic acid strands contain 15-25% basepair mismatches, even more preferably 5-15% basepair mismatches.

The invention also provides polynucleotide probes which can be used to detect complementary nucleotides sequences, for example, in hybridization protocols such as Northern or Southern blotting or in situ hybridizations. Polynucleotide probes of the invention comprise at least 12, 13, 14, 15, 16, 17, 18, 19, 20, 30, or 40 or more contiguous nucleotides of the sequence contained in FIG. 1B (SEQ ID NO:1). Polynucleotide probes of the invention can comprise a detectable label, such as a radioisotopic, fluorescent, enzymatic, or chemiluminescent label.

Isolated genes corresponding to the cDNA sequences disclosed herein are also provided. Standard molecular biology methods can be used to isolate the corresponding genes using the cDNA sequences provided herein. These methods include preparation of probes or primers from the nucleotide sequence shown in FIG. 1B (SEQ ID NO:1) for use in identifying or amplifying the genes from mammalian, including human, genomic libraries or other sources of human genomic DNA.

Polynucleotide molecules of the invention can also be used as primers to obtain additional copies of the polynucleotides, using polynucleotide amplification methods. Polynucleotide molecules can be propagated in vectors and cell lines using techniques well known in the art. Polynucleotide molecules can be on linear or circular molecules. They can be on autonomously replicating molecules or on molecules without replication sequences. They can be regulated by their own or by other regulatory sequences, as is known in the art.

Polynucleotide Constructs

Polynucleotide molecules comprising the coding sequences disclosed herein can be used in a polynucleotide construct, such as a DNA or RNA construct. Polynucleotide molecules of the invention can be used, for example, in an expression construct to express all or a portion of a protein, variant, fusion protein, or single-chain antibody in a host cell. An expression construct comprises a promoter which is functional in a chosen host cell. The skilled artisan can readily select an appropriate promoter from the large number of cell type-specific promoters known and used in the art. The expression construct can also contain a transcription terminator which is functional in the host cell. The expression construct comprises a polynucleotide segment which encodes all or a portion of the desired protein. The polynucleotide segment is located downstream from the promoter. Transcription of the polynucleotide segment initiates at the promoter. The expression construct can be linear or circular and can contain sequences, if desired, for autonomous replication.

Host Cells

An expression construct can be introduced into a host cell. The host cell comprising the expression construct can be any suitable prokaryotic or eukaryotic cell. Expression systems in bacteria include those described in Chang et al., *Nature* (1978) 275:615; Goeddel et al., *Nature* (1979) 281: 544; Goeddel et al., *Nucleic Acids Res.* (1980) 8:4057; EP 36,776; U.S. Pat. No. 4,551,433; deBoer et al., *Proc. Natl. Acad. Sci. USA* (1983) 80: 21-25; and Siebenlist et al., *Cell* (1980) 20: 269.

Expression systems in yeast include those described in Hinnen et al., *Proc. Natl. Acad. Sci. USA* (1978) 75: 1929; Ito et al., *J Bacteriol*. (1983) 153: 163; Kurtz et al., *Mol. Cell. Biol*. (1986) 6:142; Kunze et al., *J Basic Microbiol*. (1985) 25: 141; Gleeson et al., *J. Gen. Microbiol*. (1986) 132: 3459, Roggenkamp et al., *Mol. Gen. Genet*. (1986) 202:302); Das et al., *J Bacteriol*. (1984) 158: 1165; De Louvencourt et al., *J Bacteriol*. (1983) 154: 737, Van den Berg et al., *Bio/Technology* (1990) δ: 135; Kunze et al., *J. Basic Microbiol*. (1985) 25: 141; Cregg et al., *Mol. Cell. Biol*. (1985) 8: 3376; U.S. Pat. No. 4,837,148; U.S. Pat. No. 4,929,555; Beach and Nurse, *Nature* (1981) 300: 706; Davidow et al., *Curr. Genet*. (1985) 1p: 380; Gaillardin et al., *Curr. Genet*. (1985) 10: 49; Ballance et al., *Biochem. Biophys. Res. Commun*. (1983) 112: 284-289; Tilburn et al., *Gene* (1983) 26: 205-22; Yelton et al., *Proc. Natl. Acad, Sci. USA* (1984) 81: 1470-1474; Kelly and Hynes, *EMBO J*. (1985) 4: 475-479; EP 244,234; and WO 91/00357.

Expression of heterologous genes in insects can be accomplished as described in U.S. Pat. No. 4,745,051; Friesen et al., (1986) "The Regulation of Baculovirus Gene Expression" in: THE MOLECULAR BIOLOGY OF BACULOVIRUSES (W. Doerfler, ed.); EP 127,839; EP 155,476; Vlak et al., *J. Gen. Virol.* (1988) 69: 765-776; Miller et al., *Ann. Rev. Microbiol.* (1988) 42: 177; Carbonell et al., *Gene* (1988) 73: 409; Maeda et al., *Nature* (1985) 315: 592-594; Lebacq-Verheyden et. al., *Mol. Cell. Biol.* (1988) δ: 3129; Smith et al., *Proc. Natl. Acad. Sci. USA* (1985) 82: 8404; Miyajima et al., *Gene* (1987) 58: 273; and Martin et al., *DNA* (1988) 7.99. Numerous baculoviral strains and variants and corresponding permissive insect host cells from hosts are described in Luckow et al., *Bio/Technology* (1988) δ: 47-55, Miller et al., in GENERIC ENGINEERING (Setlow, J. K. et al. eds.), Vol. 8 (Plenum Publishing, 1986), pp. 277-279; and Maeda et al., *Nature*, (1985) 315: 592-594.

Mammalian expression can be accomplished as described in Dijkema et al., *EMBO J.* (1985) 4: 761; Gorman et al., *Proc. Natl. Acad. Sci. USA* (1982b) 79: 6777; Boshart et al., *Cell* (1985) 41: 521; and U.S. Pat. No. 4,399,216. Other features of mammalian expression can be facilitated as described in Ham and Wallace, *Meth Enz.* (1979) 58: 44; Barnes and Sato, *Anal. Biochem.* (1980) 102: 255; U.S. Pat. No. 4,767,704; U.S. Pat. No. 4,657,866; U.S. Pat. No. 4,927,762; U.S. Pat. No. 4,560,655; WO 90/103430, WO 87/00195, and U.S. RE 30,985.

Expression constructs can be introduced into host cells using any technique known in the art. These techniques include transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and calcium phosphate-mediated transfection.

Expression of an endogenous gene encoding a protein of the invention can also be manipulated by introducing by homologous recombination a DNA construct comprising a transcription unit in frame with the endogenous gene, to form a homologously recombinant cell comprising the transcription unit. The transcription unit comprises a targeting sequence, a regulatory sequence, an exon, and an unpaired splice donor site. The new transcription unit can be used to turn the endogenous gene on or off as desired. This method of affecting endogenous gene expression is taught in U.S. Pat. No. 5,641,670.

The targeting sequence is a segment of at least 10, 12, 15, 20, or 50 contiguous nucleotides from the nucleotide sequence shown in FIG. 1B (SEQ ID NO:1). The transcription unit is located upstream to a coding sequence of the endogenous gene. The exogenous regulatory sequence directs transcription of the coding sequence of the endogenous gene.

SCC-112 can also include hybrid and modified forms of SCC-112 proteins including fusion proteins, SCC-112 fragments and hybrid and modified forms in which certain amino acids have been deleted or replaced, modifications such as where one or more amino acids have been changed to a modified amino acid or unusual amino acid, and modifications such as glycosylations so long as the hybrid or modified form retains at least one of the biological activities of SCC-112. By retaining the biological activity of SCC-112, it is meant that the protein modulates cancer cell proliferation or apoptosis, although not necessarily at the same level of potency as that of SCC-112 as described herein.

Also included within the meaning of substantially homologous is any SCC-112 which may be isolated by virtue of cross-reactivity with antibodies to the SCC-112 described herein or whose encoding nucleotide sequences including genomic DNA, mRNA or cDNA may be isolated through hybridization with the complementary sequence of genomic or subgenomic nucleotide sequences or cDNA of the SCC-112 herein or fragments thereof. It will also be appreciated by one skilled in the art that degenerate DNA sequences can encode human SCC-112 and these are also intended to be included within the present invention as are allelic variants of SCC-112.

Preferred SCC-112 of the present invention have been identified and isolated in purified form as described. Also preferred is SCC-112 prepared by recombinant DNA technology. By "pure form" or "purified form" or "substantially purified form" it is meant that a SCC-112 composition is substantially free of other proteins which are not SCC-112.

The present invention also includes therapeutic or pharmaceutical compositions comprising SCC-112 in an effective amount for treating patients with disease, and a method comprising administering a therapeutically effective amount of SCC-112. These compositions and methods are useful for treating a number of diseases including cancer. One skilled in the art can readily use a variety of assays known in the art to determine whether SCC-112 would be useful in promoting survival or functioning in a particular cell type.

In certain circumstances, it may be desirable to modulate or decrease the amount of SCC-112 expressed. Thus, in another aspect of the present invention, SCC-112 anti-sense oligonucleotides can be made and a method utilized for diminishing the level of expression of SCC-112 by a cell comprising administering one or more SCC-112 anti-sense oligonucleotides. By SCC-112 anti-sense oligonucleotides reference is made to oligonucleotides that have a nucleotide sequence that interacts through base pairing with a specific complementary nucleic acid sequence involved in the expression of SCC-112 such that the expression of SCC-112 is reduced. Preferably, the specific nucleic acid sequence involved in the expression of SCC-112 is a genomic DNA molecule or mRNA molecule that encodes SCC-112. This genomic DNA molecule can comprise regulatory regions of the SCC-112 gene, or the coding sequence for mature SCC-112 protein.

The term complementary to a nucleotide sequence in the context of SCC-112 antisense oligonucleotides and methods therefor means sufficiently complementary to such a sequence as to allow hybridization to that sequence in a cell, i.e., under physiological conditions. The SCC-112 antisense oligonucleotides preferably comprise a sequence containing from about 8 to about 100 nucleotides and more preferably the SCC-112 antisense oligonucleotides comprise from about 15 to about 30 nucleotides. The SCC-112 antisense oligonucleotides can also contain a variety of modifications that confer resistance to nucleolytic degradation such as, for example, modified internucleoside linages (Uhlmann and Peyman, *Chemical Reviews* 90:543-548 1990; Schneider and Banner, *Tetrahedron Lett.* 31:335, 1990 which are incorporated by reference), modified nucleic acid bases as disclosed in U.S. Pat. No. 5,958,773 and patents disclosed therein, and/or sugars and the like.

Any modifications or variations of the antisense molecule which are known in the art to be broadly applicable to antisense technology are included within the scope of the invention. Such modifications include preparation of phosphorus-containing linkages as disclosed in U.S. Pat. Nos. 5,536,821; 5,541,306; 5,550,111; 5,563,253; 5,571,799; 5,587,361, 5,625,050 and 5,958,773.

The antisense compounds of the invention can include modified bases. The antisense oligonucleotides of the invention can also be modified by chemically linking the oligonucleotide to one or more moieties or conjugates to enhance the activity, cellular distribution, or cellular uptake of the antisense oligonucleotide. Such moieties or conjugates include lipids such as cholesterol, cholic acid, thioether, aliphatic chains, phospholipids, polyamines, polyethylene glycol (PEG), palmityl moieties, and others as disclosed in, for example, U.S. Pat. Nos. 5,514,758, 5,565,552, 5,567,810, 5,574,142, 5,585,481, 5,587,371, 5,597,696 and 5,958,773.

Chimeric antisense oligonucleotides are also within the scope of the invention, and can be prepared from the present inventive oligonucleotides using the methods described in, for example, U.S. Pat. Nos. 5,013,830, 5,149,797, 5,403,711, 5,491,133, 5,565,350, 5,652,355, 5,700,922 and 5,958,773.

In the antisense art, a certain degree of routine experimentation is required to select optimal antisense molecules for particular targets. To be effective, the antisense molecule preferably is targeted to an accessible, or exposed, portion of the target RNA molecule. Although in some cases information is available about the structure of target mRNA molecules, the current approach to inhibition using antisense is via experimentation. mRNA levels in the cell can be measured routinely in treated and control cells by reverse transcription of the mRNA and assaying the cDNA levels. The biological effect can be determined routinely by measuring cell growth, proliferation or viability as is known in the art. Assays for measuring apoptosis are also known.

Measuring the specificity of antisense activity by assaying and analyzing cDNA levels is an art-recognized method of validating antisense results. It has been suggested that RNA from treated and control cells should be reverse-transcribed and the resulting cDNA populations analyzed. (Branch, A. D., *T.I.B.S.* 23:45-50, 1998.)

The therapeutic or pharmaceutical compositions of the present invention can be administered by any suitable route known in the art including for example intravenous, subcutaneous, intramuscular, transdermal, intrathecal or intracerebral. Administration can be either rapid as by injection or over a period of time as by slow infusion or administration of slow release formulation.

SCC-112 can also be linked or conjugated with agents that provide desirable pharmaceutical or pharmacodynamic properties. For example, SCC-112 can be coupled to any substance known in the art to promote penetration or transport across the blood-brain barrier such as an antibody to the transferrin receptor, and administered by intravenous injection (see, for example, Friden et al., *Science* 259:373-377, 1993 which is incorporated by reference). Furthermore, SCC-112 can be stably linked to a polymer such as polyethylene glycol to obtain desirable properties of solubility, stability, half-life and other pharmaceutically advantageous properties. (See, for example, Davis et al., *Enzyme Eng.* 4:169-73, 1978; Buruham, *Am. J. Hosp. Pharm.* 51:210-218, 1994 which are incorporated by reference.)

The compositions are usually employed in the form of pharmaceutical preparations. Such preparations are made in a manner well known in the pharmaceutical art. One preferred preparation utilizes a vehicle of physiological saline solution, but it is contemplated that other pharmaceutically acceptable carriers such as physiological concentrations of other non-toxic salts, five percent aqueous glucose solution, sterile water or the like may also be used. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous. SCC-112 can also be incorporated into a solid or semi-solid biologically compatible matrix which can be implanted into tissues requiring treatment.

The carrier can also contain other pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically-acceptable excipients for modifying or maintaining release or absorption or penetration across the blood-brain barrier. Such excipients are those substances usually and customarily employed to formulate dosages for parenteral administration in either unit dosage or multi-dose form or for direct infusion into the cerebrospinal fluid by continuous or periodic infusion.

Dose administration can be repeated depending upon the pharmacokinetic parameters of the dosage formulation and the route of administration used.

It is also contemplated that certain formulations containing SCC-112 are to be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art. The formulations can also contain substances that diminish proteolytic degradation and promote absorption such as, for example, surface active agents.

The specific dose is calculated according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the activity disclosed herein in assay preparations of target cells. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

In one embodiment of this invention, SCC-112 may be therapeutically administered by implanting into patients vectors or cells capable of producing a biologically-active form of SCC-112 or a precursor of SCC-112, i.e., a molecule that can be readily converted to a biological-active form of SCC-112 by the body. In one approach cells that secrete SCC-112 may be encapsulated into semipermeable membranes for implantation into a patient. The cells can be cells that normally express SCC-112 or a precursor thereof or the cells can be transformed to express SCC-112 or a precursor thereof. It is preferred that the cell be of human origin and that the SCC-112 be human SCC-112 when the patient is human. However, the formulations and methods herein can be used for veterinary as well as human applications and the term "patient" as used herein is intended to include human and veterinary patients.

In a number of circumstances it would be desirable to determine the levels of SCC-112 in a patient. The identification of SCC-112 along with the present report showing expression of SCC-112 provides the basis for the conclusion that the presence of SCC-112 serves a normal physiological function related to cell growth and survival. Endogenously produced SCC-112 may also play a role in certain disease conditions.

The term "detection" as used herein in the context of detecting the presence of SCC-112 in a patient is intended to include the determining of the amount of SCC-112 or the ability to express an amount of SCC-112 in a patient, the estimation of prognosis in terms of probable outcome of a disease and prospect for recovery, the monitoring of the SCC-112 levels over a period of time as a measure of status of the condition, and the monitoring of SCC-112 levels for determining a preferred therapeutic regimen for the patient.

To detect the presence of SCC-112 in a patient, a sample is obtained from the patient. The sample can be a tissue biopsy sample or a sample of blood, plasma, serum, CSF or the like. SCC-112 tissue expression is disclosed in the examples. Samples for detecting SCC-112 can be taken from these tissue. When assessing peripheral levels of SCC-112, it is preferred that the sample be a sample of blood, plasma or serum. When assessing the levels of SCC-112 in the central nervous system a preferred sample is a sample obtained from cerebrospinal fluid or neural tissue.

In some instances it is desirable to determine whether the SCC-112 gene is intact in the patient or in a tissue or cell line within the patient. By an intact SCC-112 gene, it is meant that there are no alterations in the gene such as point mutations, deletions, insertions, chromosomal breakage, chromosomal rearrangements and the like wherein such alteration might alter production of SCC-112 or alter its biological activity, stability or the like to lead to disease processes. Thus, in one embodiment of the present invention a method is provided for detecting and characterizing any alterations in the SCC-112 gene. The method comprises providing an oligonucleotide that contains the SCC-112 cDNA, genomic DNA or a fragment thereof or a derivative thereof. By a derivative of an oligonucleotide, it is meant that the derived oligonucleotide is substantially the same as the sequence from which it is derived in that the derived sequence has sufficient sequence complementarily to the sequence from which it is derived to hybridize to the SCC-112 gene. The derived nucleotide sequence is not necessarily physically derived from the nucleotide sequence, but may be generated in any manner including for example, chemical synthesis or DNA replication or reverse transcription or transcription.

Typically, patient genomic DNA is isolated from a cell sample from the patient and digested with one or more restriction endonucleases such as, for example, Taql and Alul. Using the Southern blot protocol, which is well known in the art, this assay determines whether a patient or a particular tissue in a patient has an intact SCC-112 gene or a SCC-112 gene abnormality.

Hybridization to a SCC-112 gene would involve denaturing the chromosomal DNA to obtain a single-stranded DNA; contacting the single-stranded DNA with a gene probe associated with the SCC-112 gene sequence; and identifying the hybridized DNA-probe to detect chromosomal DNA containing at least a portion of a human SCC-112 gene.

The term "probe" as used herein refers to a structure comprised of a polynucleotide that forms a hybrid structure with a target sequence, due to complementarity of probe sequence with a sequence in the target region. Oligomers suitable for use as probes may contain a minimum of about 8-12 contiguous nucleotides which are complementary to the targeted sequence and preferably a minimum of about 20.

The SCC-112 gene probes of the present invention can be DNA or RNA oligonucleotides and can be made by any method known in the art such as, for example, excision, transcription or chemical synthesis. Probes may be labeled with any detectable label known in the art such as, for example, radioactive or fluorescent labels or enzymatic marker. Labeling of the probe can be accomplished by any method known in the art such as by PCR, random priming, end labeling, nick translation or the like. One skilled in the art will also recognize that other methods not employing a labeled probe can be used to determine the hybridization. Examples of methods that can be used for detecting hybridization include Southern blotting, fluorescence in situ hybridization, and single-strand conformation polymorphism with PCR amplification.

Hybridization is typically carried out at 25°-45° C., more preferably at 32°-40° C. and more preferably at 370-38° C. The time required for hybridization is from about 0.25 to about 96 hours, more preferably from about one to about 72 hours, and most preferably from about 4 to about 24 hours.

SCC-112 gene abnormalities can also be detected by using the PCR method and primers that flank or lie within the SCC-112 gene. The PCR method is well known in the art. Briefly, this method is performed using two oligonucleotide primers which are capable of hybridizing to the nucleic acid sequences flanking a target sequence that lies within a SCC-112 gene and amplifying the target sequence. The terms "oligonucleotide primer" as used herein refers to a short strand of DNA or RNA ranging in length from about 8 to about 30 bases. The upstream and downstream primers are typically from about 20 to about 30 base pairs in length and hybridize to the flanking regions for replication of the nucleotide sequence. The polymerization is catalyzed by a DNA-polymerase in the presence of deoxynucleotide triphosphates or nucleotide analogs to produce double-stranded DNA molecules. The double strands are then separated by any denaturing method including physical, chemical or enzymatic. Commonly, a method of physical denaturation is used involving heating the nucleic acid, typically to temperatures from about 80° C. to 105° C. for times ranging from about 1 to about 10 minutes. The process is repeated for the desired number of cycles.

The primers are selected to be substantially complementary to the strand of DNA being amplified. Therefore, the primers need not reflect the exact sequence of the template, but must be sufficiently complementary to selectively hybridize with the strand being amplified.

After PCR amplification, the DNA sequence comprising SCC-112 or a fragment thereof is then directly sequenced and analyzed by comparison of the sequence with the sequences disclosed herein to identify alterations which might change activity or expression levels or the like.

In another embodiment, a method for detecting SCC-112 is provided based upon an analysis of tissue expressing the SCC-112 gene. Certain tissues such as those identified below in Example 6 and 7 have been found to express the SCC-112 gene. The method comprises hybridizing a polynucleotide to mRNA from a sample of tissue that normally expresses the SCC-112 gene. The sample is obtained from a patient suspected of having an abnormality in the SCC-112 gene or in the SCC-112 gene of particular cells.

To detect the presence of mRNA encoding SCC-112 protein, a sample is obtained from a patient. The sample can be from blood or from a tissue biopsy sample. The sample may be treated to extract the nucleic acids contained therein. The resulting nucleic acid from the sample is subjected to gel electrophoresis or other size separation techniques.

The mRNA of the sample is contacted with a DNA sequence serving as a probe to form hybrid duplexes. The use of a labeled probes as discussed above allows detection of the resulting duplex.

When using the cDNA encoding SCC-112 protein or a derivative of the cDNA as a probe, high stringency conditions can be used in order to prevent false positives, that is the hybridization and apparent detection of SCC-112 nucleotide sequences when in fact an intact and functioning SCC-112 gene is not present. When using sequences derived from the SCC-112 cDNA, less stringent conditions could be used, however, this would be a less preferred approach because of the likelihood of false positives. The stringency of hybridization is determined by a number of factors during hybridization and during the washing procedure, including temperature, ionic strength, length of time and concentration of formamide. These factors are outlined in, for example, Sambrook et al. (Sambrook et al., 1989, supra).

In order to increase the sensitivity of the detection in a sample of mRNA encoding the SCC-112 protein, the technique of reverse transcription/polymerization chain reaction (RT/PCR) can be used to amplify cDNA transcribed from mRNA encoding the SCC-112 protein. The method of RT/PCR is well known in the art, and can be performed as follows. Total cellular RNA is isolated by, for example, the standard guanidium isothiocyanate method and the total RNA is reverse transcribed. The reverse transcription method involves synthesis of DNA on a template of RNA using a reverse transcriptase enzyme and a 3' end primer. Typically, the primer contains an oligo(dT) sequence. The cDNA thus produced is then amplified using the PCR method and SCC-112 specific primers. (Belyavsky et al., *Nucl. Acid Res.* 17:2919-2932, 1989; Krug and Berger, *Methods in Enzymology,* 152:316-325, Academic Press, NY, 1987 which are incorporated by reference).

The polymerase chain reaction method is performed as described above using two oligonucleotide primers that are substantially complementary to the two flanking regions of the DNA segment to be amplified. Following amplification, the PCR product is then electrophoresed and detected by ethidium bromide staining or by phosphoimaging.

The present invention further provides for methods to detect the presence of the SCC-112 protein in a sample obtained from a patient. Any method known in the art for detecting proteins can be used. Such methods include, but are not limited to immunodiffusion, immunoelectrophoresis, immunochemical methods, binder-ligand assays, immunohistochemical techniques, agglutination and complement assays. (*Basic and Clinical Immunology,* 217-262, Sites and Terr, eds., Appleton & Lange, Norwalk, Conn., 1991, which is incorporated by reference). Preferred are binder-ligand immunoassay methods including reacting antibodies with an epitope or epitopes of the SCC-112 protein and competitively displacing a labeled SCC-112 protein or derivative thereof.

As used herein, a derivative of the SCC-112 protein is intended to include a polypeptide in which certain amino acids have been deleted or replaced or changed to modified or unusual amino acids wherein the SCC-112 derivative is biologically equivalent to SCC-112 and wherein the polypeptide derivative cross-reacts with antibodies raised against the SCC-112 protein. By cross-reaction it is meant that an antibody reacts with an antigen other than the one that induced its formation.

Numerous competitive and non-competitive protein binding immunoassays are well known in the art. Antibodies employed in such assays may be unlabeled, for example as used in agglutination tests, or labeled for use in a wide variety of assay methods. Labels that can be used include radionuclides, enzymes, fluorescers, chemiluminescers, enzyme substrates or co-factors, enzyme inhibitors, particles, dyes and the like for use in radioimmunoassay (RIA), enzyme immunoassays, e.g., enzyme-linked immunosorbent assay (ELISA), fluorescent immunoassays and the like.

Polyclonal or monoclonal antibodies to the protein or an epitope thereof can be made for use in immunoassays by any of a number of methods known in the art. By epitope reference is made to an antigenic determinant of a polypeptide. An epitope could comprise 3 amino acids in a spatial conformation which is unique to the epitope. Generally an epitope consists of at least 5 such amino acids. Methods of determining the spatial conformation of amino acids are known in the art, and include, for example, x-ray crystallography and 2 dimensional nuclear magnetic resonance.

One approach for preparing antibodies to a protein is the selection and preparation of an amino acid sequence of all or part of the protein, chemically synthesizing the sequence and injecting it into an appropriate animal, usually a rabbit or a mouse.

Oligopeptides can be selected as candidates for the production of an antibody to the SCC-112 protein based upon the oligopeptides lying in hydrophilic regions, which are thus likely to be exposed in the mature protein. Peptide sequence used to generate antibodies against any fragment of SCC-112 that typically is at least 5-6 amino acids in length, optionally fused to an immunogenic carrier protein, e.g. KLH or BSA.

Additional oligopeptides can be determined using, for example, the Antigenicity Index, Welling, G. W. et al., *FEBS Lett.* 188:215-218 (1985), incorporated herein by reference.

In other embodiments of the present invention, humanized monoclonal antibodies are provided, wherein the antibodies are specific for SCC-112. The phrase "humanized antibody" refers to an antibody derived from a non-human antibody, typically a mouse monoclonal antibody. Alternatively, a humanized antibody may be derived from a chimeric antibody that retains or substantially retains the antigen-binding properties of the parental, non-human, antibody but which exhibits diminished immunogenicity as compared to the parental antibody when administered to humans. The phrase "chimeric antibody," as used herein, refers to an antibody containing sequence derived from two different antibodies (see, e.g., U.S. Pat. No. 4,816,567) which typically originate from different species. Most typically, chimeric antibodies comprise human and murine antibody fragments, generally human constant and mouse variable regions.

Because humanized antibodies are far less immunogenic in humans than the parental mouse monoclonal antibodies, they can be used for the treatment of humans with far less risk of anaphylaxis. Thus, these antibodies may be preferred in therapeutic applications that involve in vivo administration to a human such as, e.g., use as radiation sensitizers for the treatment of neoplastic disease or use in methods to reduce the side effects of, e.g., cancer therapy.

Humanized antibodies may be achieved by a variety of methods including, for example: (1) grafting the non-human complementarity determining regions (CDRs) onto a human framework and constant region (a process referred to in the art as "humanizing"), or, alternatively, (2) transplanting the entire non-human variable domains, but "cloaking" them with a human-like surface by replacement of surface residues (a process referred to in the art as "veneering"). In the present invention, humanized antibodies will include both "humanized" and "veneered" antibodies. These methods are disclosed in, e.g., Jones et al., *Nature* 321:522-525 (1986); Morrison et al., *Proc. Natl. Acad. Sci, U.S.A.*, 81:6851-6855 (1984); Morrison and Oi, *Adv. Immunol.*, 44:65-92 (1988); Verhoeyer et al., *Science* 239:1534-1536 (1988); Padlan, *Molec. Immun.* 28:489-498 (1991); Padlan, *Molec. Immunol.* 31(3):169-217 (1994); and Kettleborough, C. A. et al., *Protein Eng.* 4(7):773-83 (1991) each of which is incorporated herein by reference.

The phrase "complementarity determining region" refers to amino acid sequences which together define the binding affinity and specificity of the natural Fv region of a native immunoglobulin binding site. See, e.g., Chothia et al., *J. Mol. Biol.* 196:901-917 (1987); Kabat et al., U.S. Dept. of Health and Human Services NIH Publication No. 91-3242 (1991). The phrase "constant region" refers to the portion of the antibody molecule that confers effector functions. In the present invention, mouse constant regions are substituted by human constant regions. The constant regions of the subject humanized antibodies are derived from human immunoglobulins. The heavy chain constant region can be selected from any of the five isotypes: alpha, delta, epsilon, gamma or mu.

One method of humanizing antibodies comprises aligning the non-human heavy and light chain sequences to human heavy and light chain sequences, selecting and replacing the non-human framework with a human framework based on such alignment, molecular modeling to predict the conformation of the humanized sequence and comparing to the conformation of the parent antibody. This process is followed by repeated back mutation of residues in the CDR region which disturb the structure, of the CDRs until the predicted conformation of the humanized sequence model closely approximates the conformation of the non-human CDRs of the parent non-human antibody. Such humanized antibodies may be further derivatized to facilitate uptake and clearance, e.g, via Ashwell receptors. See, e.g., U.S. Pat. Nos. 5,530,101 and 5,585,089 which patents are incorporated herein by reference.

Humanized antibodies to SCC-112 can also be produced using transgenic animals that are engineered to contain human immunoglobulin loci. For example, WO 98/24893 discloses transgenic animals having a human Ig locus wherein the animals do not produce functional endogenous immunoglobulins due to the inactivation of endogenous heavy and light chain loci. WO 91/10741 also discloses transgenic non-primate mammalian hosts capable of mounting an immune response to an immunogen, wherein the antibodies have primate constant and/or variable regions, and wherein the endogenous immunoglobulin-encoding loci are substituted or inactivated. WO 96/30498 discloses the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy claims, and express an exogenous immunoglobulin locus comprising one or more xenogeneic constant regions.

Using a transgenic animal described above, an immune response can be produced to a selected antigenic molecule, and antibody-producing cells can be removed from the animal and used to produce hybridomas that secrete human monoclonal antibodies. Immunization protocols, adjuvants, and the like are known in the art, and are used in immunization of, for example, a transgenic mouse as described in WO 96/33735. This publication discloses monoclonal antibodies against a variety of antigenic molecules including IL-6, IL-8, TNF, human CD4, L-selectin, gp39, and tetanus toxin. The monoclonal antibodies can be tested for the ability to inhibit or neutralize the biological activity or physiological effect of the corresponding protein. WO 96/33735 discloses that monoclonal antibodies against IL-8, derived from immune cells of transgenic mice immunized with IL-8, blocked IL-8-induced functions of neutrophils. Human monoclonal antibodies with specificity for the antigen used to immunize transgenic animals are also disclosed in WO 96/34096.

In the present invention, SCC-112 polypeptides of the invention and variants thereof are used to immunize a transgenic animal as described above. Monoclonal antibodies are made using methods known in the art, and the specificity of the antibodies is tested using isolated SCC-112 polypeptides.

Methods for preparation of the SCC-112 protein or an epitope thereof include, but are not limited to chemical synthesis, recombinant DNA techniques or isolation from biological samples. Chemical synthesis of a peptide can be performed, for example, by the classical Merrifeld method of solid phase peptide synthesis (Merrifeld, *J. Am. Chem. Soc.* 85:2149, 1963 which is incorporated by reference) or the FMOC strategy on a Rapid Automated Multiple Peptide Synthesis system (E. I. du Pont de Nemours Company, Wilmington, Del.) (Caprino and Han, *J. Org. Chem.* 37:3404, 1972 which is incorporated by reference).

Polyclonal antibodies can be prepared by immunizing rabbits or other animals by injecting antigen followed by subsequent boosts at appropriate intervals. The animals are bled and sera assayed against purified SCC-112 protein usually by ELISA or by bioassay based upon the ability to block the action of SCC-112. In a non-limiting example, an antibody to SCC-112 can block the binding of SCC-112 to Disheveled protein. When using avian species, e.g., chicken, turkey and the like, the antibody can be isolated from the yolk of the egg. Monoclonal antibodies can be prepared after the method of Milstein and Kohler by fusing splenocytes from immunized mice with continuously replicating tumor cells such as myeloma or lymphoma cells. (Milstein and Kohler, *Nature* 256:495-497, 1975; Gulfre and Milstein, *Methods in Enzymology: Immunochemical Techniques* 73:146, Langone and Banatis eds., Academic. Press, 1981 which are incorporated by reference). The hybridoma cells so formed are then cloned by limiting dilution methods and supernates assayed for antibody production by ELISA, RIA or bioassay.

The unique ability of antibodies to recognize and specifically bind to target proteins provides an approach for treating an overexpression of the protein. Thus, another aspect of the present invention provides for a method for preventing or treating diseases involving overexpression of the SCC-112 protein by treatment of a patient with specific antibodies to the SCC-112 protein.

Specific antibodies, either polyclonal or monoclonal, to the SCC-112 protein can be produced by any suitable method known in the art as discussed above. For example, murine or human monoclonal antibodies can be produced by hybridoma technology or, alternatively, the SCC-112 protein, or an immunologically active fragment thereof, or an anti-idiotypic antibody, or fragment thereof can: be administered to an animal to elicit the production of antibodies capable of recognizing and binding to the SCC-112 protein. Such antibodies can be from any class of antibodies including, but not limited to IgG, IgA, IgM, IgD, and IgE or in the case of avian species, IgY and from any subclass of antibodies.

The availability of SCC-112 allows for the identification of small molecules and low molecular weight compounds that inhibit the binding of SCC-112 to binding partners, through routine application of high-throughput screening methods (HTS). HTS methods generally refer to technologies that permit the rapid assaying of lead compounds for therapeutic potential. HTS techniques employ robotic handling of test materials, detection of positive signals, and interpretation of data. Lead compounds may be identified via the incorporation of radioactivity or through optical assays that rely on absorbence, fluorescence or luminescence as read-outs. Gonzalez, J. E. et al., (1998) *Curr. Opin. Biotech.* 9:624-631.

Model systems are available that can be adapted for use in high throughput screening for compounds that inhibit the interaction of SCC-112 with its ligand, for example by competing with SCC-112 for ligand binding. Sarubbi et al., (1996) *Anal. Biochem.* 237:70-75 describe cell-free, non-isotopic assays for discovering molecules that compete with natural ligands for binding to the active site of IL-1 receptor. Martens, C. et al., (1999) *Anal. Biochem.* 273:20-31 describe a generic particle-based nonradioactive method in which a labeled ligand binds to its receptor immobilized on a particle; label on the particle decreases in the presence of a molecule that competes with the labeled ligand for receptor binding.

The therapeutic SCC-112 polynucleotides and polypeptides of the present invention may be utilized in gene delivery vehicles. The gene delivery vehicle may be of viral or non-viral origin (see generally, Jolly, Cancer Gene Therapy 1:51-64 (1994); Kimura, *Human Gene Therapy* 5:845-852 (1994); Connelly, *Human Gene Therapy* 1:185-193 (1995); and Kaplift, *Nature Genetics* 6:148-153 (1994)). Gene therapy vehicles for delivery of constructs including a coding sequence of a therapeutic of the invention can be administered either locally or systemically. These constructs can utilize viral or non-viral vector approaches. Expression of such coding sequences can be induced using endogenous mammalian or heterologous promoters. Expression of the coding sequence can be either constitutive or regulated.

The present invention can employ recombinant retroviruses which are constructed to carry or express a selected nucleic acid molecule of interest. Retrovirus vectors that can be employed include those described in EP 0 415 731; WO 90/0793 6; WO 94/03622; WO 93/25698; WO 93/25234; U.S. Pat. No. 5,219,740; WO 93/11230; WO 93/10218; Vile and Hart, *Cancer Res.* 53:3860-3864 (1993); Vile and Hart, *Cancer Res.* 53:962-967 (1993); Ram et al., *Cancer Res.* 53:83-88 (1993); Takamiya et al., *J. Neurosci. Res.* 33:493-503 (1992); Baba et al., *J. Neurosurg.* 79:729-735 (1993); U.S. Pat. No. 4,777,127; GB Patent No. 2,200,651; and EP 0 345 242. Preferred recombinant retroviruses include those described in WO 91/02805.

Packaging cell lines suitable for use with the above-described retroviral vector constructs may be readily prepared (see PCT publications WO 95/3 0763 and WO 92/05266), and used to create producer cell lines (also termed vector cell lines) for the production of recombinant vector particles. Within particularly preferred embodiments of the invention, packaging cell lines are made from human (such as HT1080 cells) or mink parent cell lines, thereby allowing production of recombinant retroviruses that can survive inactivation in human serum.

The present invention also employs alphavirus-based vectors that can function as gene delivery vehicles. Such vectors can be constructed from a wide variety of alphaviruses, including, for example, Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532). Representative examples of such vector systems include those described in U.S. Pat. Nos. 5,091,309; 5,217,879; and 5,185,440; and PCT Publication Nos. WO 92/10578; WO 94/21792; WO 95/27069; WO 95/27044; and WO 95/07994.

Gene delivery vehicles of the present invention can also employ parvovirus such as adeno-associated virus (AAV) vectors. Representative examples include the AAV vectors disclosed by Srivastava in WO 93/09239, Samulski et al., *J. Vir.* 63:3822-3828 (1989); Mendelson et al., *Virol* 166:154-165 (1988); and Flotte et al., *P.N.A.S.* 90:10613-10617 (1993).

Representative examples of adenoviral vectors include those described by Berkner, *Biotechniques* 6:616-627 (Biotechniques); Rosenfeld et al., *Science* 252:431-434 (1991); WO 93/19191; Kolls et al., *P.N.A.S.* 215-219 (1994); Kass-Bisler et al., *P.N.A.S.* 90:11498-11502 (1993); Guzman et al., *Circulation* 88:2838-2848 (1993); Guzman et al., *Cir. Res.* 73:1202-1207 (1993); Zabner et al., *Cell* 75:207-216 (1993); Li et al., *Hum. Gene Ther.* 4:403-409 (1993); Cailaud et al., *Eur. J. Neurosci.* 5:1287-1291 (1993); Vincent et al., *Nat Genet.* 5:130-134 (1993); Jaffe et al., *Nat. Genet.* 1:372-378 (1992); and Levrero et al., *Gene* 101:195-202 (1992). Exemplary adenoviral gene therapy vectors employable in this invention also include those described in WO 94/12649, WO 93/03769; WO 93/19191; WO 94/28938; WO 95/11984 and WO 95/00655. Administration of DNA linked to killed adenovirus as described in Curiel, *Hum. Gene Ther.* 3:147-154 (1992) may be employed.

Other gene delivery vehicles and methods may be employed, including polycationic condensed DNA linked or unlinked to killed adenovirus alone, for example Curiel, *Hum. Gene Ther.* 3:147-154 (1992); ligand-linked DNA, for example see Wu, *J. Biol. Chem.* 264:16985-16987 (1989); eukaryotic cell delivery vehicles cells; deposition of photopolymerized hydrogel materials; hand-held gene transfer particle gun, as described in U.S. Pat. No. 5,149,655; ionizing radiation as described in U.S. Pat. No. 5,206,152 and in WO 92/11033; nucleic charge neutralization or fusion with cell membranes. Additional approaches are described in Philip, *Mol. Cell. Biol.* 14:2411-2418 (1994), and in Woffendin, *Proc. Natl. Acad. Sci.* 91:1581-1585 (1994).

Naked DNA may also be employed. Exemplary naked DNA introduction methods are described in WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm. Liposomes that can act as gene delivery vehicles are described in U.S. Pat. No. 5,422, 120, PCT Patent Publication Nos. WO 95/13 796, WO 94/23697, and WO 9 1/14445, and EP No. 0 524 968.

Further non-viral delivery suitable for use includes mechanical delivery systems such as the approach described in Woffendin et al., *Proc. Natl. Acad. Sci. USA* 91(24): 11581-11585 (1994). Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and PCT Patent Publication No. WO 92/11033.

SCC-112 may also be used in screens to identify drugs for treatment of cancers which involve over-activity of the encoded protein, or new targets which would be useful in the identification of new drugs.

For all of the preceding embodiments, the clinician will determine, based on the specific condition, whether SCC-112 polypeptides or polynucleotides, antibodies to SCC-112, or small molecules such as peptide analogues or antagonists, will be the most suitable form of treatment. These forms are all within the scope of the invention.

EXAMPLE

Cell Culture, and Reagents: Human breast cancer cell line MDA-MB 435, prostate cancer lines Du145 and PC-3, and pancreatic cancer cell lines Aspc1 and Colo-357 were grown in DMEM (Invitrogen) supplemented with 10% heat inactivated fetal bovine serum. Human prostate cancer cell line LNCaP was cultured in improved minimal essential medium (Biofluids) supplemented with 5% fetal calf serum. The cells were grown in 75-cm$^2$ tissue culture flasks in a humidified atmosphere of 5% $CO_2$ and 95% air at 37° C.

Sequence Data Analysis: The sequences were assembled using Autoassembler (ABI). BLAST sequence database search, conserved domain prediction and open reading frame (ORF) search were done using NCBI programs (Altschul, S. F., Madden, T. L., Schaffer, A. A., Zhang, J., Zhang, Z., Miller, W., & Lipman, D. J. (1997) Nucleic Acids Res. 25, 3389-3402). Multiple sequence alignment was performed by MULTIALIGN program, and motifs and other sequence signature sequences were detected by pSORT (Corpet, F., (1988) Nucl. Acids Res 16, 10881-10890). The prediction of the possible nature of the protein including localization based on structural characteristics was performed by Reinhardt's method (Nakai, K., and Kanehisa, M. (1992) *Genomics* 14, 897-911).

RNA Isolation and Northern Hybridization: MDA-MB 435 cells were synchronized at different cell cycle stages, and total RNA was isolated with Trizol reagent according to the manufacturer's instructions (Invitrogen Life technologies, Inc.). For Northern hybridization and analysis, the total RNA was electrophoresed on 1% agarose-formaldehyde gel, transferred overnight to the nylon membrane, (Hybond N$^+$, Amersham Pharmacia Biotech, Piscataway, N.J.) and fixed by UV cross linking and baking at 80° C. for 2 h. Multi tissue blots (H, H3, and F) containing poly A+ RNA from adult and fetal tissues were purchased from CLONTECH (Paulo Alto, Calif.). For hybridization 10$^6$ cpm/ml of $^{32}$P labeled SCC-112 cDNA was used as probe, and hybridizations were performed at 68° C. using Expresshyb (CLONTECH) followed by washings with 2×SSC and 0.1% SDS at room temperature and 0.1×SSC containing 0.1% SDS at 68° C. Membranes were reprobed with radio labeled glyceraldehydes-3-phosphate dehydrogenase (GAPDH) or actin as internal control. The autoradiographs were scanned and bands were quantified using IMAGEQUANT software (Molecular Dynamics, Sunnyvale, Calif.).

Generation of Anti-SCC-112 Antibody: A rabbit polyclonal antibody was generated against a peptide representing 20 amino acid residues (aa) at the C-terminus of the SCC-112 protein (1278, 1297, KLQDLAKKAAPAERQIDLQR (SEQ ID NO:3)). This peptide was coupled to keyhole limpet hemocyanin and injected into rabbits. Custom antibody production services of the Zymed Laboratories, Inc., (San Francisco, Calif.) were used for production of the rabbit anti-SCC-112 antibody.

Western Blot Analysis: The cells were rinsed with ice-cold PBS and scrapped in lysis solution containing Tris (20 mM, pH 8.0), NaCl (150 mM), 1% NP-40 (w/v), 10% glycerol (w/v), 1 mM phenylmethylsulphonyl fluoride (PMSF), aprotinin (20 ug/ml) and leupeptin (20 ug/ml). The cells were lysed for 45 min with vigorous shaking at 4° C. and centrifuged at 12,000×g for 15 min at 4° C. Fifty micrograms of total protein were heat denatured by boiling for 5 min in SDS-PAGE loading buffer. After SDS-PAGE, the proteins were electrophoretically transferred on to PVDF membrane (Millipore). The membrane was blocked with 5% non-fat dry milk in PBST (PBS containing 0.05% Tween 20) and incubated with 1:2000 dilution of anti-SCC—S2 antibody for 1 h. After washing 3 times for 10 min each in PBST, membrane was incubated with 1:20,000 dilution of HRP conjugated goat anti-rabbit secondary antibody for 1 h. The membrane was washed extensively for 1 h and stained using ECL chemiluminescent method (NEN).

Immunofluorescence Microscopy: MDA-MB 435 cells were grown on cover slips. The cells were fixed in chilled methanol for 10 min followed by rinsing and washing in PBS, pH 7.5. The cells were permeabilized using 0.01% Triton X-100 for 30 sec. Non-specific binding was blocked by treating the cells with 1% BSA (w/v) in PBS for 30 min. For immunostaining, cells were incubated with 1:1000 dilution of anti-SCC-112 antibody in 1% BSA/PBS for 1 h followed by 3 washings of 10 min each with PBS. Texas-Red conjugated goat anti-rabbit secondary antibody (1:200 dilution in 1% BSA in PBS for 1 h) was used to detect the antigen antibody complex. After three washings of 10 min each with PBS, the nuclei were stained with DAPI for 1 min. The cover slips were rinsed finally with PBS and mounted on a glass slide with cells facing the slide in fluoromount-G (Southern Biotechnology Associates Inc., Birmingham, Ala.), followed by visualization under a fluorescence microscope (Zeiss).

Cell Synchronization and Flow Cytometry: Logarithmically growing MDA-MB 435 cells were treated with 4 ug/ml aphidicolin, a DNA polymerase-a inhibitor, for 24 h to synchronize cells at $G_1$/S phase. The cells were washed thoroughly to wash off the aphidicolin and medium replaced with fresh media and incubations continued for various time points, 0 h (G1/S phase-enriched cells), 4 h (S phase-enriched cells) and 8 h ($G_2$/M phase-enriched cells). In addition, cells were treated with 100 ng/ml of Nocodazole, a tubulin anti-mitotic agent for 16 h to arrest the cells in M phase. The cell cycle distribution profiles were determined using a Fluorescence Activated Cell Sorter (Becton Dickinson).

Array Hybridization and Quantification: Expression profiles SCC-112 mRNA in tumor vs corresponding normal tissue were determined using a commercially available Cancer Profiling Array blot (CLONTECH) that contains a total of 241 paired normal and tumor cDNA samples from individual patients spotted side by side on a nylon membrane. Hybridization of Cancer Profiling Array using $^{32}$P labeled SCC-112 cDNA was performed as described in the CLONTECH Cancer Profiling Array User Manual (PR11929). After hybridization, the membrane was reprobed with ubiquitin cDNA as internal control. The autoradiographs were scanned and signals were quantified using IMAGEQUANT software (Molecular Dynamics, Sunnyvale, Calif.).

Human Tissues and Processing: Histologically confirmed frozen human tissues were obtained from Co-operative Human Tissue Network (CHTN) resource of the NCl (NIH). The tissues were homogenized in RIPA lysis buffer (NaCl, 150 mM, pH 7.5; Sodium Deoxycholate, 1% (w/v); Triton X-100, 1% v/v; SDS, 0.1% w/v;) containing 2 mM phenylmethylsulphonyl fluoride (PMSF), aprotinin (20 ug/ml) and leupeptin (20 ug/ml). After incubation on ice for 30 min, the tissue extracts were centrifuged at 12000×g for 15 min at 4° C. followed by SDS-PAGE and Western blot analysis.

The chromosome localization search for SCC-112 sequence at locus link in NCBI database showed that SCC-112 gene is localized at chromosome 4p14. Genomic sequence (~120 kb) corresponding to SCC-112 cDNA was located in the NCBI Human Genome Data Base (Genbank accession number AC022862) and Celera Human Genome Data base (clone IDs GA_x2HTBL52FRR and GA_x2HTBL52FKR). Alignment of SCC-112 cDNA and genomic DNA sequences revealed that SCC-112 gene is composed of at least 38 exons. Cancer-related rearrangements on chromosome 4p have been reported. Therefore, genomic organization of SCC-112 gene may have a diagnostic application in human cancers.

In the data shown in FIG. 10 renal tumor and matched normal adjacent tissues from a total of twenty patients were examined. A visual examination of the western blots indicated that two bands, ~150 kDa and ~65 kDa represent the SCC-112 protein. Both bands were seen in 90% of the normal renal tissues examined (n=20), whereas only 15% of the renal tumors expressed these two bands (n=20). It is also important to note that only 20% of the tumor tissues had ~65 kDa band with or without the presence of ~150 kDa protein (n=20), whereas 95% of the normal renal tissues examined exhibited the mutant form (~65 kDa) with or without ~150 kDa SCC-112 (n=20). Based on these data, ~150 kDa SCC-112 protein seems to be necessary but not sufficient for tumor suppression, whereas ~65 kDa is necessary and may be sufficient for tumor suppression in normal kidney tissue. Alternatively, the ~150 kDa and ~65 kDa proteins may complement each other in the exhibition of the tumor suppressor phenotype, a hall mark of most normal tissues.

Table 1 (shown in FIG. 13) shows the statistical analysis of the fold change in SCC-112 mRNA expression level in tumor tissue versus corresponding normal tissue from individual cancer patients.

Statistical methods: For each type of tumor, a pair of SCC-112 mRNA expression levels for each patient is available in normal and tumor tissue. The ratio of the SCC-112 mRNA expression values has been calculated in normal to tumor tissue. The ratios have been transformed to natural logarithms. Under the null hypothesis of no difference in gene expression levels between normal and tumor tissues, the average ratio should be one and the average of the natural logs of the ratios should equal 0. To test the null hypothesis for each type of tumor, a one-sample t test of the natural logs of the ratios was performed and two-sided P values were calculated. 95% confidence intervals were calculated based on the natural log transformations of the data and transformed back to obtain the confidence limits on the ratio scale.

From Table 1, the ratios for breast tumors (1.22), and kidney tumors (1.22) are significantly greater than one, P<0.0001, and the 95% confidence intervals for the ratios are substantially above one. For tumors in the uterus, the average ratio of normal to tumor tissue was 0.90, which is significantly less than one, P=0.02, and the 95% confidence intervals for the ratios are below one.

The present invention has been described with reference to specific embodiments. However, this invention is intended to cover those changes and substitutions, which may be made by those skilled in the art without departing from the spirit and scope of the appended claims.

---

What is claimed is:

1. An isolated nucleic acid molecule having the nucleic acid sequence consisting essentially of that set forth in SEQ ID NO: 1.

2. An isolated nucleic acid molecule encoding the amino acid sequence consisting essentially of that set forth in SEQ ID NO: 2.

3. The isolated nucleic acid molecule of claim 1, which is DNA.

4. The isolated nucleic acid molecule of claim 2, which is DNA.

5. A method of making a recombinant vector comprising inserting a nucleic acid molecule of any of claims 1, 2, 3 or 4 into a vector in operable linkage to a promoter.

6. A recombinant vector produced by the method of claim 5.

7. A method of making a recombinant host cell comprising introducing the recombinant vector of claim 6 into a host cell.

8. A recombinant host cell produced by the method of claim 7.

9. A recombinant method of producing a polypeptide, comprising culturing the recombinant host cell of claim 8 under conditions such that said polypeptide is expressed and recovering said polypeptide.

* * * * *

SEQUENCE LISTING

```
<160> NUMBER OF SEQ ID NOS: 3

<210> SEQ ID NO 1
<211> LENGTH: 6744
<212> TYPE: DNA
<213> ORGANISM: Homo sapiens
<220> FEATURE:
<221> NAME/KEY: CDS
<222> LOCATION: (232)..(4122)

<400> SEQUENCE: 1
ggacctcgca ggccaagaat tcggcacgag gggcgccggc tcccggggca cggacggccg      60
ggcgcgcgcc tctgcgaggg gcgtccgggt ccgagtcggc ggtccgggcc ggcgcgaggt     120
gcgtgcgggc gggccgcggg ggtcccggac ggacacaagc gcacacactc ccggaagatc     180
gcttaccctc cgggggtaaa agagatcacc gacaagatca ccacggacga g atg atc     237
                                                         Met Ile
                                                           1 aaa cgc ctg aag atg gta gtg aaa acc ttt atg gat atg gat cag gac     285
Lys Arg Leu Lys Met Val Val Lys Thr Phe Met Asp Met Asp Gln Asp
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 5   |     |     |     |     | 10  |     |     |     |     | 15  |     |     |     |      |
| tca | gaa | gat | gaa | aaa | cag | cag | tat | ctc | cca | cta | gcc | ttg | cat | ctt | gca | 333  |
| Ser | Glu | Asp | Glu | Lys | Gln | Gln | Tyr | Leu | Pro | Leu | Ala | Leu | His | Leu | Ala |      |
|     |     | 20  |     |     |     |     | 25  |     |     |     |     | 30  |     |     |     |      |
| tct | gaa | ttc | ttc | ctc | agg | aac | ccc | aat | aaa | gat | gtg | cgt | ctc | ctt | gta | 381  |
| Ser | Glu | Phe | Phe | Leu | Arg | Asn | Pro | Asn | Lys | Asp | Val | Arg | Leu | Leu | Val |      |
|     | 35  |     |     |     |     | 40  |     |     |     |     | 45  |     |     |     | 50  |      |
| gca | tgt | tgt | ttg | gct | gat | atc | ttt | cgt | atc | tat | gcc | cca | gaa | gct | cca | 429  |
| Ala | Cys | Cys | Leu | Ala | Asp | Ile | Phe | Arg | Ile | Tyr | Ala | Pro | Glu | Ala | Pro |      |
|     |     |     | 55  |     |     |     |     | 60  |     |     |     |     | 65  |     |     |      |
| tat | act | tcc | cat | gat | aaa | ctt | aag | gac | ata | ttt | ttg | ttt | att | acc | aga | 477  |
| Tyr | Thr | Ser | His | Asp | Lys | Leu | Lys | Asp | Ile | Phe | Leu | Phe | Ile | Thr | Arg |      |
|     |     |     | 70  |     |     |     |     | 75  |     |     |     |     | 80  |     |     |      |
| caa | tta | aaa | ggt | ttg | gag | gat | aca | aag | agt | cca | cag | ttt | aat | aga | tac | 525  |
| Gln | Leu | Lys | Gly | Leu | Glu | Asp | Thr | Lys | Ser | Pro | Gln | Phe | Asn | Arg | Tyr |      |
|     |     | 85  |     |     |     |     | 90  |     |     |     |     | 95  |     |     |     |      |
| ttt | tat | tta | tta | gag | aat | tta | gct | tgg | gtt | aaa | tca | tat | aac | atc | tgc | 573  |
| Phe | Tyr | Leu | Leu | Glu | Asn | Leu | Ala | Trp | Val | Lys | Ser | Tyr | Asn | Ile | Cys |      |
|     | 100 |     |     |     |     | 105 |     |     |     |     | 110 |     |     |     |     |      |
| ttt | gaa | ttg | gaa | gat | tgc | aat | gaa | att | ttt | att | cag | ctt | ttt | aga | act | 621  |
| Phe | Glu | Leu | Glu | Asp | Cys | Asn | Glu | Ile | Phe | Ile | Gln | Leu | Phe | Arg | Thr |      |
| 115 |     |     |     |     | 120 |     |     |     |     | 125 |     |     |     |     | 130 |      |
| ctc | ttc | tca | gtg | atc | aac | aat | agc | cac | aat | aag | aag | gta | caa | atg | cac | 669  |
| Leu | Phe | Ser | Val | Ile | Asn | Asn | Ser | His | Asn | Lys | Lys | Val | Gln | Met | His |      |
|     |     |     | 135 |     |     |     |     | 140 |     |     |     |     | 145 |     |     |      |
| atg | cta | gat | ttg | atg | agt | tct | atc | atc | atg | gaa | ggt | gat | gga | gtt | act | 717  |
| Met | Leu | Asp | Leu | Met | Ser | Ser | Ile | Ile | Met | Glu | Gly | Asp | Gly | Val | Thr |      |
|     |     |     | 150 |     |     |     |     | 155 |     |     |     |     | 160 |     |     |      |
| caa | gaa | tta | ttg | ggc | tcc | att | ctt | att | aac | ctc | att | cct | gca | cat | aag | 765  |
| Gln | Glu | Leu | Leu | Gly | Ser | Ile | Leu | Ile | Asn | Leu | Ile | Pro | Ala | His | Lys |      |
|     |     | 165 |     |     |     |     | 170 |     |     |     |     | 175 |     |     |     |      |
| aac | tta | aat | aaa | cag | tcc | ttt | gac | ctt | gca | aaa | gtg | cta | ttg | aaa | aga | 813  |
| Asn | Leu | Asn | Lys | Gln | Ser | Phe | Asp | Leu | Ala | Lys | Val | Leu | Leu | Lys | Arg |      |
|     | 180 |     |     |     |     | 185 |     |     |     |     | 190 |     |     |     |     |      |
| aca | gtc | cag | act | att | gag | gca | tgc | att | gcc | aat | ttt | ttc | aat | caa | gtc | 861  |
| Thr | Val | Gln | Thr | Ile | Glu | Ala | Cys | Ile | Ala | Asn | Phe | Phe | Asn | Gln | Val |      |
| 195 |     |     |     |     | 200 |     |     |     |     | 205 |     |     |     |     | 210 |      |
| ctg | gtg | ctg | gga | aga | tca | tca | gta | agt | gat | ttg | tca | gaa | cat | gta | ttt | 909  |
| Leu | Val | Leu | Gly | Arg | Ser | Ser | Val | Ser | Asp | Leu | Ser | Glu | His | Val | Phe |      |
|     |     |     | 215 |     |     |     |     | 220 |     |     |     |     | 225 |     |     |      |
| gat | ctg | att | cag | gaa | ctt | ttt | gct | ata | gat | cct | cat | tta | tta | tta | tcc | 957  |
| Asp | Leu | Ile | Gln | Glu | Leu | Phe | Ala | Ile | Asp | Pro | His | Leu | Leu | Leu | Ser |      |
|     |     |     | 230 |     |     |     |     | 235 |     |     |     |     | 240 |     |     |      |
| gtc | atg | cca | cag | ctt | gaa | ttc | aaa | cta | aag | agc | aat | gat | gga | gaa | gag | 1005 |
| Val | Met | Pro | Gln | Leu | Glu | Phe | Lys | Leu | Lys | Ser | Asn | Asp | Gly | Glu | Glu |      |
|     |     | 245 |     |     |     |     | 250 |     |     |     |     | 255 |     |     |     |      |
| cga | tta | gct | gtt | gtt | cga | ctt | cta | gct | aaa | ttg | ttt | ggc | tcc | aaa | gat | 1053 |
| Arg | Leu | Ala | Val | Val | Arg | Leu | Leu | Ala | Lys | Leu | Phe | Gly | Ser | Lys | Asp |      |
|     | 260 |     |     |     |     | 265 |     |     |     |     | 270 |     |     |     |     |      |
| tct | gat | ttg | gca | aca | cag | aat | cgt | cct | ctt | tgg | caa | tgt | ttt | ctt | gga | 1101 |
| Ser | Asp | Leu | Ala | Thr | Gln | Asn | Arg | Pro | Leu | Trp | Gln | Cys | Phe | Leu | Gly |      |
| 275 |     |     |     |     | 280 |     |     |     |     | 285 |     |     |     |     | 290 |      |
| cga | ttt | aat | gat | att | cat | gtt | cct | gtg | aga | tta | gaa | agt | gtg | aaa | ttt | 1149 |
| Arg | Phe | Asn | Asp | Ile | His | Val | Pro | Val | Arg | Leu | Glu | Ser | Val | Lys | Phe |      |
|     |     |     | 295 |     |     |     |     | 300 |     |     |     |     | 305 |     |     |      |
| gcc | agt | cat | tgt | tta | atg | aat | cac | cca | gat | tta | gcg | aag | gat | ctc | aca | 1197 |
| Ala | Ser | His | Cys | Leu | Met | Asn | His | Pro | Asp | Leu | Ala | Lys | Asp | Leu | Thr |      |
|     |     |     | 310 |     |     |     |     | 315 |     |     |     |     | 320 |     |     |      |
| gaa | tat | tta | aag | gtt | aga | tca | cat | gat | cca | gaa | gaa | gct | att | cgt | cat | 1245 |

-continued

| | | | | | | | | | | | | | | | |
|---|---|---|---|---|---|---|---|---|---|---|---|---|---|---|---|
| Glu | Tyr | Leu | Lys | Val | Arg | Ser | His | Asp | Pro | Glu | Glu | Ala | Ile | Arg | His |
| | | 325 | | | | 330 | | | | | 335 | | | | |

```
gat gtc att gtt act ata ata aca gct gcc aag agg gac ctg gcc tta    1293
Asp Val Ile Val Thr Ile Ile Thr Ala Ala Lys Arg Asp Leu Ala Leu
    340             345                 350 gta aat gat cag ctg ctt ggc ttt gta agg gaa aga aca ctg gat aaa    1341
Val Asn Asp Gln Leu Leu Gly Phe Val Arg Glu Arg Thr Leu Asp Lys
355             360                 365                 370 cgg tgg cga gta aga aaa gaa gct atg atg ggt ctg gct cag ctt tat    1389
Arg Trp Arg Val Arg Lys Glu Ala Met Met Gly Leu Ala Gln Leu Tyr
                375                 380                 385 aag aaa tac tgt ctt cat ggt gaa gca gga aag gaa gct gca gag aaa    1437
Lys Lys Tyr Cys Leu His Gly Glu Ala Gly Lys Glu Ala Ala Glu Lys
            390                 395                 400 gtc agc tgg ata aag gac aaa ctt ctg cat att tat tat cag aac agc    1485
Val Ser Trp Ile Lys Asp Lys Leu Leu His Ile Tyr Tyr Gln Asn Ser
        405                 410                 415 att gac gac aaa ctg ttg gta gag aaa atc ttt gct cag tat ctt gtc    1533
Ile Asp Asp Lys Leu Leu Val Glu Lys Ile Phe Ala Gln Tyr Leu Val
    420                 425                 430 ccc cac aac ctg gaa aca gaa gag aga atg aaa tgc tta tat tac tta    1581
Pro His Asn Leu Glu Thr Glu Glu Arg Met Lys Cys Leu Tyr Tyr Leu
435                 440                 445                 450 tat gct agt ttg gat cca aat gct gta aaa gct ctc aac gaa atg tgg    1629
Tyr Ala Ser Leu Asp Pro Asn Ala Val Lys Ala Leu Asn Glu Met Trp
                455                 460                 465 aag tgt cag aac atg ctt cgg agc cat gta cgc gaa cta ttg gat ttg    1677
Lys Cys Gln Asn Met Leu Arg Ser His Val Arg Glu Leu Leu Asp Leu
            470                 475                 480 cac aag cag cct aca tca gag gct aac tgt tct gcc atg ttt gga aaa    1725
His Lys Gln Pro Thr Ser Glu Ala Asn Cys Ser Ala Met Phe Gly Lys
        485                 490                 495 ctg atg acc ata gca aag aat ttg cct gac ccc ggg aaa gca caa gat    1773
Leu Met Thr Ile Ala Lys Asn Leu Pro Asp Pro Gly Lys Ala Gln Asp
    500                 505                 510 ttt gtg aag aaa ttt aac cag gtt ctc ggc gat gat gag aaa ctt cgg    1821
Phe Val Lys Lys Phe Asn Gln Val Leu Gly Asp Asp Glu Lys Leu Arg
515                 520                 525                 530 tct cag ttg gag tta tta att agc cca acc tgt tct tgc aaa caa gca    1869
Ser Gln Leu Glu Leu Leu Ile Ser Pro Thr Cys Ser Cys Lys Gln Ala
                535                 540                 545 gat att tgt gtg aga gaa ata gcc cgg aaa ctt gca aat cct aag caa    1917
Asp Ile Cys Val Arg Glu Ile Ala Arg Lys Leu Ala Asn Pro Lys Gln
            550                 555                 560 cca aca aat cct ttt cta gag atg gtc aaa ttt ctg ttg gaa aga atc    1965
Pro Thr Asn Pro Phe Leu Glu Met Val Lys Phe Leu Leu Glu Arg Ile
        565                 570                 575 gca cct gtg cac att gat tca gaa gcc ata agt gca cta gtg aaa ttg    2013
Ala Pro Val His Ile Asp Ser Glu Ala Ile Ser Ala Leu Val Lys Leu
    580                 585                 590 atg aat aag tca ata gag ggg aca gca gat gat gaa gag gag ggt gta    2061
Met Asn Lys Ser Ile Glu Gly Thr Ala Asp Asp Glu Glu Glu Gly Val
595                 600                 605                 610 agt cca gat aca gct atc cgt tca gga ctt gaa ctt ctt aag gtt ctg    2109
Ser Pro Asp Thr Ala Ile Arg Ser Gly Leu Glu Leu Leu Lys Val Leu
                615                 620                 625 tct ttt aca cat cct acc tcg ttc cac tct gca gag aca tat gag tcc    2157
Ser Phe Thr His Pro Thr Ser Phe His Ser Ala Glu Thr Tyr Glu Ser
            630                 635                 640
```

-continued

| | | |
|---|---|---|
| ttg tta cag tgc cta aga atg gag gat gac aag gta gca gaa gct gct<br>Leu Leu Gln Cys Leu Arg Met Glu Asp Asp Lys Val Ala Glu Ala Ala<br>645         650         655 | | 2205 |
| att caa att ttt aga aat aca ggt cac aaa ata gaa aca gac ctt ccc<br>Ile Gln Ile Phe Arg Asn Thr Gly His Lys Ile Glu Thr Asp Leu Pro<br>660         665         670 | | 2253 |
| cag ata cga tcg acc tta att ccc att tta cat caa aaa gca aag agg<br>Gln Ile Arg Ser Thr Leu Ile Pro Ile Leu His Gln Lys Ala Lys Arg<br>675         680         685         690 | | 2301 |
| ggt act cca cac caa gca aaa cag gct gtg cac tgt ata cac gcc ata<br>Gly Thr Pro His Gln Ala Lys Gln Ala Val His Cys Ile His Ala Ile<br>        695         700         705 | | 2349 |
| ttc aca aat aaa gaa gtc cag ctt gca cag att ttt gag cca ctc agt<br>Phe Thr Asn Lys Glu Val Gln Leu Ala Gln Ile Phe Glu Pro Leu Ser<br>710         715         720 | | 2397 |
| agg agt ctg aat gct gat gtg cca gaa caa ctt ata act cca tta gtt<br>Arg Ser Leu Asn Ala Asp Val Pro Glu Gln Leu Ile Thr Pro Leu Val<br>725         730         735 | | 2445 |
| tca ttg ggc cac att tct atg tta gca cca gat cag ttt gct tcc cca<br>Ser Leu Gly His Ile Ser Met Leu Ala Pro Asp Gln Phe Ala Ser Pro<br>740         745         750 | | 2493 |
| atg aaa tct gta gta gca aat ttt att gtg aaa gat ctg cta atg aat<br>Met Lys Ser Val Val Ala Asn Phe Ile Val Lys Asp Leu Leu Met Asn<br>755         760         765         770 | | 2541 |
| gac agg tca aca ggt gaa aag aat gga aaa ctg tgg tct cca gat gaa<br>Asp Arg Ser Thr Gly Glu Lys Asn Gly Lys Leu Trp Ser Pro Asp Glu<br>        775         780         785 | | 2589 |
| gag gtt tcc cct gaa gta cta gca aag gta cag gca att aaa ctt ctg<br>Glu Val Ser Pro Glu Val Leu Ala Lys Val Gln Ala Ile Lys Leu Leu<br>790         795         800 | | 2637 |
| gta agg tgg ctg ttg ggt atg aaa aac aac cag tct aaa tct gcc aat<br>Val Arg Trp Leu Leu Gly Met Lys Asn Asn Gln Ser Lys Ser Ala Asn<br>805         810         815 | | 2685 |
| tca acc ctt cgg tta tta tca gcg atg ttg gtt agt gag ggt gac ctg<br>Ser Thr Leu Arg Leu Leu Ser Ala Met Leu Val Ser Glu Gly Asp Leu<br>820         825         830 | | 2733 |
| aca gag caa aag agg atc agt aaa tct gat atg tct cgc ttg cga tta<br>Thr Glu Gln Lys Arg Ile Ser Lys Ser Asp Met Ser Arg Leu Arg Leu<br>835         840         845         850 | | 2781 |
| gct gct ggt agt gcc ata atg aag ctt gct cag gaa cct tgt tac cat<br>Ala Ala Gly Ser Ala Ile Met Lys Leu Ala Gln Glu Pro Cys Tyr His<br>        855         860         865 | | 2829 |
| gaa att att acc cca gaa cag ttt cag ctc tgt gca ctt gtt att aat<br>Glu Ile Ile Thr Pro Glu Gln Phe Gln Leu Cys Ala Leu Val Ile Asn<br>870         875         880 | | 2877 |
| gat gag tgt tac caa gta agg cag ata ttt gct cag aag ctg cat aag<br>Asp Glu Cys Tyr Gln Val Arg Gln Ile Phe Ala Gln Lys Leu His Lys<br>885         890         895 | | 2925 |
| gca ctt gtg aag tta ctc ctc cca ttg gag tat atg gcg atc ttt gcc<br>Ala Leu Val Lys Leu Leu Leu Pro Leu Glu Tyr Met Ala Ile Phe Ala<br>900         905         910 | | 2973 |
| ttg tgt gcc aaa gat cct gtg aag gag aga aga gca cac gca cga caa<br>Leu Cys Ala Lys Asp Pro Val Lys Glu Arg Arg Ala His Ala Arg Gln<br>915         920         925         930 | | 3021 |
| tgt tta ctg aaa aat atc agt ata cgc agg gaa tac att aag cag aat<br>Cys Leu Leu Lys Asn Ile Ser Ile Arg Arg Glu Tyr Ile Lys Gln Asn<br>        935         940         945 | | 3069 |
| cct atg gct act gag aaa tta tta tca ctg ttg cct gaa tat gta gtt<br>Pro Met Ala Thr Glu Lys Leu Leu Ser Leu Leu Pro Glu Tyr Val Val<br>950         955         960 | | 3117 |

```
cca tac atg att cac ctg cta gcc cat gat cca gat ttt aca aga tca    3165
Pro Tyr Met Ile His Leu Leu Ala His Asp Pro Asp Phe Thr Arg Ser
        965                 970                 975 caa gat gtt gat cag ctt cgt gat atc aaa gag tgc cta tgg ttc atg    3213
Gln Asp Val Asp Gln Leu Arg Asp Ile Lys Glu Cys Leu Trp Phe Met
    980                 985                 990 ctt gaa gtt tta atg aca aag aat gaa aac aat agc cat gcc ttt atg    3261
Leu Glu Val Leu Met Thr Lys Asn Glu Asn Asn Ser His Ala Phe Met
995                 1000                1005                1010 aag aag atg gca gag aac atc aag tta acc aga gat gcc cag tct cca    3309
Lys Lys Met Ala Glu Asn Ile Lys Leu Thr Arg Asp Ala Gln Ser Pro
            1015                1020                1025 gat gaa tcc aag aca aat gaa aaa ctg tat aca gta tgt gat gtg gct    3357
Asp Glu Ser Lys Thr Asn Glu Lys Leu Tyr Thr Val Cys Asp Val Ala
        1030                1035                1040 ctc tgt gtt ata aat agt aaa agt gct ttg tgc aat gca gat tca cca    3405
Leu Cys Val Ile Asn Ser Lys Ser Ala Leu Cys Asn Ala Asp Ser Pro
    1045                1050                1055 aag gac cca gtc ctc cca atg aaa ttt ttt aca caa cct gaa aag gac    3453
Lys Asp Pro Val Leu Pro Met Lys Phe Phe Thr Gln Pro Glu Lys Asp
1060                1065                1070 ttc tgt aac gat aag agt tat att tca gaa gag aca aga gta ctt ctg    3501
Phe Cys Asn Asp Lys Ser Tyr Ile Ser Glu Glu Thr Arg Val Leu Leu
1075                1080                1085                1090 tta aca gga aag cca aag cct gct gga gta cta ggt gca gta aat aag    3549
Leu Thr Gly Lys Pro Lys Pro Ala Gly Val Leu Gly Ala Val Asn Lys
            1095                1100                1105 cct tta tca gca acg gga agg aaa ccc tat gtt aga agc act ggc act    3597
Pro Leu Ser Ala Thr Gly Arg Lys Pro Tyr Val Arg Ser Thr Gly Thr
        1110                1115                1120 gag act gga agc aat att aat gta aat tca gag ctg aac cct tca acc    3645
Glu Thr Gly Ser Asn Ile Asn Val Asn Ser Glu Leu Asn Pro Ser Thr
    1125                1130                1135 gga aat cga tca agg gaa cag agt tca gag gca gca gaa act gga gtt    3693
Gly Asn Arg Ser Arg Glu Gln Ser Ser Glu Ala Ala Glu Thr Gly Val
1140                1145                1150 agt gaa aat gaa gag aac cct gtg agg att att tca gtc aca cct gta    3741
Ser Glu Asn Glu Glu Asn Pro Val Arg Ile Ile Ser Val Thr Pro Val
1155                1160                1165                1170 aag aat att gac cca gta aag aat aag gaa att aat tct gat cag gct    3789
Lys Asn Ile Asp Pro Val Lys Asn Lys Glu Ile Asn Ser Asp Gln Ala
            1175                1180                1185 acc cag ggc aac atc agc agt gac cga gga aag aaa aga aca gta aca    3837
Thr Gln Gly Asn Ile Ser Ser Asp Arg Gly Lys Lys Arg Thr Val Thr
        1190                1195                1200 gca gct ggt gca gag aat atc caa caa aaa aca gat gag aaa gta gat    3885
Ala Ala Gly Ala Glu Asn Ile Gln Gln Lys Thr Asp Glu Lys Val Asp
    1205                1210                1215 gaa tcg gga cct ccc gcc cct tcc aaa ccc agg aga gga cgt cga ccc    3933
Glu Ser Gly Pro Pro Ala Pro Ser Lys Pro Arg Arg Gly Arg Arg Pro
1220                1225                1230 aag tct gaa tct cag ggc aat gct acc aaa aat gat gat cta aat aaa    3981
Lys Ser Glu Ser Gln Gly Asn Ala Thr Lys Asn Asp Asp Leu Asn Lys
1235                1240                1245                1250 cct att aac aag gga agg aag aga gct gca gtg ggt cag gag agc cct    4029
Pro Ile Asn Lys Gly Arg Lys Arg Ala Ala Val Gly Gln Glu Ser Pro
            1255                1260                1265 ggg ggt ttg gaa gca ggt aat gcc aaa gca ccc aaa ctg caa gat tta    4077
Gly Gly Leu Glu Ala Gly Asn Ala Lys Ala Pro Lys Leu Gln Asp Leu
```

-continued

|  | 1270 |  |  | 1275 |  |  | 1280 |  |  |  |
|---|---|---|---|---|---|---|---|---|---|---|
| gcc | aaa | aag | gca | gca | cca | gca | gaa | aga | caa att gac tta caa agg | 4122 |
| Ala | Lys | Lys | Ala | Ala | Pro | Ala | Glu | Arg | Gln Ile Asp Leu Gln Arg |  |
|  | 1285 |  |  |  | 1290 |  |  |  | 1295 |  |

```
taaaaatgca tttgcaaagg gagaaaatga aggccaaaca gaagcaggct ccagcttctg    4182
caaaaacttg gattcacaaa tgtccctgaa cagaaaatga agctcacttc agaacacaca    4242
ctctctgcct tgaaaactaa agagactatt acttcctttt cacatgacca caagtcctct    4302
gatggaaatg tacagcagaa actcttgaga gagaggctaa aagcaactct gttctccccc    4362
ttcccctaga cttttcttac gaaaagtcaa taattaagca aattgcttaa cacttggttc    4422
cagttcctgc ctatctggag tttaaatgcg taatacacca ttaatttcca cgctgcagtt    4482
tttattttaa agaaagtaac aagatgtctt tacactgaca ctgaaaattc atccatttta    4542
gagccaggaa ttcccatgtt acacaggaaa aaatagaagt ctactgaatt aatttttaa     4602
aagaaaagag atcagattaa atatttcttt gttttccctt ttggaaactt ttatgtataa    4662
ttctttctgc ctgcctactt ttctgcaaaa atgagatgta cagatttcgg ttccctgcta    4722
tgaaaagtga tgtggtagca atttttataaa tgttgctttc tgattttat cagagtgaga    4782
aaattaaaat tattgatttg caagtagtaa acagttcata ttttgatttc ccctcatttt    4842
agtttaatat aatttgcaat aaatgtacat attgttgttt gtttcataaa gcatatcact    4902
ttaaaatggt ttttactcct gtgattatgt tggaatattt ggaattttaa aggagtaaag    4962
actgtccagc atttggtttt ataatgtttg tcaccagatt tttattaatg taaaaaatca    5022
attttttaaaa aatagttgga ctttggcagc ttttaaggaa agttggaggt gttttaggat    5082
tgctatcaat tttcagcatt gtgctatttg gaaataagtg ttttgctttt gtctgatggt    5142
ctgggctcat tttatgtttt attttagaaa actgttgcat caatatatta tgtttcttgg    5202
cattgttcag cataggtaat gtgtgcactt tatgtgtaca cataatcata tttaagtttt    5262
ttgcataaaa taaatgcttc tagatgtcat ggcagtcttt ttaatctttt tatcatatgc    5322
tttcttgtga atttttttcat gttaaagagc taaagtcata acatgattac agtcaactct    5382
ccattatcta tataaaatag tgactaagcc tcaggttttt aattttgtga taacaaaata    5442
acgaaggcat gtaagacctg attctggagg aacatgaaat ttgtcttttc tcatgtccag    5502
agttctatcc tgcccccact gtccactgta gggtcatccg caaagccta gcagaatgtg     5562
ctcactccat ttccttacac gtttctagca tgggtcagag gaaacaacat ttgtgttata    5622
acttcgtctt gataggctgt agtgtacatg ggatgtaaaa caaacaagtg tatcaaaggt    5682
ggatgattct gttagagtga gtttgagag taaatgtcac ttacgtttct catagatgat     5742
caagagttgg ctgtgtattg actgaaagat gggtaattat tttaaatatg catttacaca    5802
catttaggta tcagaagatg cttagggaac aatggatacc aatgatagaa aatgatacct    5862
ttacagggc  agaaaaatcc ccactcttcc ttattgcctc ttcagaaccc tttagaaagt    5922
ataaaatatt gcctccaaca tgctgaaaaa gagtatctat gcataagtat cagagaagtc    5982
cctcaagcaa tcagtaggtg tgttctattt agagagagt  taaagttctc ttagcatcag    6042
acaacttgat tcctaaggtt tccagtgtgt caccaacaaa aagtgcattg atagggacct    6102
ttgtctcttc ctcccttgga ttaattgccc ggcatcacag tttactagat taccaagtgt    6162
tacatcatat taaataaaat gtagcagaac catctgcatc aatatattcc tgtttagatt    6222
tttgcaggag agaagttaaa aggatttgct ccttgtatga tgtaagtggc ccaccccaat    6282
tttgtaacat gatgcaagtg tctggcacta agggaagcaa gagtagggtt gtggaaagac    6342
```

-continued

```
caagctgatg gggagggact tgtttacggg aattttttta gttttccttt tcaaaggaaa      6402
acattaaaat cccttaggaa tttggtattc acatctcaga gaactacaac acaaaagtgc      6462
agacttatat ttgagaatta atgttaaccc tttgtgtcta gtttgaagct tcttgtattt      6522
gtctaaaaca acaagccaga attttgtatc tcctttgata aaagtgtgt ataatgtaaa       6582 gtagttttgc atattcttgt gctgcacatg ggctgaattt ttaaattttt tttaaaaact      6642
tgaagcagaa ccttgtaatt tgtgtaaatg acaagtgtaa aatcctacca taaaatgcta      6702
aaaatatgca ctgtttcaaa taaaaccaag aaatgcagca tt                         6744
```

<210> SEQ ID NO 2
<211> LENGTH: 1297
<212> TYPE: PRT
<213> ORGANISM: Homo sapiens

<400> SEQUENCE: 2

```
Met Ile Lys Arg Leu Lys Met Val Val Lys Thr Phe Met Asp Met Asp
  1               5                  10                  15

Gln Asp Ser Glu Asp Glu Lys Gln Gln Tyr Leu Pro Leu Ala Leu His
                 20                  25                  30

Leu Ala Ser Glu Phe Phe Leu Arg Asn Pro Asn Lys Asp Val Arg Leu
             35                  40                  45

Leu Val Ala Cys Cys Leu Ala Asp Ile Phe Arg Ile Tyr Ala Pro Glu
         50                  55                  60

Ala Pro Tyr Thr Ser His Asp Lys Leu Lys Asp Ile Phe Leu Phe Ile
 65                  70                  75                  80

Thr Arg Gln Leu Lys Gly Leu Glu Asp Thr Lys Ser Pro Gln Phe Asn
                 85                  90                  95

Arg Tyr Phe Tyr Leu Leu Glu Asn Leu Ala Trp Val Lys Ser Tyr Asn
            100                 105                 110

Ile Cys Phe Glu Leu Glu Asp Cys Asn Glu Ile Phe Ile Gln Leu Phe
        115                 120                 125

Arg Thr Leu Phe Ser Val Ile Asn Asn Ser His Asn Lys Lys Val Gln
    130                 135                 140

Met His Met Leu Asp Leu Met Ser Ser Ile Ile Met Glu Gly Asp Gly
145                 150                 155                 160

Val Thr Gln Glu Leu Leu Gly Ser Ile Leu Ile Asn Leu Ile Pro Ala
                165                 170                 175

His Lys Asn Leu Asn Lys Gln Ser Phe Asp Leu Ala Lys Val Leu Leu
            180                 185                 190

Lys Arg Thr Val Gln Thr Ile Glu Ala Cys Ile Ala Asn Phe Phe Asn
        195                 200                 205

Gln Val Leu Val Leu Gly Arg Ser Ser Val Ser Asp Leu Ser Glu His
    210                 215                 220

Val Phe Asp Leu Ile Gln Glu Leu Phe Ala Ile Asp Pro His Leu Leu
225                 230                 235                 240

Leu Ser Val Met Pro Gln Leu Glu Phe Lys Lys Ser Asn Asp Gly
                245                 250                 255

Glu Glu Arg Leu Ala Val Val Arg Leu Leu Ala Lys Leu Phe Gly Ser
            260                 265                 270

Lys Asp Ser Asp Leu Ala Thr Gln Asn Arg Pro Leu Trp Gln Cys Phe
        275                 280                 285

Leu Gly Arg Phe Asn Asp Ile His Val Pro Val Arg Leu Glu Ser Val
    290                 295                 300
```

```
Lys Phe Ala Ser His Cys Leu Met Asn His Pro Asp Leu Ala Lys Asp
305                 310                 315                 320

Leu Thr Glu Tyr Leu Lys Val Arg Ser His Asp Pro Glu Glu Ala Ile
            325                 330                 335

Arg His Asp Val Ile Val Thr Ile Ile Thr Ala Ala Lys Arg Asp Leu
                340                 345                 350

Ala Leu Val Asn Asp Gln Leu Leu Gly Phe Val Arg Glu Arg Thr Leu
                355                 360                 365

Asp Lys Arg Trp Arg Val Arg Lys Glu Ala Met Met Gly Leu Ala Gln
            370                 375                 380

Leu Tyr Lys Lys Tyr Cys Leu His Gly Glu Ala Gly Lys Glu Ala Ala
385                 390                 395                 400

Glu Lys Val Ser Trp Ile Lys Asp Lys Leu His Ile Tyr Tyr Gln
                405                 410                 415

Asn Ser Ile Asp Asp Lys Leu Leu Val Glu Lys Ile Phe Ala Gln Tyr
                420                 425                 430

Leu Val Pro His Asn Leu Glu Thr Glu Glu Arg Met Lys Cys Leu Tyr
            435                 440                 445

Tyr Leu Tyr Ala Ser Leu Asp Pro Asn Ala Val Lys Ala Leu Asn Glu
450                 455                 460

Met Trp Lys Cys Gln Asn Met Leu Arg Ser His Val Arg Glu Leu Leu
465                 470                 475                 480

Asp Leu His Lys Gln Pro Thr Ser Glu Ala Asn Cys Ser Ala Met Phe
                485                 490                 495

Gly Lys Leu Met Thr Ile Ala Lys Asn Leu Pro Asp Pro Gly Lys Ala
                500                 505                 510

Gln Asp Phe Val Lys Lys Phe Asn Gln Val Leu Gly Asp Asp Glu Lys
            515                 520                 525

Leu Arg Ser Gln Leu Glu Leu Leu Ile Ser Pro Thr Cys Ser Cys Lys
530                 535                 540

Gln Ala Asp Ile Cys Val Arg Glu Ile Ala Arg Lys Leu Ala Asn Pro
545                 550                 555                 560

Lys Gln Pro Thr Asn Pro Phe Leu Glu Met Val Lys Phe Leu Leu Glu
                565                 570                 575

Arg Ile Ala Pro Val His Ile Asp Ser Glu Ala Ile Ser Ala Leu Val
                580                 585                 590

Lys Leu Met Asn Lys Ser Ile Glu Gly Thr Ala Asp Asp Glu Glu Glu
            595                 600                 605

Gly Val Ser Pro Asp Thr Ala Ile Arg Ser Gly Leu Glu Leu Leu Lys
610                 615                 620

Val Leu Ser Phe Thr His Pro Thr Ser Phe His Ser Ala Glu Thr Tyr
625                 630                 635                 640

Glu Ser Leu Leu Gln Cys Leu Arg Met Glu Asp Asp Lys Val Ala Glu
                645                 650                 655

Ala Ala Ile Gln Ile Phe Arg Asn Thr Gly His Lys Ile Glu Thr Asp
                660                 665                 670

Leu Pro Gln Ile Arg Ser Thr Leu Ile Pro Ile Leu His Gln Lys Ala
            675                 680                 685

Lys Arg Gly Thr Pro His Gln Ala Lys Gln Ala Val His Cys Ile His
            690                 695                 700

Ala Ile Phe Thr Asn Lys Glu Val Gln Leu Ala Gln Ile Phe Glu Pro
705                 710                 715                 720
```

```
Leu Ser Arg Ser Leu Asn Ala Asp Val Pro Glu Gln Leu Ile Thr Pro
            725                 730                 735
Leu Val Ser Leu Gly His Ile Ser Met Leu Ala Pro Asp Gln Phe Ala
            740                 745                 750
Ser Pro Met Lys Ser Val Val Ala Asn Phe Ile Val Lys Asp Leu Leu
            755                 760                 765
Met Asn Asp Arg Ser Thr Gly Glu Lys Asn Gly Lys Leu Trp Ser Pro
770                 775                 780
Asp Glu Glu Val Ser Pro Val Leu Ala Lys Val Gln Ala Ile Lys
785                 790                 795                 800
Leu Leu Val Arg Trp Leu Leu Gly Met Lys Asn Asn Gln Ser Lys Ser
            805                 810                 815
Ala Asn Ser Thr Leu Arg Leu Leu Ser Ala Met Leu Val Ser Glu Gly
            820                 825                 830
Asp Leu Thr Glu Gln Lys Arg Ile Ser Lys Ser Asp Met Ser Arg Leu
            835                 840                 845
Arg Leu Ala Ala Gly Ser Ala Ile Met Lys Leu Ala Gln Glu Pro Cys
            850                 855                 860
Tyr His Glu Ile Ile Thr Pro Glu Gln Phe Gln Leu Cys Ala Leu Val
865                 870                 875                 880
Ile Asn Asp Glu Cys Tyr Gln Val Arg Gln Ile Phe Ala Gln Lys Leu
            885                 890                 895
His Lys Ala Leu Val Lys Leu Leu Pro Leu Glu Tyr Met Ala Ile
            900                 905                 910
Phe Ala Leu Cys Ala Lys Asp Pro Val Lys Glu Arg Arg Ala His Ala
            915                 920                 925
Arg Gln Cys Leu Leu Lys Asn Ile Ser Ile Arg Arg Glu Tyr Ile Lys
            930                 935                 940
Gln Asn Pro Met Ala Thr Glu Lys Leu Leu Ser Leu Leu Pro Glu Tyr
945                 950                 955                 960
Val Val Pro Tyr Met Ile His Leu Leu Ala His Asp Pro Asp Phe Thr
            965                 970                 975
Arg Ser Gln Asp Val Asp Gln Leu Arg Asp Ile Lys Glu Cys Leu Trp
            980                 985                 990
Phe Met Leu Glu Val Leu Met Thr Lys Asn Glu Asn Asn Ser His Ala
            995                 1000                1005
Phe Met Lys Lys Met Ala Glu Asn Ile Lys Leu Thr Arg Asp Ala Gln
    1010                1015                1020
Ser Pro Asp Glu Ser Lys Thr Asn Glu Lys Leu Tyr Thr Val Cys Asp
1025                1030                1035                1040
Val Ala Leu Cys Val Ile Asn Ser Lys Ser Ala Leu Cys Asn Ala Asp
                1045                1050                1055
Ser Pro Lys Asp Pro Val Leu Pro Met Lys Phe Phe Thr Gln Pro Glu
        1060                1065                1070
Lys Asp Phe Cys Asn Asp Lys Ser Tyr Ile Ser Glu Glu Thr Arg Val
            1075                1080                1085
Leu Leu Leu Thr Gly Lys Pro Lys Pro Ala Gly Val Leu Gly Ala Val
        1090                1095                1100
Asn Lys Pro Leu Ser Ala Thr Gly Arg Lys Pro Tyr Val Arg Ser Thr
1105                1110                1115                1120
Gly Thr Glu Thr Gly Ser Asn Ile Asn Val Asn Ser Glu Leu Asn Pro
            1125                1130                1135
Ser Thr Gly Asn Arg Ser Arg Glu Gln Ser Ser Glu Ala Ala Glu Thr
```

-continued

```
              1140                1145                1150
Gly Val Ser Glu Asn Glu Glu Asn Pro Val Arg Ile Ile Ser Val Thr
        1155                1160                1165

Pro Val Lys Asn Ile Asp Pro Val Lys Asn Lys Glu Ile Asn Ser Asp
    1170                1175                1180

Gln Ala Thr Gln Gly Asn Ile Ser Ser Asp Arg Gly Lys Lys Arg Thr
1185                1190                1195                1200

Val Thr Ala Ala Gly Ala Glu Asn Ile Gln Gln Lys Thr Asp Glu Lys
            1205                1210                1215

Val Asp Glu Ser Gly Pro Pro Ala Pro Ser Lys Pro Arg Arg Gly Arg
            1220                1225                1230

Arg Pro Lys Ser Glu Ser Gln Gly Asn Ala Thr Lys Asn Asp Asp Leu
        1235                1240                1245

Asn Lys Pro Ile Asn Lys Gly Arg Lys Arg Ala Ala Val Gly Gln Glu
    1250                1255                1260

Ser Pro Gly Gly Leu Glu Ala Gly Asn Ala Lys Ala Pro Lys Leu Gln
1265                1270                1275                1280

Asp Leu Ala Lys Lys Ala Ala Pro Ala Glu Arg Gln Ile Asp Leu Gln
            1285                1290                1295

Arg

<210> SEQ ID NO 3
<211> LENGTH: 20
<212> TYPE: PRT
<213> ORGANISM: Artificial
<220> FEATURE:
<223> OTHER INFORMATION: C-terminus of the SCC-112 Protein

<400> SEQUENCE: 3

Lys Leu Gln Asp Leu Ala Lys Lys Ala Ala Pro Ala Glu Arg Gln Ile
1               5                   10                  15

Asp Leu Gln Arg
            20
```